(12) United States Patent
Coady et al.

(10) Patent No.: US 8,633,296 B1
(45) Date of Patent: Jan. 21, 2014

(54) COMPOSITE HYDROGELS FOR DELIVERY OF BIOLOGICALLY ACTIVE MATERIALS

(75) Inventors: Daniel J. Coady, San Jose, CA (US); Richard A. DiPietro, Campbell, CA (US); Amanda C. Engler, San Jose, CA (US); James L. Hedrick, Pleasanton, CA (US); Ashlynn L. Lee, Singapore (SG); Shrinivas Venkataraman, Singapore (SG); Yi Yan Yang, Singapore (SG)

(73) Assignees: International Business Machines Corporation, Armonk, NY (US); Agency for Science, Technology and Research, Singapore (SG)

( * ) Notice: Subject to any disclaimer, the term of this patent is extended or adjusted under 35 U.S.C. 154(b) by 16 days.

(21) Appl. No.: 13/610,979

(22) Filed: Sep. 12, 2012

(51) Int. Cl.
*C08G 64/18* (2006.01)

(52) U.S. Cl.
USPC ........... 528/370; 528/271; 528/297; 528/302; 528/307; 528/403; 106/287.24; 424/486

(58) Field of Classification Search
None
See application file for complete search history.

(56) References Cited

U.S. PATENT DOCUMENTS

| | | |
|---|---|---|
| 6,639,014 B2 | 10/2003 | Pathak et al. |
| 6,800,663 B2 | 10/2004 | Asgarzadeh et al. |
| 6,923,986 B2 | 8/2005 | Pathak et al. |
| 7,311,901 B2 | 12/2007 | Seo et al. |
| 2007/0104654 A1 | 5/2007 | Hsieh et al. |
| 2008/0152616 A1 | 6/2008 | Seo et al. |
| 2008/0166382 A1 | 7/2008 | Hsieh et al. |

FOREIGN PATENT DOCUMENTS

WO   2005035606 A1   4/2005

OTHER PUBLICATIONS

Lee, Ashlynn L. Z. et al; "The use of cholesterol containing biodegradable block copolymers to exploit hydrophobic interactions for the delivery of anticancer drugs." Biomaterials (2012) 33 p. 1921-1928.*
Lee, et al.,"The use of cholesterol-containing biodegradable block copolymers to exploit hydrophobic interactions for the delivery of anticancer drugs," Biomaterials 33 (2012) 1921-1928. Available online Dec. 3, 2011.
Wei, et al., "Dual-drug delivery system based on hydrogel/micelle composites," Biomaterials 30 (2009) 2606-2613; Available online Jan. 21, 2009.
Zou, et al., "Synthesis and characterization of end-capped biodegradable oligo/poly(trimethylene carbonate)s," J. Biomater. Sci. Polymer Edn__17__10__1093-1106 (2006).

* cited by examiner

*Primary Examiner* — Cecilia J Tsang
*Assistant Examiner* — Fred Reynolds
(74) *Attorney, Agent, or Firm* — Michael R. Roberts

(57) ABSTRACT

A composite hydrogel comprises an amphiphilic triblock copolymer (ABA) and a loaded micelle bound by noncovalent interactions. The loaded micelle comprises a biologically active substance and an amphiphilic diblock copolymer (CD). The A blocks comprise a steroidal repeat unit (repeat unit 1) having both a backbone carbonate and a side chain bearing a steroid functional group. Each of the A blocks has a degree of polymerization of about 0.5 to about 4.0. The B block comprises a first poly(alkylene oxide) backbone. The C block comprises a second poly(alkylene oxide) backbone. The D block comprises a steroidal repeat unit (repeat unit 2) having both a backbone carbonate group and a side chain comprising a steroid functional group. The composite hydrogel is capable of controlled release of the biologically active substance.

27 Claims, 19 Drawing Sheets

Ex. 4, Polymer(0:67)

Ex. 5, Polymer(4:0)

Ex. 6, Polymer(11:0)

Ex. 7, Polymer(8:8)

Ex. 8, Polymer(11:30)

Ex. 9, Polymer(18:55)

Ex. 11 PTX-Polymer(0:67)

Ex. 12 PTX-Polymer(11:0)

Ex. 13 PTX-Polymer(8:8)

Ex. 14 PTX-Polymer(11:30)

COMPOSITE HYDROGELS FOR DELIVERY OF BIOLOGICALLY ACTIVE MATERIALS

PARTIES TO A JOINT RESEARCH AGREEMENT

This invention was made under a joint research agreement between International Business Machines Corporation and the Agency For Science, Technology and Research.

BACKGROUND

The present invention relates to composite hydrogels for delivery of biologically active materials, and more specifically to compositions comprising hydrogel forming triblock copolymers and drug loaded micelles of diblock copolymers.

One of the major problems in the development of anticancer drug formulations is the delivery of the drugs with adequately high bioavailability for therapeutic intention. As many anticancer agents are hydrophobic, clinical administration of these drugs typically requires dissolution using organic solvents. One such agent is paclitaxel, which is a widely used small molecular drug effective against an extensive range of solid tumors. However, its clinical applications have been mostly impeded by its extremely low aqueous solubility (0.3 micrograms/mL in water), which limits its administration to the use of a formulation comprising of 50:50 mixture of Cremophor EL (polyethoxylated castor oil): ethanol. Although this formulation is able to increase the solubility and bioavailability of paclitaxel (PTX), it can also lead to hypersensitivity reactions and other severe side effects in some cases. Despite premedication with corticosteroids to reduce the immune response, minor reactions such as rashes and flushing still occur in 41% to 44% of patients and potentially fatal reactions occur in 1.5% to 3% of patients. Thus, additional materials and methods are needed for administering hydrophobic drugs.

Hydrogels have emerged as an important class of materials for biomedical applications due to their unique properties that bridge the gap between solid and liquid states. Amongst the numerous classes of synthetic polymeric materials that are capable of forming hydrogels, ABA-type amphiphilic triblock copolymers have a hydrophilic central B block flanged on both the ends by peripheral hydrophobic A blocks. These materials are of interest because they can potentially form physical gels that do not involve the formation of covalent bonds. In some instances, the self-assembled morphology can change from independent micelles to a network of bridged micelles, and eventually to a hydrogel network at higher polymer concentration.

Owing to their non-toxicity and biocompatibility, poly (ethylene glycol) (PEG) has been used extensively as the non-ionic hydrophilic B block in hydrogel forming ABA triblock copolymers. Homo- or copolymers of poly(lactides) and poly(caprolactone) have been used for the hydrophobic A blocks. A drawback of the reported triblock copolymers is the high concentration and hydrophobic content needed for hydrogel formation. For example, gelation of an aqueous mixture of poly(L-lactide)-b-poly(ethylene glycol)-b-poly (L-lactide) (PLLA-b-PEG-b-PLLA) triblock copolymer occurs at a polymer concentration of about 16 wt % (weight percent) based on total weight of the aqueous mixture. The hydrophobic block content of the triblock copolymer was in a range of about 17 wt % to 37 wt % based on total weight of the triblock copolymer.

For many biomedical applications, it would be desirable to have polymeric materials that can form hydrogels at a lower concentration, which can be utilized for the delivery of biologically active substances that include hydrophobic drugs.

SUMMARY

Accordingly, a composite hydrogel is disclosed, comprising:

an amphiphilic triblock copolymer (ABA), wherein i) the triblock copolymer comprises two independent peripheral hydrophobic A blocks and a hydrophilic central B block, ii) each of the A blocks comprises a steroidal repeat unit (repeat unit 1) comprising both a backbone carbonate and a side chain comprising a steroid functional group, iii) each of the A blocks has a degree of polymerization of about 0.5 to about 4.0, and iv) the B block comprises a first poly(alkylene oxide) backbone; and a loaded micelle comprising a biologically active substance and an amphiphilic diblock copolymer (CD), wherein i) the diblock copolymer comprises a hydrophilic C block and a hydrophobic D block, ii) the C block comprises a second poly(alkylene oxide) backbone, and iii) the D block comprises a steroidal repeat unit (repeat unit 2) comprising both a backbone carbonate group and a side chain comprising a steroid functional group;

wherein the amphiphilic triblock copolymer and the loaded micelle are bound by noncovalent interactions, and the composite hydrogel is capable of controlled release of a biologically active substance.

Also disclosed is a method, comprising:

mixing an amphiphilic triblock copolymer (ABA) with a loaded micelle, the loaded micelle comprising i) a biologically active substance and ii) an amphiphilic diblock copolymer (CD), thereby forming a composite hydrogel capable of controlled release of the biologically active substance; wherein the triblock copolymer (ABA) comprises two independent peripheral hydrophobic A blocks and a hydrophilic central B block, wherein i) each of the A blocks comprises a steroidal repeat unit (repeat unit 1) comprising both a backbone carbonate and a side chain comprising a steroid functional group, ii) each of the A blocks has a degree of polymerization of about 0.5 to about 4.0, and iii) the B block comprises a first poly(alkylene oxide) backbone, the diblock copolymer (CD) comprises a hydrophilic C block and a hydrophobic D block, wherein i) the C block comprises a second poly(alkylene oxide) backbone, and ii) the D block comprises a steroidal repeat unit (repeat unit 2) comprising both a backbone carbonate and a side chain steroid functional group, and the triblock copolymer and the loaded micelle are bound by noncovalent interactions.

Further disclosed is a composite hydrogel for controlled release of a biologically active substance, comprising:

an amphiphilic triblock copolymer (ABA) having the structure:

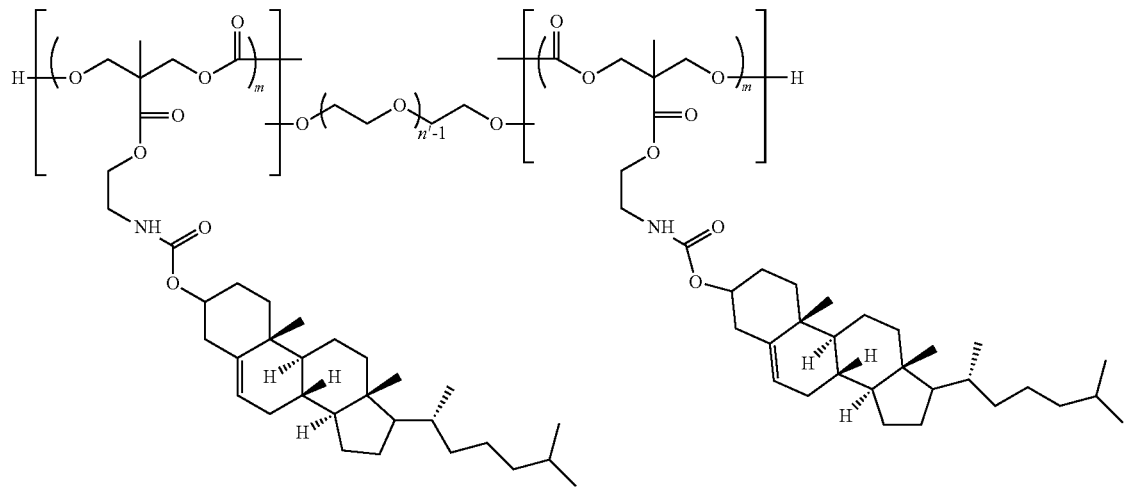

wherein each m is an independent number having a value of about 0.8 to about 2.5, and n' has a value of about 200 to about 800; and a loaded micelle comprising i) the biologically active substance and ii) an amphiphilic diblock copolymer (CD) having the structure:

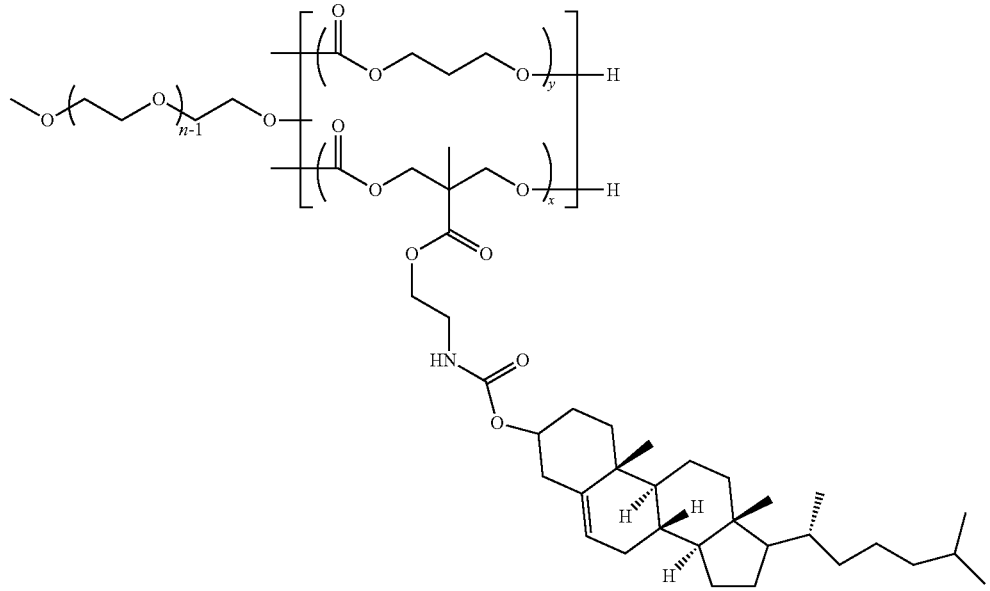

wherein n has a value of about 100 to about 120, x has a value of about 11, and y has a value of about 30, and wherein the amphiphilic triblock copolymer and the loaded micelle are bound by noncovalent interactions Also disclosed is a triblock copolymer having the formula (19)

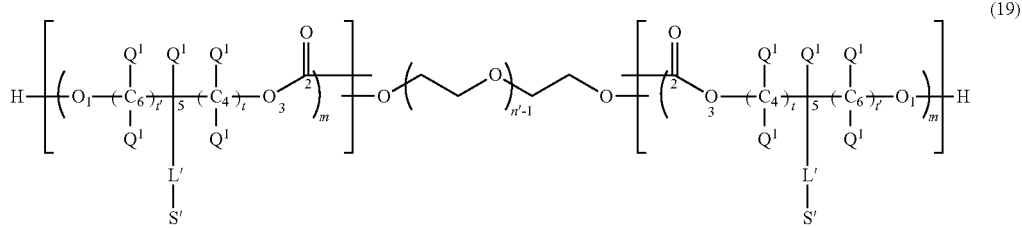

wherein
each m is an independent number having a value of about 0.8 to about 4,
n' has a value of about 200 to about 800,
each t is an independent integer having a value of 0 to 6,
each t' is an independent integer having a value of 0 to 6,
t' and t cannot both be zero in any repeat unit,
each $Q^1$ is an independent monovalent radical selected from the group consisting of hydrogen, halides, alkyl groups comprising 1 to 30 carbons, and aryl groups comprising 6 to 30 carbon atoms,
each L" is an independent linking group selected from the group consisting of a single bond and divalent radicals comprising 1 to 30 carbons, and
each S' is an independent steroid group.

The above-described and other features and advantages of the present invention will be appreciated and understood by those skilled in the art from the following detailed description, drawings, and appended claims.

DETAILED DESCRIPTION

Figure 1:
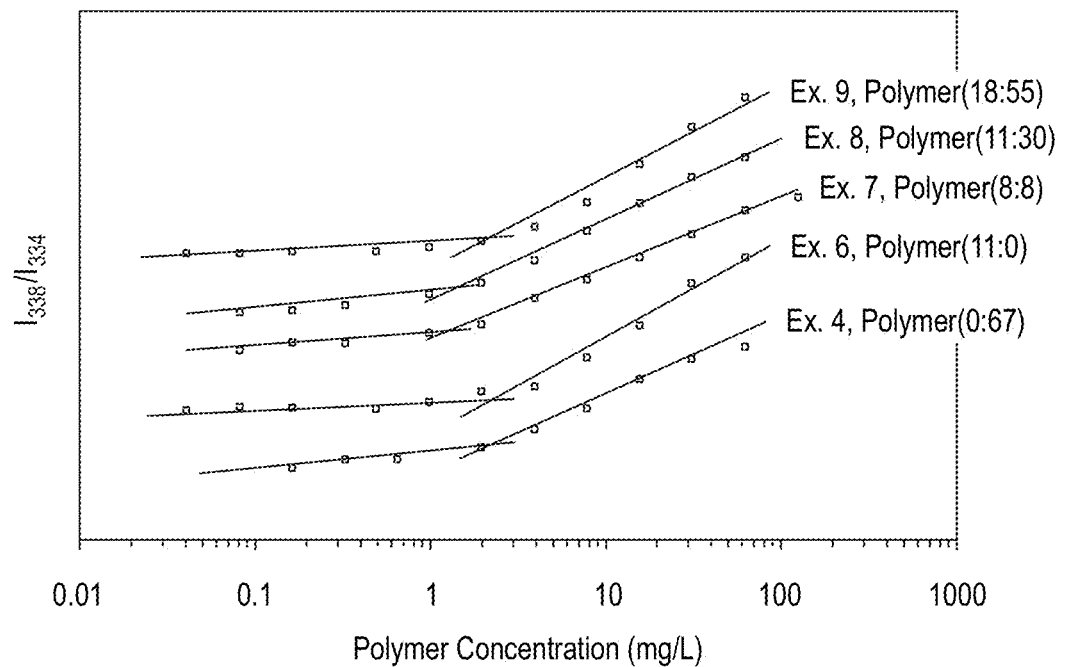
FIG. 1 is a graph showing the intensity ratio (1339/1334) versus logarithm of concentration (mg/L) of block copolymers (Examples 4, and 6 to 9), respectively, in deionized (DI) water. These data were used to determine critical micelle concentrations (CMC) values of Examples 4, and 6 to 9 of 2.1 mg/L, 2.1 mg/L, 1.5 mg/L, 1.5 mg/L and 2.1 mg/L, respectively (Table 8).

Composite hydrogels are disclosed that comprise an amphiphilic ABA triblock copolymer (ABA copolymer) and a loaded micelle, which are bound by non-covalent interactions. The triblock copolymer comprises a hydrophilic central B block, and two independent hydrophobic peripheral A blocks. The A blocks have a steroidal repeat unit comprising a steroid functionalized side chain and a backbone carbonate group. The central B block has a poly(alkylene oxide) backbone. The loaded micelle comprises an amphiphilic diblock copolymer (referred to as CD copolymer) and a biologically active substance, also bound by non-covalent interactions. The CD copolymer has a hydrophilic C block and a hydrophobic D block. The C block has a poly(alkylene oxide) backbone and the D block has a steroidal repeat unit comprising a steroid functionalized side chain and a carbonate backbone group. The steroidal repeat units of the A block and D block can be the same or different steroidal repeat units. To distinguish these steroidal repeat units in the following description, the steroidal repeat unit of the A block is referred to as repeat unit 1 and the steroidal repeat unit of the D block is referred to as the repeat unit 2. The A block and/or the D block can include additional repeat units having a carbonate and/or ester backbone functional groups. The examples further below demonstrate that the composite hydrogels comprising a micelle loaded with fluorescein isothiocyanate (FITC), which is used as a model for a drug, can release the FITC over a longer period compared to the loaded micelles alone. Thus, the composite hydrogels provide a straightforward and modular approach for the encapsulation and controlled release of biologically active materials for a variety of applications including but not limited to hydrophobic drug delivery, tissue engineering, and/or the design of cosmetics/food products additives. For instance, the composite hydrogels can be used to encapsulate molecules that can serve as active ingredients for cosmetic/dietary applications. These molecules can be small molecules such as vitamins or large biomolecules such as proteins. The ABA copolymer and CD copolymer are biodegradable and/or biocompatible.

The ABA copolymer has a low hydrophobic content, meaning repeat unit 1 of the A block is present in an amount of about 5 wt % to about 15 wt % based on total weight of the ABA copolymer. The ABA copolymer is not necessarily capable of forming a hydrogel alone in water. In some instances, the ABA copolymer is insoluble in water, but will form a hydrogel upon mixing with the loaded micelle. In instances when the ABA copolymer alone can form a hydrogel in water, the ABA hydrogel can form at an ABA copolymer concentration of about 4 wt %. The storage modulus (G') of the ABA hydrogel can be tuned from about 300 Pa to about 3500 Pa by varying the ABA copolymer composition and/or concentration.

The composite hydrogels can also form at a total solids content of about 4 wt % to about 8 wt % based on total weight of the aqueous mixture.

The ABA copolymer and CD copolymer are preferably derived from cyclic carbonate monomers comprising pendant steroid groups, referred to herein as steroidal monomers, which undergo organocatalyzed ring-opening polymerization (ROP). The resulting copolymers are functionalized with a side chain steroid group. The ring opening polymerization is initiated with a polymeric initiator comprising i) one or two nucleophilic initiator groups selected from the group consisting of alcohols, amines, thiols and combinations thereof, and ii) a poly(alkylene oxide) backbone.

For a given initiator, the amphiphilic properties of the block copolymers can be controlled by adjusting the amount and structure of the various repeat units in the ring opened polymer chain, that is, by adjusting the amount and structure of the cyclic carbonate monomer bearing a steroid group and/or the amount and structure of any diluent cyclic carbonyl monomer (cyclic carbonate and/or cyclic ester monomer(s)) used in the ring opening polymerization. The diluent cyclic carbonyl monomer does not comprise a steroid group. Thus, the hydrophobic A blocks and the hydrophobic D block can comprise a polycarbonate and/or polyestercarbonate chain bearing a side chain steroid group.

The ABA copolymer has a low critical micelle concentrations (CMC) in water. The CMC can have a value of 1.0 mg/L to 50 mg/L, 1.0 mg/L to 10 mg/L, and more particularly 1.0 mg/L to 2.5 mg/L.

The CD copolymer also has a low critical micelle concentrations (CMC) in water. The CMC can have a value of 1.0 mg/L to 50 mg/L, 1.0 mg/L to 10 mg/L, and more particularly 1.0 mg/L to 2.5 mg/L.

The CD copolymer is capable of forming reversible nanoparticulate complexes with hydrophobic biologically active substances (e.g., drugs and/or genes) by noncovalent interactions. For example, the CD copolymer can encapsulate the rigid hydrophobic anticancer drug paclitaxel (PTX) in the form of a water dispersible nano-sized particle (i.e., loaded micelle). Paclitaxel has the structure:

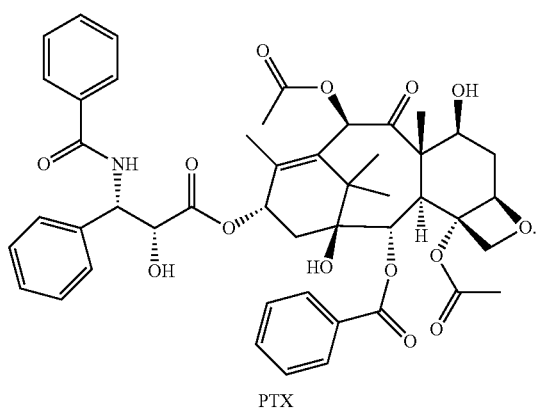 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

PTX

The loaded micelle forms without sonication or homogenization and has a narrow particle size distribution. The loaded micelle comprises PTX in an amount more than 0 wt %, and more particularly in an amount of 0.1 wt % to 15 wt % based on total dry weight of the loaded micelle. Other hydrophobic drugs that can be encapsulated by the amphiphilic block copolymers include cyclosporin A (CYC, an immunosuppressive agent used after organ transplantation) and spironolactone (SPL, a drug used to treat hypertension). The drugs can be used singularly or in combination. CYC and SPL have the structures (stereochemistry shown):

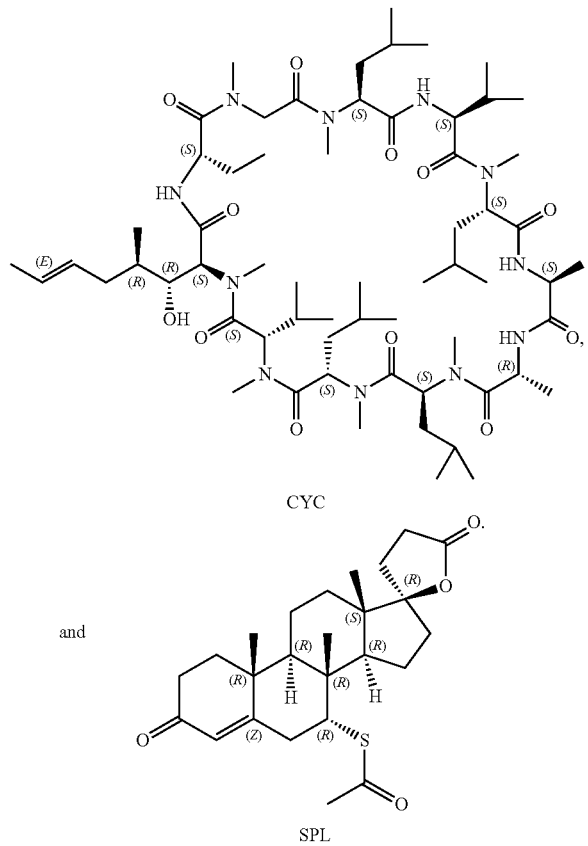

CYC and

SPL

In the following description, the term "cyclic carbonyl monomer" includes cyclic carbonate monomers, cyclic ester monomers, and combinations thereof that can be polymerized in a ring opening polymerization.

Herein, a cyclic carbonate monomer having a pendant steroid group is referred to as a "steroidal monomer." A second cyclic carbonyl monomer, referred to as a "diluent monomer," does not contain a steroid group. The diluent monomer can be a cyclic carbonate monomer, a cyclic ester (i.e., lactone, lactide) monomer, or a combination thereof. The steroidal monomer can be used singularly or in combination with one or more other steroidal monomers. The diluent monomer can be used singularly or in combination with one or more other diluent monomers.

A repeat unit having a pendant steroid group is referred to generally as a "steroidal repeat unit." Herein, a steroidal repeat unit has a carbonate backbone group. A repeat unit that does not contain a steroid group is referred to as a "diluent repeat unit." The diluent repeat unit can have a carbonate and/or ester backbone group.

In an embodiment, each of the two A blocks of the ABA copolymer consists essentially of repeat unit 1. The A blocks can independently have a degree of polymerization of about 0.5 to 10, more specifically 0.5 to 4, even more specifically 0.8 to 2.4 of repeat unit 1. It should be understood that the degree of polymerization represents an average value based on the proton nuclear magnetic resonance ($^1$H NMR) spectroscopy and/or SEC of the ABA copolymer.

Preferably, the hydrophobic D block of the CD copolymer comprises, in addition to repeat unit 1 having a side chain steroid group, a diluent repeat unit comprising a carbonate or ester backbone group.

In an embodiment, the ABA copolymer and CD copolymer comprise the same steroidal pendant group. In another embodiment, repeat unit 1 of the ABA copolymer is the same as repeat unit 2 of the CD copolymer.

The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

The steroidal monomer and the diluent monomer can be stereospecific or non-stereospecific. A stereospecific monomer or a stereospecific repeat unit i) has a non-superposable mirror image and ii) comprises one or more asymmetric tetravalent carbons (i.e., tetrahedral sp$^3$ carbons). Each asymmetric tetravalent carbon is assigned an R or S symmetry based on Cahn-Ingold-Prelog (CIP) symmetry rules. For example, if a stereospecific repeat unit has one asymmetric tetravalent carbon, then the stereospecific repeat unit can be present substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific repeat unit can be present substantially as the R,R stereoisomer, substantially as the R,S stereoisomer, substantially as the S,S stereoisomer, or substantially as the S,R stereoisomer.

A stereospecific cyclic carbonyl monomer i) has a non-superposable mirror image and ii) comprises one or more asymmetric tetravalent carbons. The stereospecific cyclic carbonyl monomer has a stereoisomeric purity of 90% or more, and more particularly 98% or more. The asymmetric tetravalent carbons of the stereospecific cyclic carbonyl monomer can be in the steroid group or in a ring carbon that becomes a polymer backbone carbon in the ring opening polymerization.

"Restricted metals" herein include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Each one of the foregoing restricted metals can have a concentration in the block copolymer of 0 parts to 100 ppm (parts per million), 0 parts to 100 ppb (parts per billion), or 0 parts to 100 ppt (parts per trillion). Preferably, each one of the foregoing restricted metals has a concentration of 0 parts in the ABA and CD copolymers (i.e., the concentration is below detection limits). In an embodiment, the chemical formulas of the components used in the ring opening polymerization, including the steroidal monomer, the diluent monomer, the polymeric initiator, the catalyst for the ring opening polymerization, the solvent, and any base accelerator, contain none of the above restricted metals. The biologically active cargo material can comprise a restricted metal.

No restriction is placed on the concentration of boron, silicon, or any individual alkali metal in the ABA and CD copolymers.

The term "carrier" as used herein refers to the combination of the ABA and CD copolymers. The carrier can be biologically active when used alone (e.g., as a result of enzymatic release of the covalently bound steroid group, where the released steroid performs a therapeutic function). The composite hydrogel can therefore serve one or more biological functions, including providing enhanced biological activity of either the released steroid and/or the released biologically active substance (i.e., cargo material). As an example, upon contacting a tissue (e.g., wound surface) or cell, the composite hydrogel can release the biologically active substance and/or the steroid at separate rates and times over a desired period. Alternatively or additionally, the composite hydrogel can enter a tissue or a cell (e.g., by endocytosis), and at a desired stage release the biologically active substance and/or the steroid within the tissue or the cell.

The biologically active substance can be any suitable biologically active substance that complexes with the CD copolymer in water by non-covalent interactions to form a loaded micelle. Biologically active substances include cells, biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing. In an embodiment, the biologically active substance is a drug and/or a gene.

"Biologically active" means the referenced material can alter the chemical structure and/or activity of a cell in a desirable manner, or can selectively alter the chemical structure and/or activity of a cell type relative to another cell type in a desirable manner. As an example, one desirable change in a chemical structure can be the incorporation of a gene into the DNA of the cell. A desirable change in activity can be the expression of the transfected gene. Another change in cell activity can be the induced production of a desired hormone or enzyme. Alternatively, a desirable change in activity can be the selective death of one cell type over another cell type. No limitation is placed on the relative change in cellular activity caused by the biologically active substance, providing the change is desirable and useful. Moreover, no limitation is placed on the cargo, providing the cargo induces a useful cellular response when released from the composite hydrogel.

The steroidal monomer is a cyclic carbonate monomer comprising a pendant steroid group. The steroid group can be a chemical moiety derived from a naturally occurring human steroid, non-human steroid, and/or synthetic steroid compound. Herein, a steroid group comprises a tetracyclic ring structure according to formula (1):

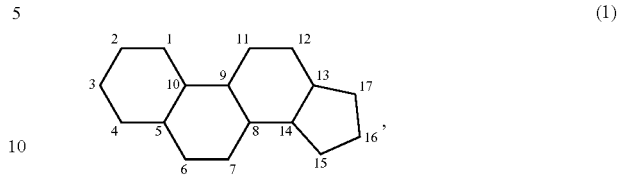

wherein the 17 carbons of the ring system are numbered as shown. Each ring of the tetracyclic ring structure can independently comprise one or more double bonds. The steroid group can comprise one or more substituent groups independently comprising 0 to 30 carbons attached to one or more of the numbered ring positions of the tetracyclic ring structure.

The steroidal monomer comprises a cyclic carbonate ring that is joined to a steroid group by a divalent linking group L'. The steroidal monomer has the formula (2):

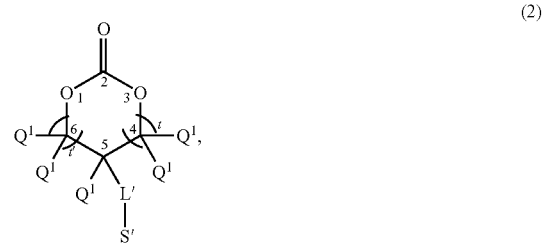

wherein t and t' are independent integers having a value of 0 to 6, wherein t' and t cannot both be zero, and each $Q^1$ is a monovalent radical independently selected from the group consisting of hydrogen, halides, alkyl groups comprising 1 to 30 carbons, and aryl groups comprising 6 to 30 carbon atoms. Ring carbons and oxygens are numbered as shown in formula (2). L' is a divalent linking group comprising one or more carbons. S' is a steroid group. The L'-S' bond is preferably hydrolytically cleavable and/or enzymatically cleavable, meaning the bond can be directly or indirectly cleaved as a result of enzymatic activity. Each $Q^1$ group can independently be branched or non-branched. Each $Q^1$ group can also independently comprise one or more additional functional groups selected from the group consisting of ketones, aldehydes, alkenes, alkynes, cycloaliphatic rings comprising 3 to 10 carbons, heterocylic rings comprising 2 to 10 carbons, ethers, amides, esters, and combinations of the foregoing functional groups. A heterocyclic ring can comprise oxygen, sulfur and/or nitrogen. Two or more $Q^1$ groups can together form a ring. The steroidal monomer can be stereospecific or non-stereospecific. In an embodiment, t and t' are each 1, each $Q^1$ at carbon 4 is hydrogen, each $Q^1$ at carbon 6 is hydrogen, and $Q^1$ at carbon 5 is selected from the group consisting of hydrogen, methyl, and ethyl. In another embodiment, S' is a cholesteryl group.

L' can comprise one or more functional groups selected from the group consisting of ketone, ester, amide, imide, thioester, carbamate, thiocarbamate (i.e., —S—C═O(N(R)—), urea, anhydride, and combinations thereof. In an embodiment, L' comprises a carbonyl group linked to S'. In another embodiment, L' comprises an amidocarbonyl group:

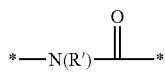

wherein R' is hydrogen or a monovalent radical comprising 1 to 5 carbons, and the carbonyl group of the amidocarbonyl group is linked to S'.

Exemplary steroid groups S' include but are not limited to stereospecific structures such as:

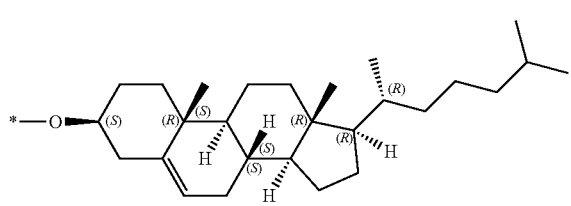

from cholesterol and referred to herein as a cholesteryl group,

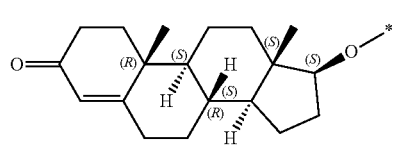

from testosterone,

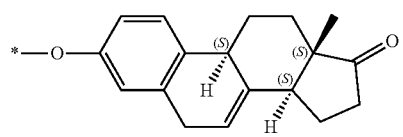

from equilin,

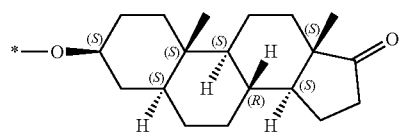

from epiandrosterone,

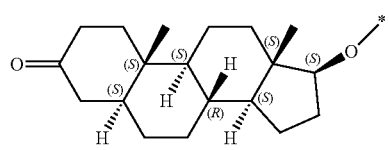

from dihydrotestosterone,

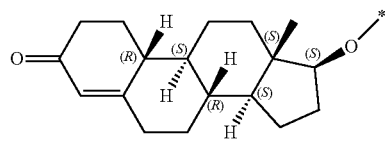

from nandrolone,

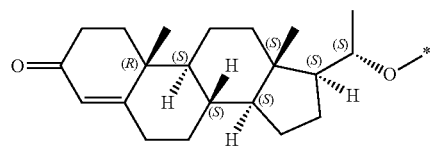

from dihydroprogesterone,

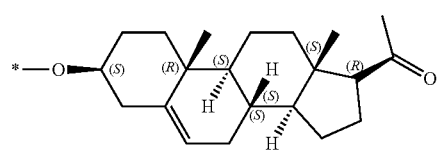

from pregnenolone,

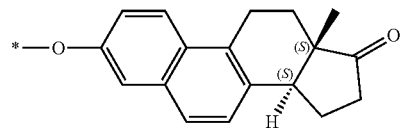

from equilenin,

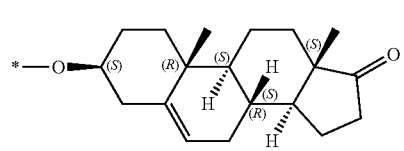

from dehydroepiandrosterone,

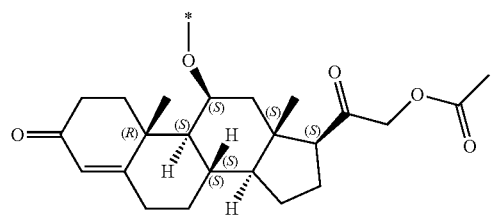

from corticosterone acetate,

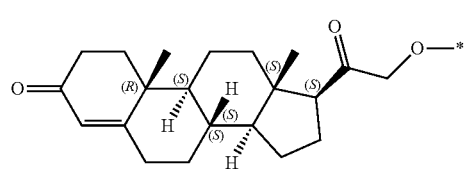

from deoxycorticosterone, and

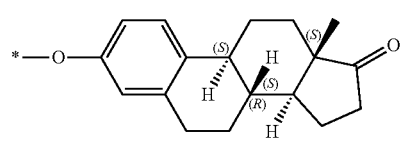

from estrone.

In the above steroid groups, the starred bond represents the attachment point to L'. The R,S stereochemistry of each asymmetric tetravalent carbon is indicated in the above steroid groups. Other steroid groups include various stereoisomers of the foregoing steroid groups. The steroid groups can be used in combination, meaning two or more steroidal monomers differing in chemical structure and/or in stereospecificity can be used to form the polycarbonate block of the amphiphilic block copolymer.

Ring opening polymerization of the steroidal monomer of formula (2) produces a steroidal repeat unit having the formula (3):

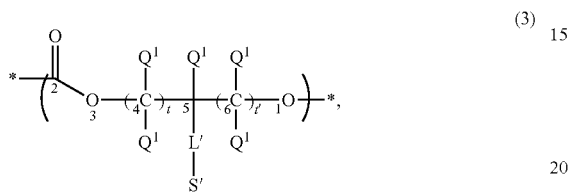

(3)

wherein L', t, t', $Q^1$, and S' are defined as above. Atom numbers of the backbone carbons and oxygens are indicated in formula (3). The steroidal repeat unit comprises a backbone carbonate group. The starred bonds in formula (3) represent attachment points to other subunits or to a terminal functional group of the ROP polymer chain.

More specific steroidal monomers include cyclic carbonate compounds of formula (4):

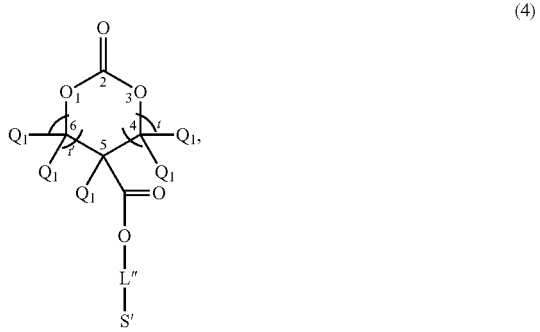

(4)

wherein t, t', $Q^1$, and S' are defined as above. L" can be a single bond (i.e., S' is linked to the ester oxygen of formula (4) by a single bond). Alternatively, L" can be a divalent linking group comprising 1 to 30 carbons. The L"-S' bond can be a hydrolytically and/or enzymatically cleavable bond.

Ring opening polymerization of the steroidal monomer of formula (4) produces a steroidal repeat unit having the formula (5):

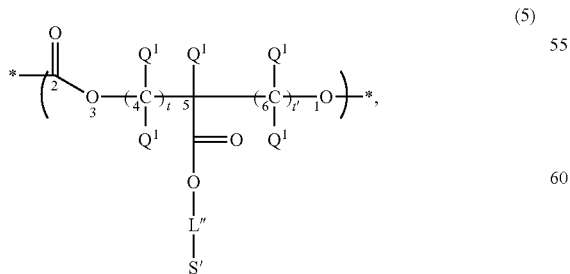

(5)

wherein L", t, t', $Q^1$, and S' are defined as above, and backbone carbons and oxygens are numbered as indicated. The steroidal repeat unit comprises a backbone carbonate group.

More specific steroidal monomers of formula (2) include cholesteryl monomers of formula (6):

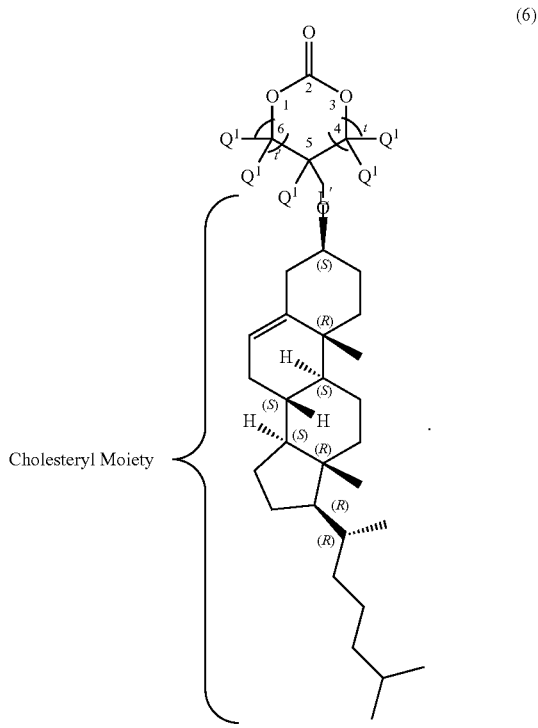

(6)

wherein L', t, t' and $Q^1$ are defined as in formula (2). The R,S stereochemistry of each asymmetric tetravalent carbon center of the cholesteryl moiety is indicated in formula (6). In an embodiment, the L'-0 bond in formula (6) is hydrolytically and/or enzymatically cleavable.

The steroidal repeat unit formed by a ring opening polymerization of the cholesteryl monomer of formula (6) has the formula (7):

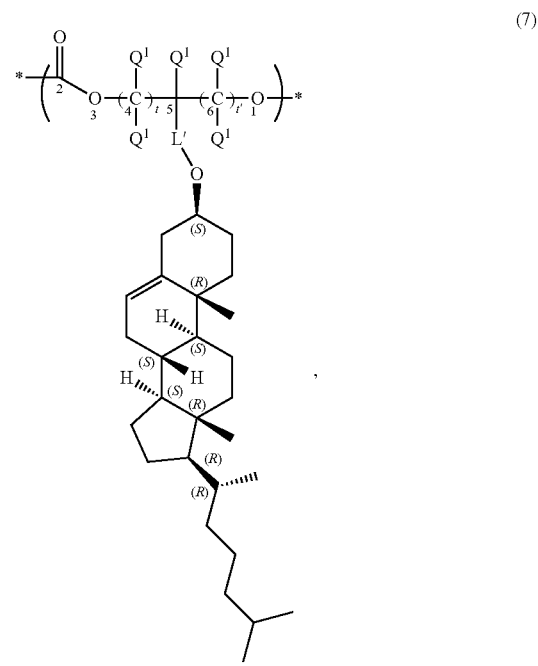

(7)

wherein L', t, t', and $Q^1$ are defined as in formula (2), and backbone carbons and oxygens are numbered as shown. The R,S stereochemistry of each asymmetric tetravalent carbon center of the cholesteryl moiety is indicated in formula (7). The steroidal repeat unit of formula (7) comprises a backbone carbonate group.

More specific steroidal monomers of formula (4) include cholesteryl monomers of formula (8):

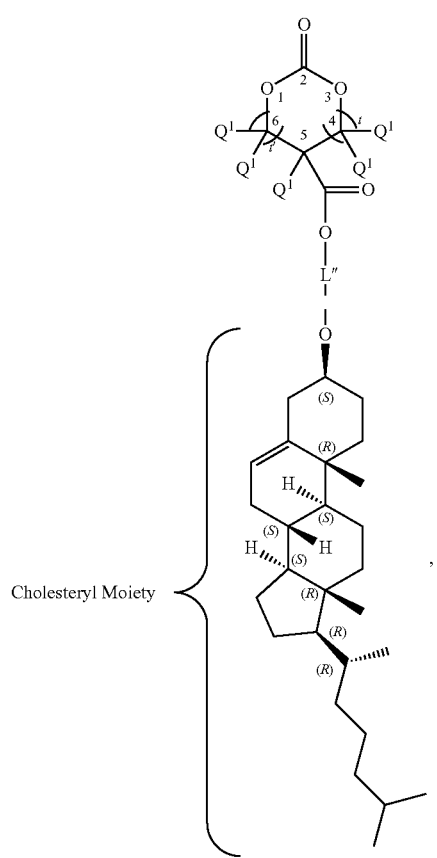

(8)

with R,S stereochemistry shown, wherein L" is defined as above under formula (4), and t, t', and $Q^1$ are defined as above under formula (2).

The steroidal repeat unit formed by ring opening polymerization of the cholesteryl monomer of formula (8) has the formula (9):

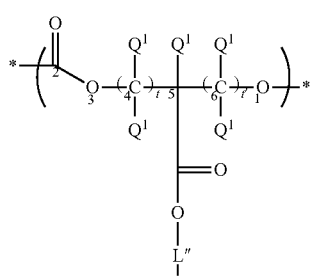

(9)

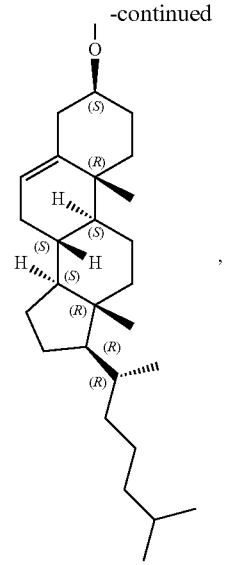

with R,S stereochemistry shown, wherein L", t, t', and $Q^1$ are defined as above, and backbone carbons and oxygens are numbered as shown. The steroidal repeat unit of formula (9) comprises a backbone carbonate group.

In an embodiment, L' has a structure according to formula (10):

(10)

wherein L'" is a divalent linking group comprising 1 to 20 carbons. L'" can comprise one or more heteroatoms selected from the group consisting of oxygen, nitrogen, sulfur, and combinations thereof. In an embodiment L'" has the formula *—O—$CH_2(CH_2)_xCH_2N(R)$—*, wherein x is an integer of 1 to 10 and R' is an monovalent alkyl group having 1 to 5 carbons:

The diluent monomer, which forms a diluent repeat unit of the ROP polymer chain, can be selected from cyclic carbonate compounds of the formula (11):

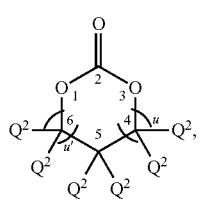

(11)

wherein u and u' are independent integers having a value of 0 to 6 wherein u and u' cannot both be zero, and each $Q^2$ is a monovalent radical independently selected from the group consisting of hydrogen, halides, alkyl groups comprising 1 to 30 carbons, and aryl groups comprising 6 to 30 carbon atoms. Ring carbons and oxygens are numbered as shown in formula (11). No $Q^2$ group comprises a steroid group. Each $Q^2$ group can independently be branched or non-branched. Each $Q^2$ group can independently be stereospecific or non-stereospecific. Each $Q^2$ group can independently comprise one or more additional functional groups selected from the group consisting of ketones, aldehydes, alkenes, alkynes, ethers, amides, esters, cycloaliphatic rings comprising 3 to 10 carbons, heterocylic rings comprising 2 to 10 carbons, and combinations of the foregoing functional groups. A heterocyclic ring can comprise oxygen, sulfur and/or nitrogen. Two or more $Q^2$ groups can together form a ring. In an embodiment, u' and u are each 1, and each $Q^2$ is hydrogen (i.e., trimethylene carbonate).

The diluent repeat unit formed by ring opening polymerization of the diluent monomer of formula (11) has the formula (12):

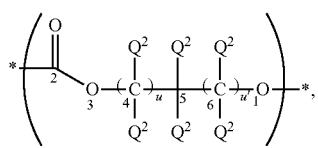
(12)

wherein u, u', and $Q^2$ are defined as above under formula (11), and backbone carbons and oxygens are numbered as shown. In this instance, the diluent repeat unit comprises a backbone carbonate group.

More specific diluent monomers of formula (11) have the formula (13):

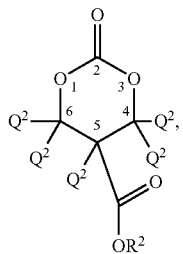
(13)

wherein $Q^2$ is defined as above under formula (11), $R^2$ is a monovalent radical independently selected from the group consisting of alkyl groups comprising 1 to 30 carbons and aryl groups comprising 6 to 30 carbons, and $R^2$ does not comprise a steroid group.

The diluent repeat unit formed by ring opening polymerization of the diluent monomer of formula (13) has the formula (14):

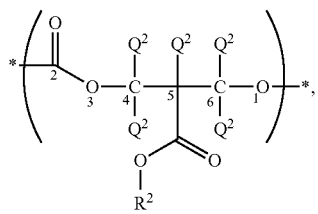
(14)

wherein $Q^2$ and $R^2$ are defined as above, and backbone carbons and oxygens are numbered as shown. This diluent repeat unit also comprises a backbone carbonate group.

The diluent monomer can be selected from cyclic ester monomers (e.g., lactones). Exemplary cyclic ester monomers include compounds of the formula (15):

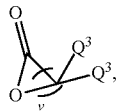
(15)

wherein v is an integer of 1 to 8, each $Q^3$ is a monovalent radical independently selected from the group consisting of hydrogen, halides, alkyl groups comprising 1 to 30 carbons, and aryl groups comprising 6 to 30 carbon atoms. No $Q^3$ group comprises a steroid group. The cyclic ester ring can optionally comprise a carbon-carbon double bond; that is, optionally, a

group of formula (15) can independently represent a

group. The cyclic ester ring can also comprise a heteroatom such as oxygen, nitrogen, sulfur, or a combination thereof; that is, optionally a

group of formula (15) can independently represent a *—O—*, *—S—*, *—N(H)—*, or an *—N($R^1$)—* group, wherein $R^1$ is a monovalent radical independently selected from the group consisting of alkyl groups comprising 1 to 30 carbons and aryl groups comprising 6 to 30 carbons. Cyclic ester monomers of formula (15) can be stereospecific or non-stereospecific.

The diluent repeat unit formed by ring opening polymerization of the diluent monomer of formula (15) has the formula (16):

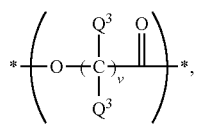
(16)

wherein $Q^3$ and v are defined as above under formula (15). This diluent repeat unit comprises a backbone ester group.

Herein, a ring opened polymer chain that has only backbone carbonate groups is a polycarbonate. A ring opened polymer chain that has backbone carbonate groups and backbone ester groups is referred to as a polyestercarbonate.

The diluent monomer can be selected from a dioxane dicarbonyl monomers of the formula (17):

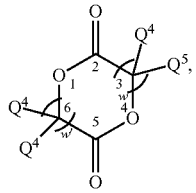

(17)

wherein w and w' are independent integers having a value of 1 to 3, and each $Q^4$ and each $Q^5$ is a monovalent radical independently selected from the group consisting of hydrogen, halides, alkyl groups comprising 1 to 30 carbons, and aryl groups comprising 6 to 30 carbon atoms. No $Q^4$ group and no $Q^5$ group comprises a steroid group. Compounds of formula (17) can be stereospecific or non-stereospecific. In an embodiment, w and w' are each 1, each $Q^4$ is hydrogen, and each $Q^5$ is an alkyl group comprising 1 to 6 carbons. In another embodiment, the diluent monomer is D-lactide or L-lactide.

The diluent repeat unit formed by ring opening polymerization of the diluent monomer of formula (17) has the formula (18):

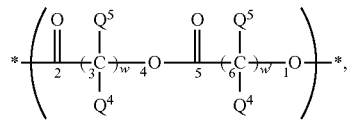

(18)

wherein $Q^4$, $Q^5$, w, and w' are defined as above under formula (17), and backbone carbons and oxygens are numbered as shown.

Non-limiting examples of diluent monomers of formulas (11) and (13) include the cyclic carbonate monomers of Table 1.

TABLE 1

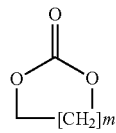

m = 1: Trimethylene carbonate (TMC)
m = 2: Tetramethylene carbonate (TEMC)
m = 3: Pentamethylene carbonate (PMC)

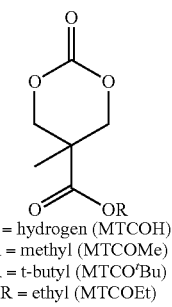

R = hydrogen (MTCOH)
R = methyl (MTCOMe)
R = t-butyl (MTCO$^t$Bu)
R = ethyl (MTCOEt)

TABLE 1-continued

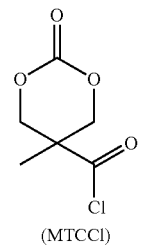

(MTCCl)

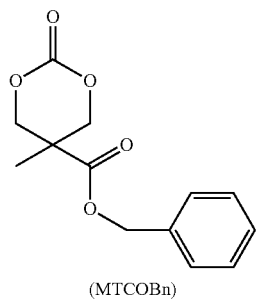

(MTCOBn)

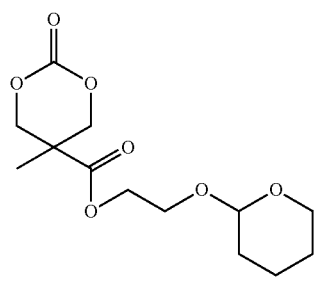 [SMILES: CC1(C(=O)OCCOC2CCCCO2)COC(=O)OC1]

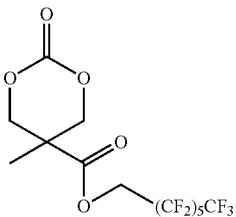

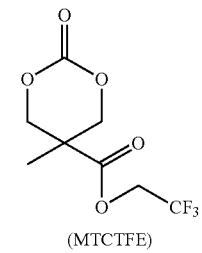

(MTCTFE)

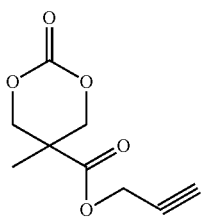

TABLE 1-continued
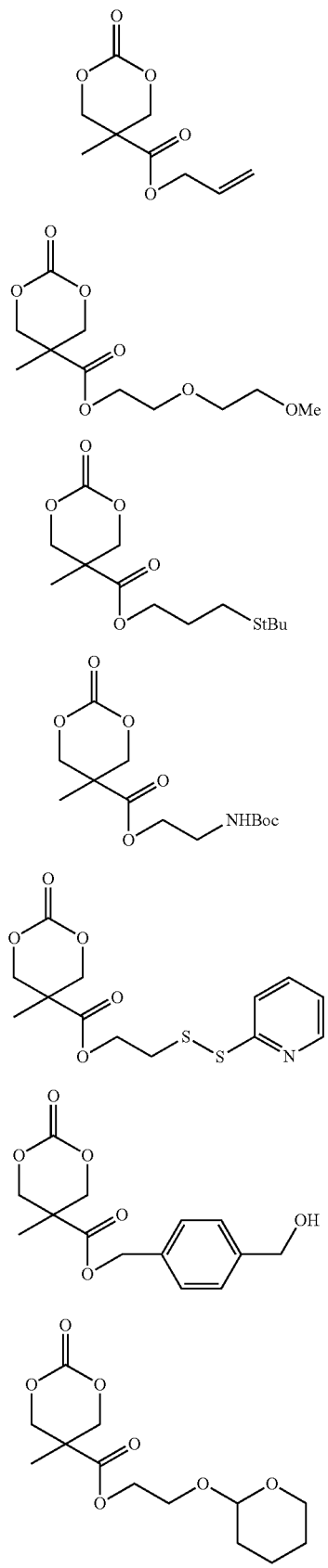
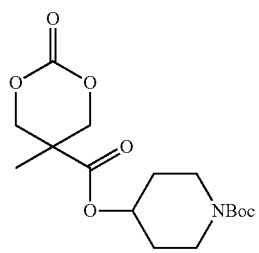 [SMILES: CC(C)(C)OC(=O)N1CCC(OC(=O)C2(C)COC(=O)OC2)CC1]
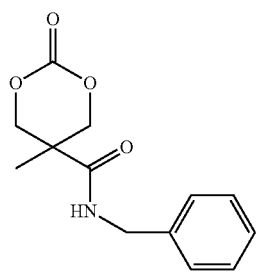 [SMILES: CC1(C(=O)NCc2ccccc2)COC(=O)OC1]
R = methyl
R = iso-propyl
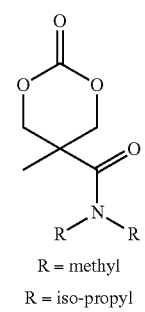
(MTCOEE)
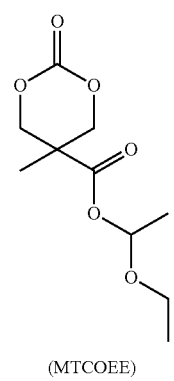
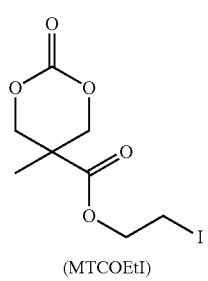
(MTCOEtI)

TABLE 1-continued

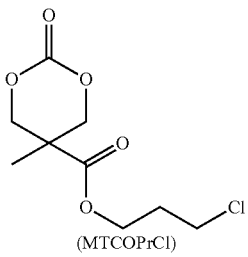
(MTCOPrCl)

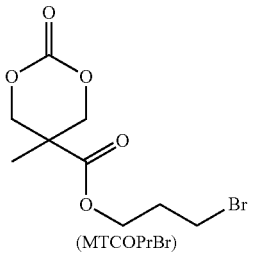
(MTCOPrBr)

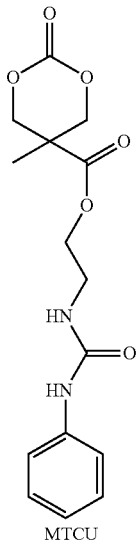
MTCU

Non-limiting examples of diluent monomers having a cyclic ester structure of formula (15) include the compounds of Table 2, and stereospecific versions thereof where feasible.

TABLE 2

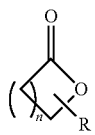

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH$_3$; n = 1: beta-Butyrolactone (b-BL)
R = CH$_3$; n = 2: gamma-Valerolactone (g-VL)

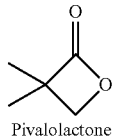
Pivalolactone

TABLE 2-continued (PVL)

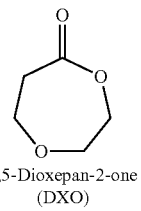
1,5-Dioxepan-2-one
(DXO)

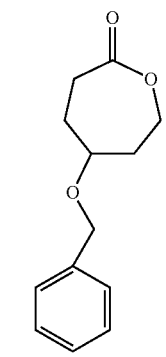 [SMILES: O=C1CCC(OCc2ccccc2)CCO1]
5-(Benzyloxy)oxepan-2-one
(BXO)

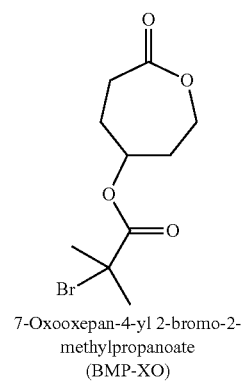
7-Oxooxepan-4-yl 2-bromo-2-methylpropanoate
(BMP-XO)

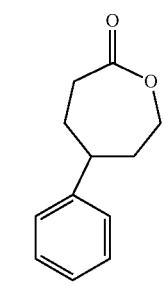 [SMILES: O=C1CCC(c2ccccc2)CCO1]
5-Phenyloxepan-2-one
(PXO)

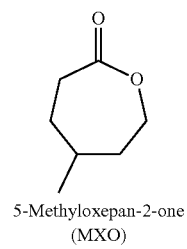
5-Methyloxepan-2-one
(MXO)

TABLE 2-continued

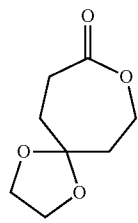 [SMILES: O=C1CCC2(CCO1)OCCO2]

1,4,8-Trioxa(4,6)spiro-9-undecane
(TOSUO)

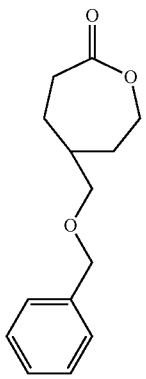 [SMILES: O=C1CCC(COCc2ccccc2)CCO1]

5-(Benzyloxymethyl)oxepan-2-one (BOMXO)

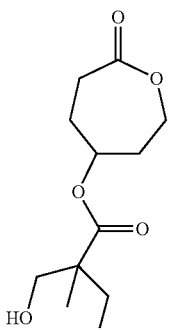

7-Oxooxepan-4-yl 3-hydroxy-2-
(hydroxymethyl)-2-methylpropanoate
(OX-BHMP)

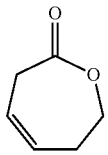

(Z)-6,7-Dihydrooxepin-2(3H)-one (DHXO)

Examples of diluent monomers of formula (17) include the compounds of Table 3.

TABLE 3

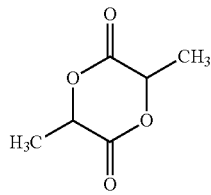

D-Lactide (DLA),
L-Lactide (LLA), or
racemic Lactide,
1:1 D:L forms (DLLA)

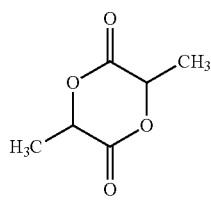

meso-Lactide (MLA)
(two opposite centers of asymmetry,
R and S)

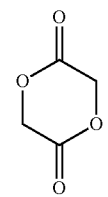

Glycolide (GLY)

The above monomers can be purified by recrystallization from a solvent such as ethyl acetate or by other known methods of purification, with particular attention being paid to removing as much water as possible from the monomer. The monomer moisture content can have a value of 1 to 10,000 ppm, 1 to 1,000 ppm, 1 to 500 ppm, and most specifically 1 to 100 ppm, by weight of the monomer.

In an embodiment, the ABA triblock copolymer has a structure according to formula (19):

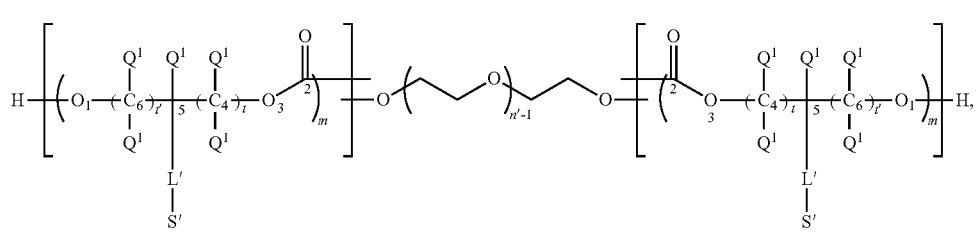

(19)

wherein
  each m is an independent number having a value of about 0.8 to about 4,
  n' has a value of about 200 to about 800,
  each t is an independent integer having a value of 0 to 6,
  each t' is an independent integer having a value of 0 to 6,
  t' and t cannot both be zero in any repeat unit,
  each $Q^1$ is an independent monovalent radical selected from the group consisting of hydrogen, halides, alkyl groups comprising 1 to 30 carbons, and aryl groups comprising 6 to 30 carbon atoms,
  each L' is an independent linking group selected from the group consisting of a single bond and divalent radicals comprising 1 to 30 carbons, and
  each S' is an independent steroid group.

In another embodiment, the ABA triblock copolymer has a structure according to formula (20):

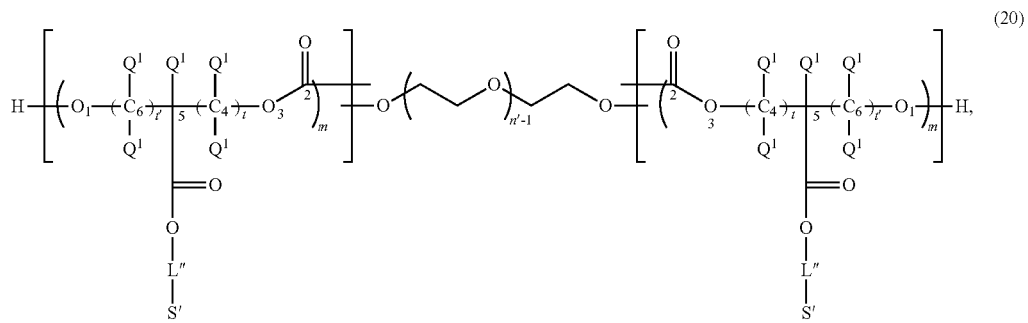

(20)

wherein
  each m is an independent number having a value of about 0.8 to about 4,
  n' has a value of about 200 to about 800,
  each t is an independent integer having a value of 0 to 6,
  each t' is an independent integer having a value of 0 to 6,
  t' and t cannot both be zero in any repeat unit,
  each $Q^1$ is an independent monovalent radical selected from the group consisting of hydrogen, halides, alkyl groups comprising 1 to 30 carbons, and aryl groups comprising 6 to 30 carbon atoms,
  each L" is an independent linking group selected from the group consisting of a single bond and divalent radicals comprising 1 to 30 carbons, and
  each S' is an independent steroid group.

More specifically, the ABA triblock copolymer can have a structure according to formula (21):

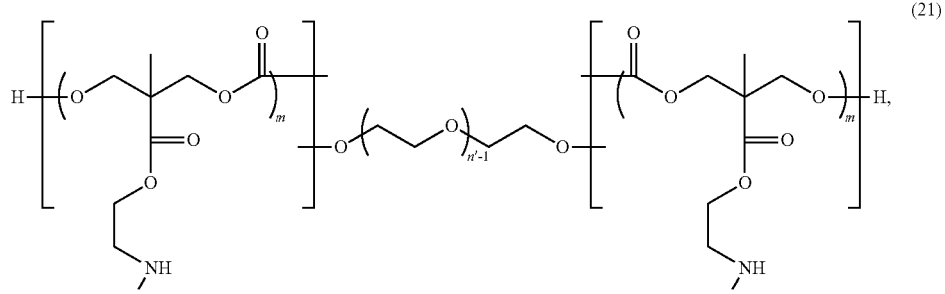

(21)

31

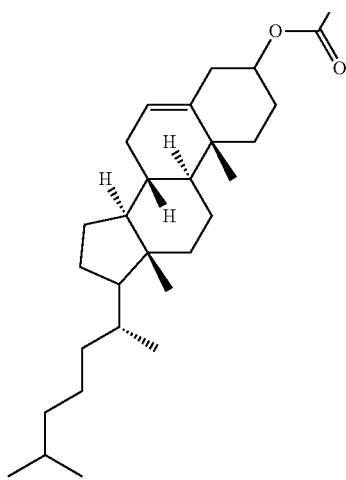

32

-continued

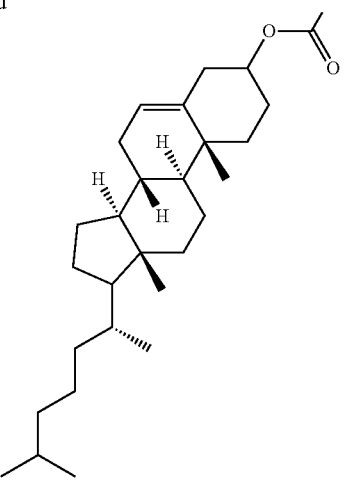

wherein each m is an independent number having a value of about 0.8 to about 4.0, and n' has a value of about 200 to about 800.

ROP Initiators

In general, initiators for ring opening polymerizations include nucleophilic groups such as alcohols, primary amines, secondary amines, and thiols. The ABA copolymer is preferably formed using a dinucleophilic poly(alkylene glycol) initiator (e.g., poly(ethylene glycol) (PEG)), and the CD copolymer is preferably formed using a mono-endcapped mono-nucleophilic poly(alkylene glycol) initiator (e.g., mono-methyl poly(ethylene glycol) (mPEG-OH)). The ABA copolymer derived from PEG has a central B block comprising a poly(ethylene oxide) chain linked at each end to an A block. The CD copolymer derived from mPEG-OH has a C block comprising a mono-endcapped poly(ethylene oxide) chain linked at one end to the D block.

The polymeric initiator can comprise a nucleophilic chain end group independently selected from the group consisting alcohols, primary amines, secondary amines, and thiols, such as mono-endcapped PEG-diamine represented by the structure

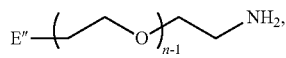

wherein E" represents a derivative of a terminal aminoethylene group, and monoendcapped PEG-dithiol, represented by the formula (22):

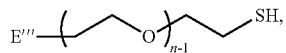

(22)

wherein E''' represents a derivative of a terminal thioethylene group.

The number average molecular weight (Mn) of the mono-nucleophilic polyether initiator can have a value of 100 to 100,000, more preferably 100 to 10000, and even more preferably 100 to 5000.

Ring Opening Polymerizations (ROP)

The following description of methods, conditions and materials for ring opening polymerizations is applicable to the preparation of the block copolymer.

The ring-opening polymerization can be performed at a temperature that is about ambient temperature or higher, more specifically 15° C. to 200° C., and even more specifically 20° C. to 80° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

The ROP reaction can be performed with or without the use of a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable monomer concentration is about 0.1 to 5 moles per liter, and more particularly about 0.2 to 4 moles per liter.

Whether performed in solution or in bulk, the ROP polymerizations are conducted under an inert (i.e., dry) atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

Less preferred catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate, and zirconium nitrate.

Preferred catalysts are organocatalysts whose chemical formulas contain none of the restricted metals described further above. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

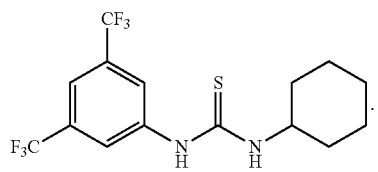
(TU)

Other ROP organocatalysts comprise at least one 1,1,1,3,3,3-hexafluoropropan-2-ol-2-yl (HFP) group. Singly-donating hydrogen bond catalysts have the formula (23):

$$R^2\text{—}C(CF_3)_2OH \tag{23}$$

wherein $R^2$ represents a hydrogen or a monovalent radical having 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 4.

TABLE 4

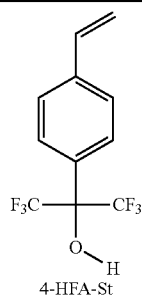
4-HFA-St

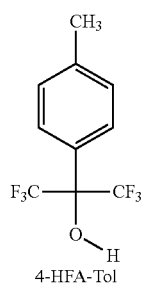
4-HFA-Tol

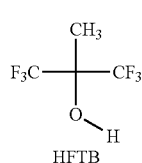
HFTB

TABLE 4-continued

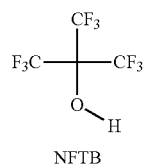
NFTB

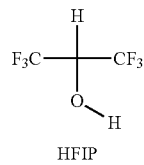
HFIP

Doubly-donating hydrogen bonding catalysts have two HFP groups, represented by the formula (24):

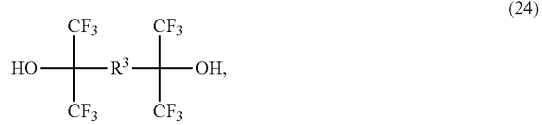
(24)

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (24) include those listed in Table 5. In a specific embodiment, $R^2$ is an arylene or substituted arylene group, and the HFP groups occupy positions meta to each other on the aromatic ring.

TABLE 5

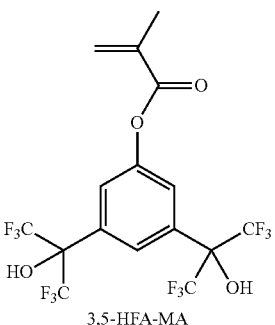
3,5-HFA-MA

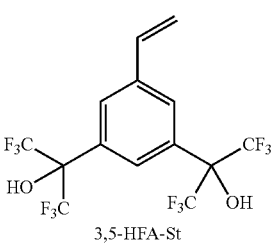
3,5-HFA-St

TABLE 5-continued

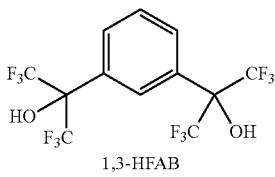
1,3-HFAB

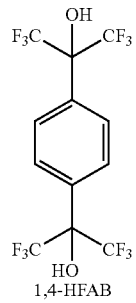
1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators

The ROP polymerization can be conducted in the presence of an optional accelerator, in particular a nitrogen base. Exemplary nitrogen base accelerators are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0] dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-1-propylphenyl(imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 6.

TABLE 6

Pyridine
(Py)

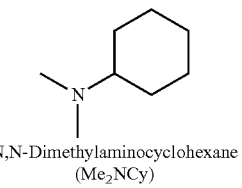
N,N-Dimethylaminocyclohexane
(Me$_2$NCy)

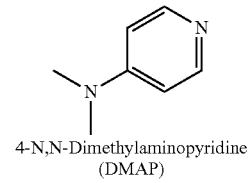
4-N,N-Dimethylaminopyridine
(DMAP)

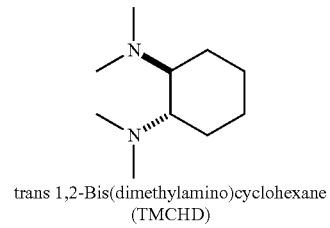
trans 1,2-Bis(dimethylamino)cyclohexane
(TMCHD)

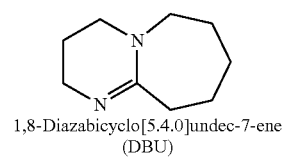
1,8-Diazabicyclo[5.4.0]undec-7-ene
(DBU)

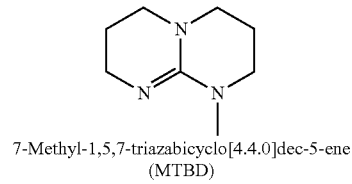
7-Methyl-1,5,7-triazabicyclo[4.4.0]dec-5-ene
(MTBD)

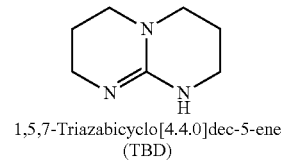
1,5,7-Triazabicyclo[4.4.0]dec-5-ene
(TBD)

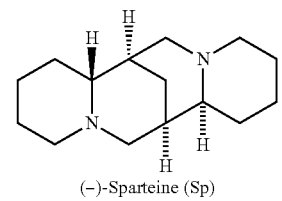
(−)-Sparteine (Sp)

TABLE 6-continued

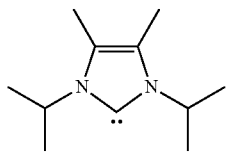

1,3-Bis(2-propyl)-4,5-dimethylimidazol-2-ylidene
(Im-1)

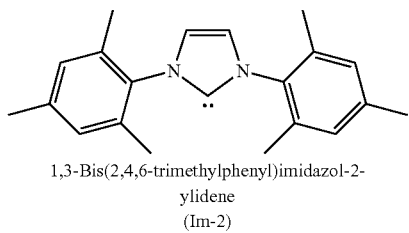

1,3-Bis(2,4,6-trimethylphenyl)imidazol-2-ylidene
(Im-2)

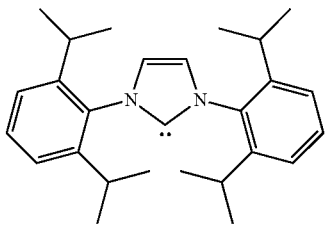

1,3-Bis(2,6-di-i-propylphenyl(imidazol-2-ylidene
(Im-3)

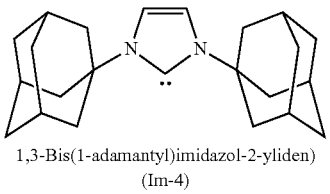

1,3-Bis(1-adamantyl)imidazol-2-yliden)
(Im-4)

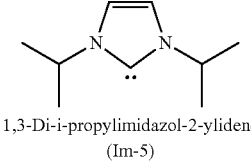

1,3-Di-i-propylimidazol-2-ylidene
(Im-5)

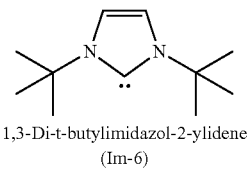

1,3-Di-t-butylimidazol-2-ylidene
(Im-6)

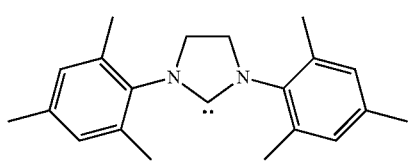

1,3-Bis(2,4,6-trimethylpheny1)-4,5-dihydroimidazol-2-ylidene
(Im-7)

TABLE 6-continued

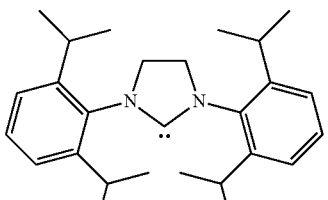

1,3-Bis(2,6-di-i-propylphenyl)-4,5-dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per nucleophilic initiator group. The initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of cyclic carbonyl monomer, the amount of initiator is 0.05× 50=2.5 g per mole of cyclic carbonyl monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on the equivalent molecular weight per nucleophilic initiator group of the initiator.

The catalysts can be removed by selective precipitation or in the case of the solid supported catalysts, simply by filtration. The block copolymer can comprise residual catalyst in an amount greater than 0 wt % (weight percent), based on total weight of the block copolymer and the residual catalyst. The amount of residual catalyst can also be less than 20 wt %, less than 15 wt %, less than 10 wt %, less than 5 wt %, less than 1 wt %, or most specifically less than 0.5 wt % based on the total weight of the block copolymer and the residual catalyst.

Average Molecular Weight

The CD copolymer preferably has a number average molecular weight (Mn) as determined by size exclusion chromatography of at least 1500 g/mol, more specifically 1500 g/mol to 1,000,000 g/mol, 4000 g/mol to 150000 g/mol, or 4000 g/mol to 50000 g/mol. In an embodiment, the block copolymer has a number average molecular weight $M_n$ of 10,000 to 20,000 g/mole. The block copolymer preferably has a narrow polydispersity index (PDI) of 1.01 to 2.0, more particularly 1.01 to 1.30, and even more particularly 1.01 to 1.25.

The ABA copolymer preferably has a number average molecular weight (Mn) as determined by size exclusion chromatography of at least 1500 g/mol, more specifically 1500 g/mol to 1,000,000 g/mol, 4000 g/mol to 150000 g/mol, or 4000 g/mol to 50000 g/mol. In an embodiment, the block copolymer has a number average molecular weight $M_n$ of 10,000 to 20,000 g/mole. The block copolymer preferably has a narrow polydispersity index (PDI) of 1.01 to 2.0, more particularly 1.01 to 1.30, and even more particularly 1.01 to 1.25.

Endcap Agents

The ring opened polymer can further be treated with an endcap agent to prevent further chain growth and stabilize the reactive end groups against unwanted side reactions such as chain scission. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap agent can also comprise a biologically active moiety, which becomes bound to the terminal end group of the ring opened polymer chain.

Cytotoxicity of the Block Copolymer

The ABA and CD copolymers alone are generally non-cytotoxic. For example, cell viability of HepG2, a human liver carcinoma cell line, is in a range of 95% or more at CD block copolymer concentrations of 470 mg/L, or higher. The cell viability of human dermal fibroblasts is also in the range of 95% or more at ABA TRI(35:2.4) block copolymer concentration of 4 wt %.

Loaded Micelles

In water optionally containing organic solvent, the CD copolymer self-assembles to form a nanoparticulate micelle solution. When a biologically active cargo material is also present, the block copolymer and cargo material form a loaded micelle bound by non-covalent interactions.

A method comprises i) forming a solution of the amphiphilic CD diblock copolymer (i.e., carrier) and a biologically active material (i.e., cargo) in a water miscible organic solvent, ii) dialyzing the solution against deionized water using a dialysis membrane system, thereby forming an aqueous mixture comprising a loaded micelle. The loaded micelle comprises the CD block copolymer in an amount of 85.0 wt % to 99.9 wt %, and the biologically active material in an amount of about 15.0 wt % to 0.1 wt %, each based on total dry weight of the loaded micelle. Preferably, the dialysis membrane has a molecular weight cutoff (MWCU) of about 1000 Da.

The membrane dialysis can be conducted with or without agitation. Smaller and more uniform nanoparticles of the loaded micelle are generally favored by less mechanical agitation (e.g., stirring). Preferably, dialysis is conducted using minimal or no agitation, accompanied by occasional replacement of the external water bath with fresh deionized water, allowing the water and organic solvent to exchange by diffusion alone. The resulting aqueous mixture can be centrifuged to remove large agglomerates. The resulting supernatant can contain about 37 wt % to about 70 wt % of the original combined dry weight of the CD copolymer and the biologically active cargo material.

The dialysis is preferably conducted for a time period of 1 hour to 5 days, more preferably for a period of 1 day to 3 days.

The dialysis can be conducted at room temperature (18° C. to 28° C.), or at a lower temperature. In an embodiment, the dialysis is conducted at a temperature less than 10° C., more preferably 1° C. to 6° C. Lower temperature dialysis favors smaller loaded micelle particle sizes.

The term "loading efficiency" refers to the percentage of the initial weight of the biologically active material that is incorporated into the loaded micelle. The loading efficiency of the biologically active material in the loaded micelle is preferably at least 10%. Generally, the loading efficiency of the biologically active material is in a range of 10% to 50%, and even more specifically in a range of 30% to 50%.

Nanoparticles of the loaded micelle can have an average particle size (circular cross sectional diameter) of 10 nm to 500 nm, 10 nm to 250 nm, and preferably 25 nm to 200 nm as measured by dynamic light scattering. For the foregoing particle sizes, the aqueous solution can have a pH of 4.5 to 8.0, 5.0 to 7.0, or 6.0 to 7.0.

The organic solvent used to form a solution of the CD block copolymer and the biologically active cargo material is preferably miscible with water at concentrations of at least 1 microliter or more of organic solvent per 100 microliters of water. Exemplary organic solvents include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane.

As stated above, the biologically active cargo material can be a drug. Exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cyclosporin (an immunosuppressive agent, normally given to patients for life long after organ transplantation), Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Finasteride (for hair growth), Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AVD, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, Spironolactone, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

Toxicity of the Loaded Micelle

The toxicity of the loaded micelles toward a given cell can be at least comparable to the toxicity of the biologically active material alone toward the given cell. For example, a PTX loaded block copolymer can be as toxic to HepG2 as the PTX alone when tested under otherwise identical conditions.

Formation of Composite Hydrogels

A method of preparing a composite hydrogel comprises forming a mixture comprising a solid ABA copolymer and an aqueous loaded micelle solution comprising the CD copolymer and a biologically active substance, thereby forming a second mixture. Agitating the second mixture results in dissolution of the ABA copolymer, thereby forming a composite hydrogel.

Another method comprises forming a first mixture comprising a loaded micelle in water, forming a second mixture comprising the ABA copolymer in water, and combining the first mixture and the second mixture with agitation, thereby forming the composite hydrogel.

Using either of the above methods, the composite hydrogel can have a solids content of about 4 wt % to about 8 wt % based on total weight of the composite hydrogel.

INDUSTRIAL APPLICABILITY

The composite hydrogels can be used for human and/or non-human therapeutic treatments. The compositions can be administered in the form of a powder, a pill, a liquid solution, paste, or a gel. The compositions can be used as a drug. The compositions can be administered orally or by way of other body cavities, by injection, intravenously, and/or topically. The compositions are particularly attractive for delivery of rigid, hydrophobic biologically active materials that have low water solubility, such as paclitaxel.

A method comprises contacting a cell with a composite hydrogel, thereby killing the cell. In an embodiment, the cell is a cancer cell, and the biologically active material is PTX.

A composite hydrogel can comprise a loaded micelle that encapsulates an antimicrobial material. The antimicrobial compositions can be applied to a human and/or non-human animal tissue, including mammalian and/or non-mammalian animal tissue. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces. In an embodiment, a method comprises contacting a microbe with an antimicrobial composition, thereby killing the microbe. The antimicrobial compositions can be used in the form of a powder, a pill, or an aqueous mixture applied as a freely flowing liquid, spray, cream, injectable mixture, or gel. Uses include disinfectant washes for hands, skin, hair, bone, ear, eye, nose, throat, internal tissue, wounds, and teeth (e.g., as a mouthwash). Still other uses include disinfectants for articles such as medical devices. Medical devices include swabs, catheters, sutures, stents, bedpans, gloves, facial masks, absorbent pads, absorbent garments, internal absorbent devices, and insertable mechanical devices. In an embodiment, an article comprises a medical device in contact with the antimicrobial composition.

The antimicrobial compositions are also attractive as disinfecting agents for surfaces of articles (i.e., non-living articles) such as, for example, building surfaces in homes, businesses, and particularly hospitals. Exemplary home and commercial building surfaces include floors, door surfaces, bed surfaces, air conditioning surfaces, bathroom surfaces, railing surfaces, kitchen surfaces, and wall surfaces. Other articles include medical devices, cloths, garments, and non-medical equipment. Surfaces of articles can comprise materials such as wood, paper, metal, cloth, plastic, rubber, glass, paint, leather, or combinations thereof. In an embodiment, a method comprises contacting a surface of an article with the antimicrobial composition. In another embodiment, a method comprises contacting a surface of an article with an aqueous mixture of the antimicrobial composition.

The following examples demonstrate the preparation and use of composite hydrogels prepared with an ABA triblock copolymer and CD diblock copolymer produced by organo-catalytic ring-opening polymerization of a steroidal monomer.

EXAMPLES

Materials used in the following examples are listed in Table 7.

TABLE 7

| ABBREVIATION | DESCRIPTION | SUPPLIER |
|---|---|---|
| TMC | Trimethylene Carbonate | Boehringer Ingelheim |
| DBU | Diazabicyclo[5.4.0]Undec-7-Ene | Sigma Aldrich |
| TU | N-Bis(3,5-Trifluoromethyl)Phenyl-N'-Cyclohexylthiourea | Prepared below |
| Chol-Cl | Cholesteryl Chloroformate | Sigma Aldrich |
| mPEG-OH | Mono-Methyl Poly(Ethylene Glycol), number average molecular weight (Mn) 5K, degree of polymerization DP ~113 | Polymer Science |
| PEG10 | Poly(Ethylene Glycol), number average molecular weight (Mn) 10.9K, degree of polymerization DP ~226 | Sigma Aldrich |
| PEG20 | Poly(Ethylene Glycol), number average molecular weight (Mn) 20K, degree of polymerization DP ~452 | Sigma Aldrich |
| PEG35 | Poly(Ethylene Glycol), number average molecular weight (Mn) 35K, degree of polymerization DP ~795 | Sigma Aldrich |
| Bis-MPA | 2,2-Bis(Hydroxymethyl)Propionic Acid | Sigma Aldrich |
| FITC | Fluorescein Isothiocyanate | Sigma Aldrich |

Unless, specifically mentioned, all materials were purchased from Sigma-Aldrich, TCI or Merck. All solvents were of analytical grade, purchased from Fisher Scientific or J. T. Baker and used as received. Trimethylene carbonate (TMC) was purchased from Boehringer Ingelheim (Ingelheim, Germany), and dried extensively by freeze drying process under high vacuum. 1,8-diazabicyclo[5.4.0]undec-7-ene (DBU) was distilled from $CaH_2$ under dry $N_2$ and transferred to glove box. Before transferring into the glove box, monomers and other reagents (e.g., mPEG-OH, PEG10, PEG20, and PEG35) were dried extensively by freeze-drying under high vacuum. The cholesterol functionalized aliphatic cyclic carbonate monomer (Chol-MTC) was prepared as described below.

N-bis(3,5-trifluoromethyl)phenyl-N'-cyclohexylthiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over $CaH_2$, filtering, and removing solvent under vacuum.

Nuclear Magnetic Resonance (NMR) Spectroscopy

The $^1H$- and $^{13}C$-NMR spectra of monomers and polymers were recorded using a Broker Avance 400 spectrometer, and operated at 400 and 100 MHz respectively, with the solvent proton signal as the internal reference standard.

Molecular Weight Determination by Size Exclusion Chromatography (SEC)

SEC was conducted using THF as the eluent for monitoring the polymer conversion and also for the determination of polystyrene equivalent molecular weights of the macro-transfer agents. THF-SEC was recorded on a Waters 2695D Separation Module equipped with a Waters 2414 differential refractometer and Waters HR-4E as well as HR-1 columns. The system was equilibrated at 30° C. in THF, which served as the polymer solvent and eluent with a flow rate of 1.0 mL/min. Polymer solutions were prepared at a concentration of about 3 mg/mL, and an injection volume of 100 microliters was used. Data collection and analysis were performed using the Astra software (Wyatt Technology Corporation, USA; version 5.3.4.14). The columns were calibrated with a series of polystyrene standards ranging from $M_P$=360 Da to $M_P$=778 kDa (Polymer Standard Service, USA).

Monomer Synthesis

Cholesteryl bearing cyclic carbonate monomer Chol-MTC was synthesized from commercially available cholesteryl chloroformate (Chol-Cl) according to Scheme 1.

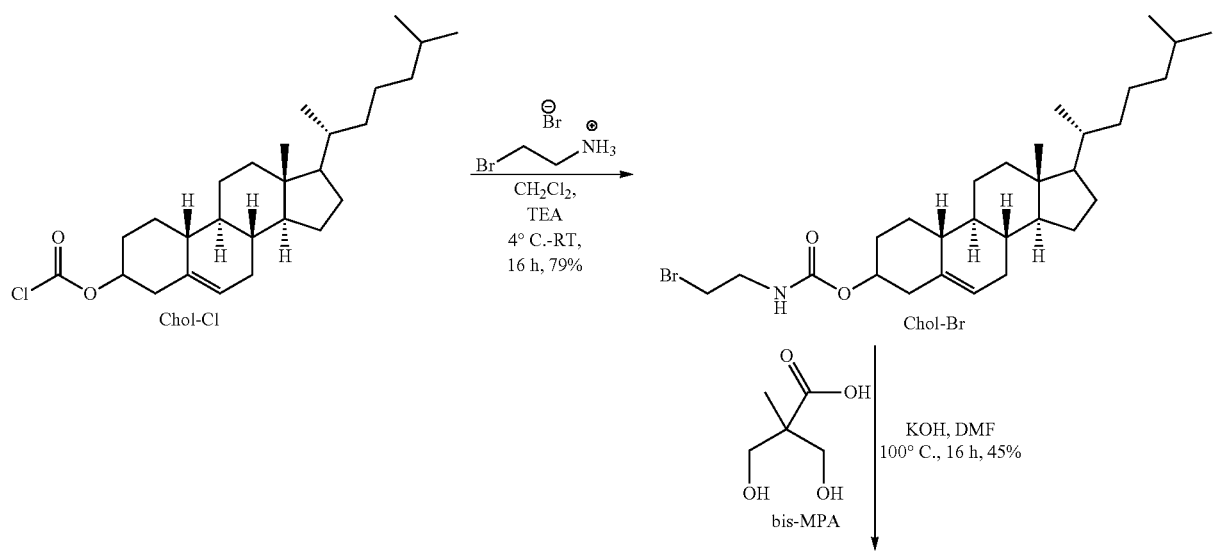

Scheme 1.

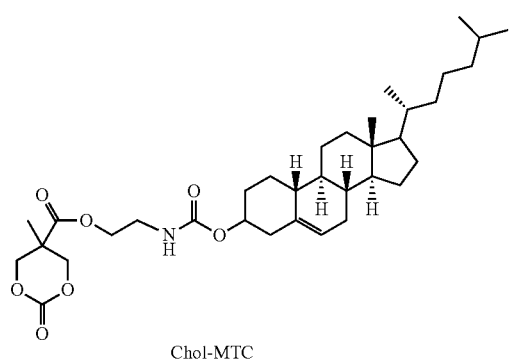
Chol-MTC

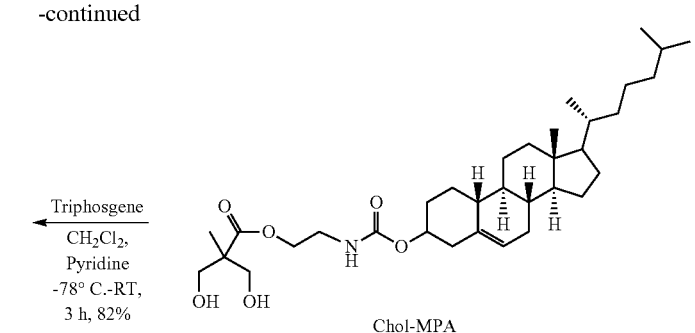
Chol-MPA

The preparation involves three steps: 1) reaction of the choloroformate Chol-Cl with 2-bromoethyl amine hydrobromide in dichloromethane with triethylamine (TEA) to form carbamate Chol-Br; 2) base-catalyzed reaction of Chol-Br with the acid diol bis-MPA in dimethylformamide (DMF)/KOH to form the diol ester Chol-MPA, and 3) triphosgene-mediated cyclization of Chol-MPA to form the cyclic carbonate monomer Chol-MTC, with overall yield of about 26%. Detailed procedures of each of the three steps are provided below. $^1$H and $^{13}$C NMR were used to confirm the structures of the intermediates and the cyclic carbonate monomer.

Example 1

Preparation of Chol-Br. In a 500 mL round bottom flask, equipped with a magnetic stir bar, cholesterol chloroformate (25.0 g, 55.7 mmol, 1.0 equiv.) and 2-bromoethylamine hydrobromide (12.9 g, 63.0 mmol, 1.1 equiv.) were suspended in dichloromethane (200 mL) and the suspension was chilled in an ice-bath. To this suspension, a solution of triethylamine (TEA) (18.0 mL, 13.06 g, 129.1 mmol, 2.3 equiv.) in dichloromethane (100 mL) was added dropwise over 1 hour. The reaction mixture was maintained in the bath for an additional hour and was allowed to warm to room temperature. The reaction was then allowed to proceed for another 14 h, after which dichloromethane was removed under vaccuo and the resultant solids were suspended in a 1:1 mixture of ethyl acetate and hexanes (300 mL). Organic layer was washed 2 times with a mixture of saturated brine (100 mL) and de-ionized water (50 mL), and one time with saturated brine (100 mL). The organic layer was dried over sodium sulfate and the solvents were removed under vacuuo to yield a pale yellow solid (29.1 g, 97.4%). As the crude product was determined to have satisfactory purity by $^1$H NMR, no further purification was conducted. $^1$H NMR (400 MHz, CDCl$_3$, delta, ppm): 5.38 (CH═C in cholesterol), 5.03 (NHCOO of side-chain), 4.50 (CH—OCONH of cholesterol), 3.58 (BrCH$_2$CH$_2$NH), 2.45-0.6 (the remaining protons from cholesterol).

Example 2

Synthesis of Chol-MPA. In a 500 mL round bottom flask with magnetic stir bar, a mixture of KOH (85%, 2.0 g, 30.3 mmol, 1.1 equiv.), bis-MPA (4.20 g, 31.3 mmol, 1.1 equiv.) and dimethylformamide (DMF) (200 mL) were heated to 100° C. for 1.5 hours. A homogenous solution was formed, and Chol-Br (15.0 g, 28.0 mmol, 1.0 equiv.) was added to the hot solution. Stirring was continued with heating for 16 hours and most of the DMF was removed under reduced pressure, to result in oily semisolid, which was then dissolved in 2:1 ethyl acetate:hexanes mixture (300 mL). The organic solution was washed with saturated brine (100 mL) and de-ionized water (100 mL) mixture. The resultant aqueous layer was extracted with ethyl acetate (3×100 mL) to recover Chol-MPA lost during the washing process. The combined organic layers were washed with saturated brine (80 mL) and de-ionized water (20 mL) mixture. The combined organic layer was dried with Na$_2$SO$_4$ and the solvent removed in vacuuo to result in crude product as a pale white waxy solid (16.5 g). The crude product was purified by flash column chromatography using silica as the packing material and a gradient of hexanes to ethyl acetate as the eluent to result in the final product Chol-MPA as a waxy white solid (10.7 g, 64.8%). $^1$H NMR (400 MHz, CDCl$_3$, delta, ppm): 5.35 (CH═C in cholesterol and NHCOO of side-chain), 4.47 (CH—OCONH of cholesterol), 4.26 (CH$_2$CH$_2$NHCOO), 3.88 and 3.72 (CH$_2$OH) 3.45 (CH$_2$CH$_2$NHCOO), 3.34 (OH), 2.50-0.60 (the remaining protons from cholesterol and CH$_3$ from bis-MPA).

Example 3

Preparation of Chol-MTC. In a 500 mL round bottom flask with magnetic stir bar, Chol-MPA (10.1 g, 17.1 mmol, 1.0 equiv.) was dissolved in anhydrous dichloromethane (150 mL). Pyridine (8.2 mL, 8.0 g, 101.5 mmol, 5.9 equiv.) was added and the solution was cooled in a dry ice-acetone bath (−78° C.). To this cooled reaction mixture, triphosgene (2.69 g, 9.06 mmol, 1.9 equivalents based on functional equivalents of triphosgene) solution (dissolved in 50 mL dichloromethane) was added dropwise over 1 hour. After 1 hour, from −78° C., the reaction mixture was allowed to warm up to room temperature, and after 2 hours, the reaction was quenched by adding saturated aqueous ammonium chloride solution (50 mL). The organic layer was washed twice with a mixture of 1.0 N HCl (20 mL) and saturated brine (80 mL), followed by a mixture of saturated brine (50 mL) and saturated NaHCO$_3$ (50 mL), dried using Na$_2$SO$_4$. Removal of solvent in vacuo resulted in crude product as a slightly yellowish solid. The crude product was further purified by flash column chromatography using silica as the packing material and a gradient of chloroform to chloroform:ethyl acetate(4:1) mixtures as the eluent, to result in the final product Chol-MTC as a waxy white solid (6.8 g, 65%). $^1$H NMR (400 MHz, CDCl$_3$, delta, ppm): 5.35 (CH═C in cholesterol), 4.95 (NH-COO), 4.86 and 4.27 (CH$_2$OCOOCH$_2$), 4.47 (CH—OCONH of cholesterol), 4.27 (CH$_2$CH$_2$NHCOO), 3.45 (CH$_2$CH$_2$NHCOO), 2.40-0.60 (the remaining protons from cholesterol and CH$_3$ in the cyclic carbonate monomer).

Preparation of CD Diblock Copolymers by Ring Opening Polymerization

The ring opening homopolymerization of Chol-MTC resulted in low conversion and/or low degree of polymerization when the ring opening polymerization was initiated by benzyl alcohol (BzOH) or mPEG-OH. On the other hand, copolymerization of Chol-MTC with TMC was found to occur with high conversion (>90%). Therefore, TMC was used as a diluent comonomer to prepare several amphiphilic block copolymers according to Scheme 2.

Scheme 2.

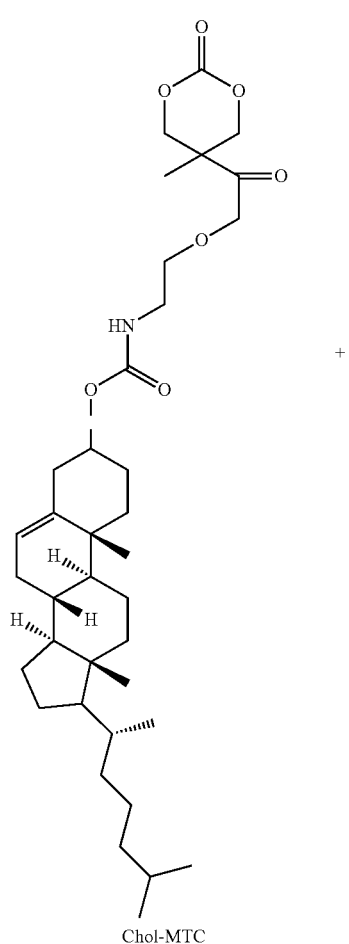

Chol-MTC

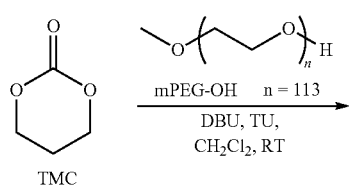

TMC    mPEG-OH  n = 113
       DBU, TU,
       CH$_2$Cl$_2$, RT

-continued

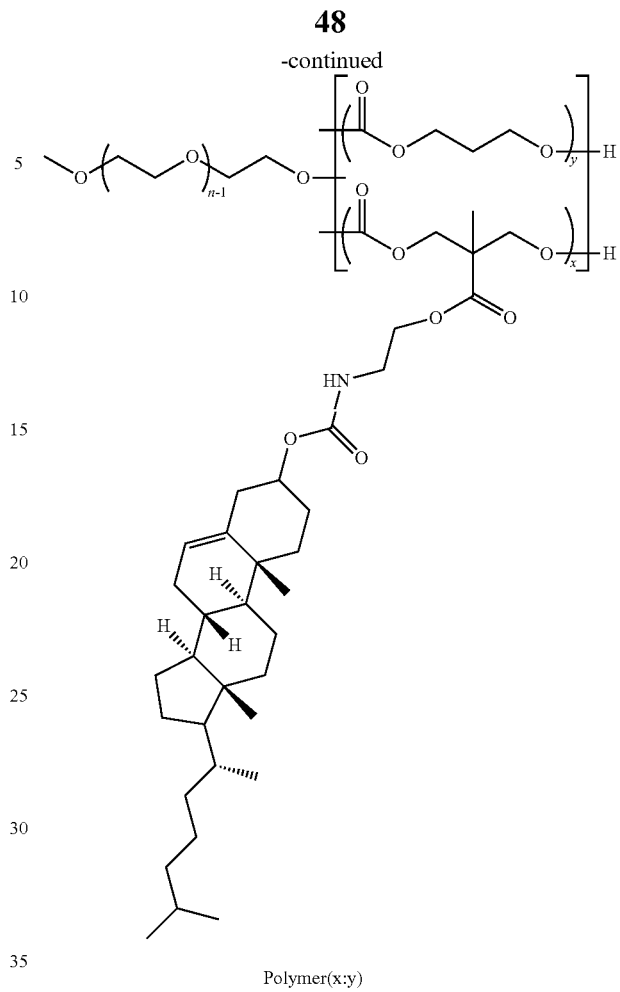

Polymer(x:y)

The TMC not only assists in achieving high monomer conversions, but also serves to dilute/spread out the rigid cholesteryl side chain groups across the hydrophobic region. The cholesteryl bearing polymers prepared according to Scheme 2 are represented by the name Polymer(x:y), where x and y represent numbers of units derived from Chol-MTC and TMC, respectively, in the block copolymer structure of Scheme 2. The subscript n in the mPEG-OH structure (Scheme 2) was about 113, corresponding to a number average molecular weight (Mn) of 5000 Da. The stacked subunit structures between the vertical brackets in the block copolymer structure of Scheme 2 indicate the polycarbonate block of Polymer(x:y) is a random copolymer of repeat units derived from Chol-MTC and TMC.

In the following Examples 4 to 9, amounts were calculated based on following: i) the initiator (mPEG-OH) has one nucleophilic initiating group (hydroxy group) per mole of the initiator, ii) the molecular weight of mPEG-OH=5000 g/mole, and iii) the molar amount of initiator was set to one equivalent relative to equivalents of cyclic carbonyl monomer.

Example 4

Preparation of Polymer(0:67). In a 7 mL vial containing a magnetic stir bar, in glove box, TMC (MW=102.1, 922 mg, 9.03 mmol, 180.6 equivalents), mPEG-OH (5 kDa, 250 mg, 50.0 micromoles, 1.0 equivalent) and TU (MW=370.4, 47.0 mg, 127 micromoles, 2.5 equiv.) were dissolved in dichloromethane (2.5 mL). To this solution, DBU (MW=152.24, 18.7 microliters, 19.1 mg, 124 micromoles, 2.5 equivalents) was added to initiate polymerization. The reaction mixture was allowed to stir at room temperature and aliquots of samples were taken to monitor the monomer conversion and the molecular weight by $^1$H NMR spectroscopy and size exclusion chromatography (SEC). After 40 hours, the reaction was quenched by the addition of about 20 mg of benzoic acid and was precipitated in ice-cold diethyl ether (2×50 mL). Polymer(0:67) was dried in a tared vial for about 1 to 2 days, until a constant sample mass was obtained as white powder (580 mg). The number average molecular weight by NMR (Mn (NMR))=11800 Da. $^1$H NMR (400 MHz, CDCl$_3$, delta, ppm): 4.20-4.30 ($CH_2CH_2CH_2OCOO$), 3.85-3.5, 3.38 ($CH_3$ of mPEG), 2.10-2.00 ($CH_2CH_2CH_2OCOO$). The degree of polymerization (DP) of TMC was 67. The polydispersity index (PDI) was 1.12.

Example 5

Preparation of Polymer(4:0). In a 7 mL vial containing a magnetic stir bar, in glove box, Chol-MTC (MW=616, 312 mg, 507 micromoles, 10.1 equivalents), mPEG-OH (5 kDa, 251 mg, 50.2 micromoles, 1.0 equivalent) and TU (MW=370.4, 46.0 mg, 125 micromoles, 2.5 equiv.) were dissolved in dichloromethane (2.5 mL). To this solution, DBU (MW=152.24, 18.7 microliters, 19.1 mg, 124 micromoles, 2.5 equivalents) was added to initiate polymerization. The reaction mixture was allowed to stir at room temperature and aliquots of samples were taken to monitor the monomer conversion and the molecular weight by $^1$H NMR spectroscopy and SEC. After 18 hours, the reaction was quenched by the addition of about 20 mg of benzoic acid and was precipitated in ice-cold diethyl ether (2×50 mL). Polymer (4:0) was dried in a tared vial for about 1 to 2 days, until a constant sample mass was obtained as white powder (356 mg). Mn (NMR)=7500 Da. $^1$H NMR (400 MHz, CDCl$_3$, δ, ppm): 5.45-5.35 (CH=C in cholesterol), 5.35-5.05 (NHCOO of side-chain), 4.65-4.40 (CH—OCONH of cholesterol), 4.40-4.10 ($CH_2OCOOCH_2$ and $CH_2CH_2NHCOO$), 3.85-3.5 ($CH_2CH_2O$ of mPEG) 3.5-3.30 ($CH_2CH_2NHCOO$), 3.38 ($CH_3$ of mPEG), 2.45-0.55 (rest of the protons from cholesterol and $CH_3$ in the cyclic carbonate monomer). The DP of Chol-MTC was 4. The PDI was 1.12.

Example 6

Preparation of Polymer(11:0). In a 7 mL vial containing a magnetic stir bar, in glove box, Chol-MTC (MW=616, 312 mg, 995 micromoles, 19.1 equivalents), mPEG-OH (5 kDa, 260 mg, 52.0 micromoles, 1.0 equivalent) and TU (MW=370.4, 48.0 mg, 130 micromoles, 2.5 equiv.) were dissolved in dichloromethane (2.5 mL). To this solution, DBU (MW=152.24, 18.7 microliters, 19.1 mg, 124 micromoles, 2.4 equivalents) was added to initiate polymerization. The reaction mixture was allowed to stir at room temperature and aliquots of samples were taken to monitor the monomer conversion and the molecular weight by $^1$H NMR spectroscopy and SEC. After 6 hours, the reaction was quenched by the addition of about 20 mg of benzoic acid and was precipitated in ice-cold diethyl ether (2×50 mL). Polymer (11:0) was dried in a tared vial for about 1 to 2 days, until a constant sample mass was obtained as white powder (612 mg). Mn (NMR)=11800 Da. $^1$H NMR (400 MHz, CDCl$_3$, delta, ppm): 5.45-5.35 (CH=C in cholesterol), 5.35-5.05 (NHCOO of side-chain), 4.65-4.40 (CH—OCONH of cholesterol), 4.40-4.10 ($CH_2OCOOCH_2$ and $CH_2CH_2NHCOO$), 3.85-3.5 ($CH_2CH_2O$ of mPEG) 3.5-3.30 ($CH_2CH_2NHCOO$), 3.38 ($CH_3$ of mPEG), 2.45-0.55 (rest of the protons from cholesterol and $CH_3$ in the cyclic carbonate monomer). The DP of Chol-MTC was 11. PDI was 1.21.

Ring opened block copolymers having different x:y ratios (Chol-MTC units:TMC units) were prepared using the initiator mPEG-OH (5.0 kDa).

Example 7

Preparation of Polymer (8:8). In a 7 mL vial containing a magnetic stir bar, in glove box, Chol-MTC (MW=616, 617 mg, 1000 micromoles, 9.9 equivalents), TMC (MW=102.1, 109 mg, 1.07 mmol, 10.6 equivalents), mPEG-OH (5 kDa, 506 mg, 101 micromoles, 1.0 equivalent) and TU (MW=370.4, 103 mg, 278 micromoles, 2.7 equiv.) were dissolved in dichloromethane (2.0 mL). To this solution, DBU (MW=152.24, 37.3 microliters, 38.0 mg, 250 micromoles, 2.5 equivalents) was added to initiate polymerization. The reaction mixture was allowed to stir at room temperature and aliquots of samples were taken to monitor the monomer conversion and the molecular weight by $^1$H NMR spectroscopy and SEC. After 5 hours, the reaction was quenched by the addition of about 30 mg of benzoic acid and was precipitated in ice-cold diethyl ether (2×50 mL). Polymer (8:8) was dried in a tared vial for about 1 to 2 days, until a constant sample mass was obtained as white powder (968 mg). Mn (NMR)=10700 Da. $^1$H NMR (400 MHz, CDCl$_3$, delta, ppm): 5.45-5.35 (CH=C in cholesterol), 5.35-5.05 (NHCOO of side-chain), 4.65-4.40 (CH—OCONH of cholesterol), 4.40-4.10 ($CH_2OCOOCH_2$, $CH_2CH_2NHCOO$ and $CH_2CH_2CH_2OCOO$ of TMC), 3.85-3.5 ($CH_2CH_2O$ of mPEG) 3.5-3.30 ($CH_2CH_2NHCOO$), 3.38 ($CH_3$ of mPEG), 2.45-0.55 (rest of the protons from cholesterol, $CH_3$ in the cyclic carbonate monomer and $CH_2CH_2NHCOO$ of TMC). The DP of Chol-MTC was 8. The DP of TMC was 8. The PDI was 1.18.

Example 8

Preparation of Polymer(11:30). In a 7 mL vial containing a magnetic stir bar, in glove box, Chol-MTC (MW=616, 699 mg, 520 micromoles, 10.4 equivalents), TMC (MW=102.1, 154 mg, 1.51 mmol, 30.3 equivalents), mPEG-OH (5 kDa, 249 mg, 49.8 micromoles, 1.0 equivalent) and TU (MW=370.4, 46.0 mg, 125 micromoles, 2.5 equiv.) were dissolved in dichloromethane (2.5 mL). To this solution, DBU (MW=152.24, 18.7 microliters, 19.1 mg, 124 micromoles, 2.5 equivalents) was added to initiate polymerization. The reaction mixture was allowed to stir at room temperature and aliquots of samples were taken to monitor the monomer conversion and the molecular weight by $^1$H NMR spectroscopy and SEC. After 18 hours, the reaction was quenched by the addition of about 20 mg of benzoic acid and was precipitated in ice-cold diethyl ether (2×50 mL). Polymer (11:30) was dried in a tared vial for about 1 to 2 days, until a constant sample mass was obtained as white powder (614 mg). Mn (NMR)=14800 Da. $^1$H NMR (400 MHz, CDCl$_3$, delta, ppm): 5.45-5.35 (CH=C in cholesterol), 5.35-5.05 (NHCOO of side-chain), 4.65-4.40 (CH—OCONH of cholesterol), 4.40-4.10 ($CH_2OCOOCH_2$, $CH_2CH_2NHCOO$ and $CH_2CH_2CH_2OCOO$ of TMC), 3.85-3.5 ($CH_2CH_2O$ of mPEG) 3.5-3.30 ($CH_2CH_2NHCOO$), 3.38 ($CH_3$ of mPEG), 2.45-0.55 (rest of the protons from cholesterol, $CH_3$ in the cyclic carbonate monomer and $CH_2CH_2NHCOO$ of TMC). DP of Chol-MTC was 11. The DP of TMC was 30. The PDI was 1.20.

Example 9

Preparation of Polymer(18:55). In this example, a higher level of catalyst (5.0 equiv of with respect to initiator) was used because it was found from Example 4 that polymerization kinetics were slower for relatively high initiator to monomer ratios. In a 7 mL vial containing a magnetic stir bar, in glove box, Chol-MTC (MW=616, 876 mg, 1.42 mmol, 19.6 equivalents), TMC (MW=102.1, 452 mg, 4.43 mmol, 61.2 equivalents), mPEG-OH (5 kDa, 362 mg, 72.4 micromoles, 1.0 equivalent) and TU (MW=370.4, 134 mg, 362 micromoles, 4.8 equiv.) were dissolved in dichloromethane (3.0 mL). To this solution, DBU (MW=152.24, 52.3 microliters, 53.3 mg, 350 micromoles, 5.0 equivalents) was added to initiate polymerization. The reaction mixture was allowed to stir at room temperature and aliquots of samples were taken to monitor the monomer conversion and the molecular weight by $^1$H NMR spectroscopy and SEC. After 4 hours, the reaction was quenched by the addition of about 30 mg of benzoic acid and was precipitated in ice-cold diethyl ether (2×50 mL). Polymer (18:55) was dried in a tared vial for about 1 to 2 days, until a constant sample mass was obtained as white powder (533 mg). Mn (NMR)=21700 Da. $^1$H NMR (400 MHz, CDCl$_3$, delta, ppm): 5.45-5.35 (CH=C in cholesterol), 5.35-5.05 (NHCOO of side-chain), 4.65-4.40 (CH—OCONH of cholesterol), 4.40-4.10 (CH$_2$OCOOCH$_2$, CH$_2$CH$_2$NHCOO and CH$_2$CH$_2$CH$_2$OCOO of TMC), 3.85-3.5 (CH$_2$CH$_2$O of mPEG) 3.5-3.30 (CH$_2$CH$_2$NHCOO), 3.38 (CH$_3$ of mPEG), 2.45-0.55 (rest of the protons from cholesterol, CH$_3$ in the cyclic carbonate monomer and CH$_2$CH$_2$NHCOO of TMC). DP of Chol-MTC was 18. The DP of TMC was 55. The PDI was 1.17.

Example 10

Preparation of Polymer(29:77). In a 7 mL vial containing a magnetic stir bar, in glove box, Chol-MTC (MW=616, 946 mg, 1.54 mmoles, 30.0 equivalents), TMC (MW=102.1, 464 mg, 4.55 mmol, 92.4 equivalents), mPEG-OH (5 kDa, 256 mg, 51.2 micromoles, 1.0 equivalent) and TU (MW=370.4, 95.0 mg, 257 micromoles, 4.9 equiv.) were dissolved in dichloromethane (3.0 mL). To this solution, DBU (MW=152.24, 37.3 microliters, 38 mg, 250 micromoles, 5.0 equivalents) was added to initiate polymerization. The reaction mixture was allowed to stir at room temperature and aliquots of samples were taken to monitor the monomer conversion and the molecular weight by $^1$H NMR spectroscopy and SEC. After 4 hours, the reaction was quenched by the addition of about 30 mg of benzoic acid and was precipitated in ice-cold diethyl ether (2×50 mL). Polymer (29:77) was dried in a tared vial for about 1 to 2 days, until a constant sample mass was obtained as white powder (590 mg). Mn (NMR)=30700 Da. $^1$H NMR (400 MHz, CDCl$_3$, delta, ppm): 5.45-5.35 (CH=C in cholesterol), 5.35-5.05 (NHCOO of side-chain), 4.65-4.40 (CH—OCONH of cholesterol), 4.40-4.10 (CH$_2$OCOOCH$_2$, CH$_2$CH$_2$NHCOO and CH$_2$CH$_2$CH$_2$OCOO of TMC), 3.85-3.5 (CH$_2$CH$_2$O of mPEG) 3.5-3.30 (CH$_2$CH$_2$NHCOO), 3.38 (CH$_3$ of mPEG), 2.45-0.55 (rest of the protons from cholesterol, CH$_3$ in the cyclic carbonate monomer and CH$_2$CH$_2$NHCOO of TMC). The DP of Chol-MTC was 29. The DP of TMC was 77. The PDI was 1.21.

Each of the above described block copolymers has a polydispersity index (PDI) of less than 1.25.

Properties of the self-assembled polymers without drug loading are summarized in Table 8. Example 4 and Examples 7 to 10 have an x:y ratio less than or equal to 1.0 (x:y=0:67, 8:8, 11:30; 18:55; 29:77, respectively). Examples 5 and 6 have an x:y ratio greater than 1.0 (x:y=4:0, 11:0, respectively).

TABLE 8

| Example | Polymer(x:y) | Units of Chol-MTC (x) | Units of TMC (y) | Mn | CMC (mg/L) | Micelle Size (nm) | Micelle PDI |
|---|---|---|---|---|---|---|---|
| 4 | Polymer(0:67) | 0 | 67 | 11800 | 2.1 | 163 ± 4 | 0.56 ± 0.01 |
| 5 | Polymer(4:0) | 4 | 0 | 7500 | — | 234.5 ± 33.0 | 0.49 ± 0.00 |
| 6 | Polymer(11:0) | 11 | 0 | 11600 | 2.1 | 114 ± 1 | 0.14 ± 0.01 |
| 7 | Polymer(8:8) | 8 | 8 | 10700 | 1.5 | 133 ± 3 | 0.44 ± 0.01 |
| 8 | Polymer(11:30) | 11 | 30 | 14800 | 1.5 | 36 ± 1 | 0.08 ± 0.05 |
| 9 | Polymer(18:55) | 18 | 55 | 21700 | 2.1 | 229 ± 51 | 0.29 ± 0.02 |
| 10 | Polymer(29:77)[a] | 29 | 77 | 30700 | | | |

[a]Example 10 was not further characterized or used for preparing loaded micelles below due to its hydrophobicity.

Critical Micelle Concentrations of CD Copolymers

General procedure for polymer self-assembly. The following dialysis method was used to prepare non-loaded micelles of the polymers of Examples 4 to 9. In a scintillation vial (20 mL) with a magnetic stir bar, block copolymer (15.0 mg) was dissolved in DMF (2.0 mL) with stirring at room temperature for about 1 hour to 2 hours. The polymer solution in DMF was then transferred to a prewashed dialysis membrane having a molecular weight cutoff (MWCO) of 1000 Da (Spectra/Por) and was dialyzed at 4° C. against deionized water (1 L). The water was changed at 3, 6 and 24 hours. At the end of the dialysis process, the resulting micelle solution was centrifuged at 4000 rpm for 5 minutes to remove large aggregates. Typically the final concentration of the polymer solution after dialysis was about 1.0 mg/mL.

Fluorescence Measurements. The critical micelle concentrations (CMCs) of the polymers in DI water were determined by fluorescence spectroscopy using pyrene as the probe. The fluorescence spectra were recorded by an LS 50B luminescence spectrometer (Perkin Elmer, U.S.A.) at 25° C. Dialyzed polymer samples (see below) were equilibrated for 10 min before taking measurements. Aliquots of pyrene in acetone solution (6.16×10$^{-5}$ M, 10 microliters) were added to glass vials and air dried to remove the acetone. Polymer solutions of varying concentrations were added to the pyrene at 1 mL each, and left to stand for 24 hours. The final pyrene concentration in each vial is 6.16×10$^{-7}$ M. The excitation spectra were scanned at wavelength from 300 nm to 360 nm with an emission wavelength of 395 nm. Both the excitation and emission bandwidths were set at 2.5 nm. The intensity (peak height) ratio of 1339/1334 from the excitation spectra was analyzed as a function of polymer concentration. The CMC was taken at the point of intersection between the tangent to the curve at the inflection and tangent of the points at low concentrations.

Transmission electron microscopy. The morphologies of the polymers under aqueous conditions were observed under a FEI Tecnai G2 F20 electron microscope using an acceleration voltage of 200 keV. The TEM samples were prepared by first placing a drop of aqueous polymer solution (4.0 microliters) onto a formvar coated 200 mesh copper grid (Ted Pella Inc., USA). After 1 min, the excess solution was wicked off by using filter paper. Then the staining agent of phosphotungstic acid (2% w/v; 4.0 microliters) was placed on the grid and after a minute, the excess solution was wicked off and the grid was left to dry under ambient conditions.

FIG. 1 is a graph showing the intensity (peak height) ratio of 1339/1334 of the excitation spectra as a function of polymer concentration for Example 4 (x:y=0:67), Example 6 (x:y=11:0), Example 7 (x:y=8:8), Example 8 (x:y=11:30), and Example 9 (x:y=18:55). The CMC values in DI water of Examples 4, and 6 to 9 are, respectively, 2.1 mg/L, 2.1 mg/L, 1.5 mg/L, 1.5 mg/L and 2.1 mg/L (Table 8). The CMC values of the polymers of Example 5 and Example 10 were not determined. The low CMC values of Examples 6 to 8 indicate that the micellar structure can exist even at low concentrations, thereby enabling in vivo application of these materials where the micellar solution would undergo an extensive dilution after administration. The polymers are expected to exhibit even lower CMC values in the bloodstream as a result of the "salting out" effect.

The average particle size diameter (in nanometers) and size distribution (PDI) of non-loaded micelles formed with the polymers are also listed in Table 8. Example 8, which has an x:y ratio (Chol-MTC:TMC=11:30) less than 1.0 and a molecular weight less than or equal to 15 kDa, the average particle size was less than 40 nm. This value is significantly smaller than the micelle particle sizes obtained with Example 5 (163 nm), Example 6 (114 nm), and Example 7 (133 nm), which have an x:y ratio greater than or equal to 1.0. The micelle polydispersity index (PDI) also indicates that the nanoparticles formed from the polymers having an x:y ratio less than 1:1 and lower molecular weight of about 15 kDa (Examples 8) have a lower particle size distribution compared to the polymers having an x:y ratio greater than or equal to about 1.0 (Examples 5 to 7).

Figure 2A:
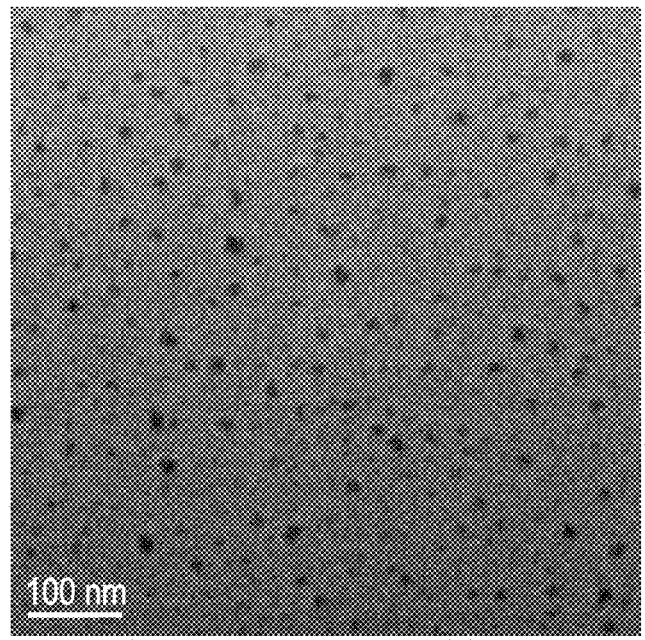
FIGS. 2A to 2F are transmission electron micrograph (TEM) images of aqueous micelles formed by the block copolymers of Examples 4 to 9, respectively. The upper image in FIG. 2F is at a magnification of 28000×. The lower image in FIG. 2F is at a magnification of 110000×.
Figure 2B:
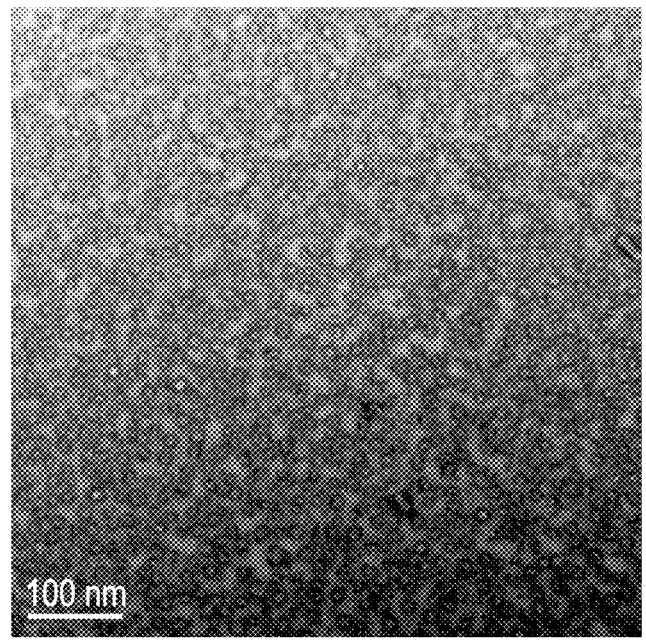
Figure 2C:
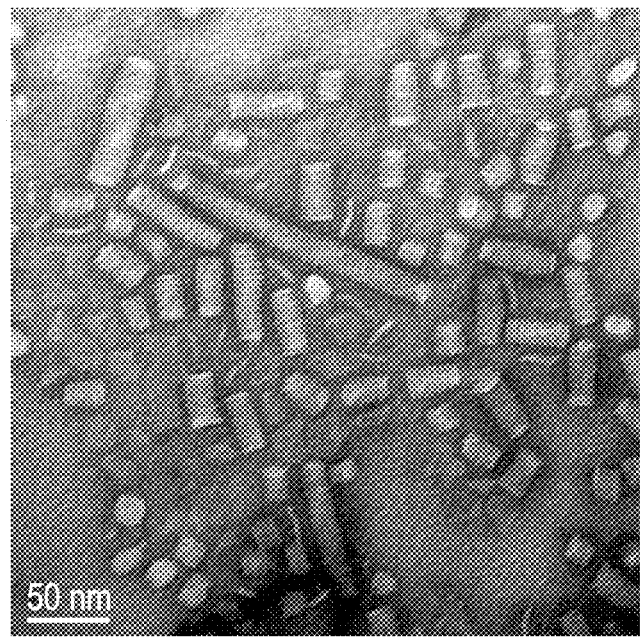
Figure 2D:
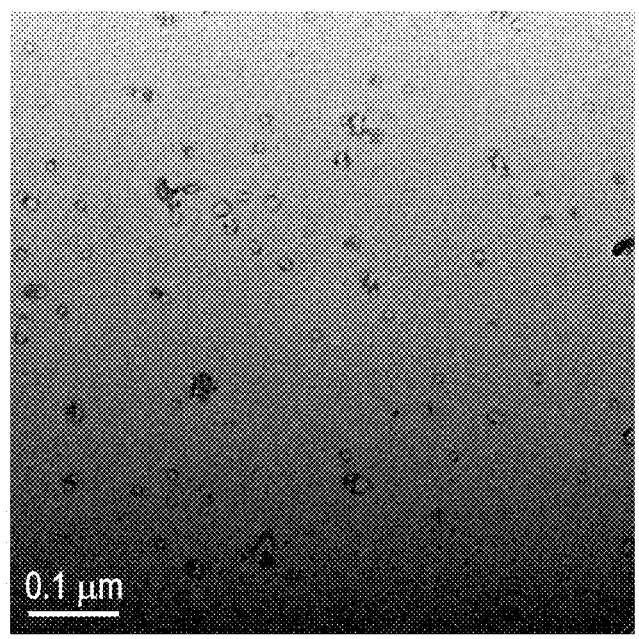
Figure 2E:
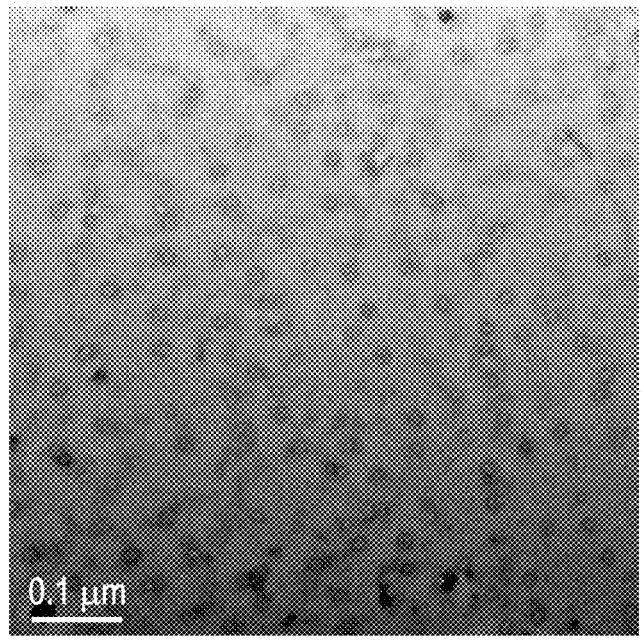
Figure 2F:
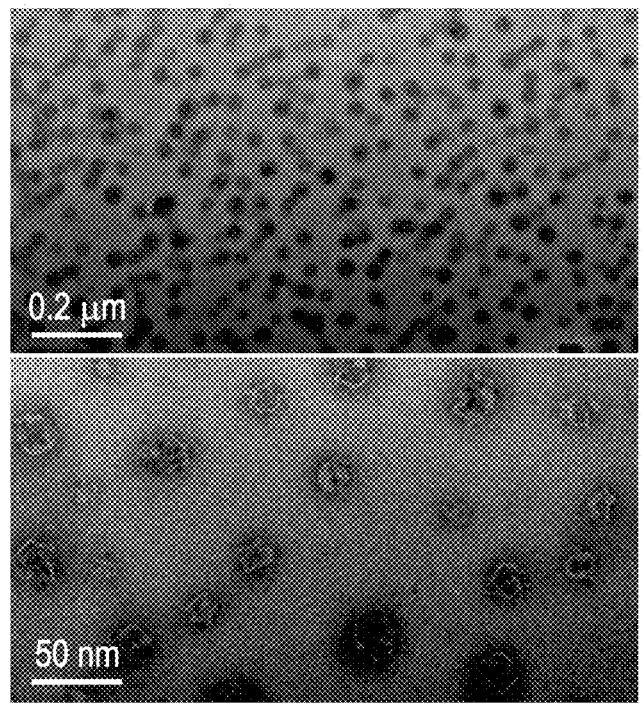

FIGS. 2A to 2F are TEM images of the micelles formed by Example 4 (x:y=0:67), Example 5 (x:y=4:0), Example 6 (x:y=11:0), Example 7 (x:y=8:8), Example 8 (x:y=11:30), and Example 9 (x:y=18:55), respectively. Comparing the TEMs of Examples 4 to 6 (FIGS. 2A to 2C), self-assembly was promoted by increasing the content of cholesteryl repeat units in the block copolymer. When TMC was used as a comonomer, discrete nanostructures were observed (Examples 8 and 9, FIGS. 2D and 2E, respectively). At high TMC content, predominantly collapsed vesicles formed (Example 9, FIG. 2F). The upper image in FIG. 2F is at a magnification of 28000×. The lower image in FIG. 2F is at a magnification of 110000×.

Cytotoxicity of CD Diblock Copolymers

HepG2 cells were maintained in DMEM growth medium supplemented with 10% FBS (fetal bovine serum), 100 microgram/mL penicillin and 100 units/mL streptomycin at 37° C., under the atmosphere of 5% $CO_2$. To assess the cytotoxicity of the amphiphilic block copolymer (Examples 4, and Examples 6 to 9) in HepG2 cells, a standard MTT (dimethyl thiazolyl diphenyl tetrazolium salt) assay protocol was employed. On a 96-well plate, cells were seeded at a density of $1 \times 10^4$ cells/well and allowed to grow for 24 hours to reach 60% to 70% confluence. Each well was replaced with 100 microliters of fresh growth medium and treated with 10 microliters of the block copolymer solution. The cytotoxicity test was performed in replicates of 6 wells per block copolymer or PTX concentration. After 4 hours of incubation, the wells were replaced with fresh medium and incubated further for 68 hours. Upon replacing the wells with 100 microliters of fresh medium and 20 microliters of MTT solution (5 mg/mL in PBS buffer), the cells were incubated for another 4 hours. Finally, the used media were removed and the internalized purple formazan crystals in each well were dissolved with 150 microliters of DMSO. A 100 microliter aliquot of the formazan/DMSO solution was transferred from each well to a new 96-well plate, and the absorbance (A) was measured using a microplate spectrophotometer (BioTek Instruments Inc, Winooski, Vt., U.S.A.) at the wavelength of 550 nm and 690 nm. To measure the relative cell viability in different polymer, the absorbance of formazan solution in the treated cells were compared to that of the control cells:

$$\text{Cell viability} = [(A_{550}-A_{690})\text{sample}/(A_{550}-A_{690})\text{control}] \times 100\%$$

where $A_{550}$ and $A_{690}$ represent absorbance at 550 nm and 690 nm, respectively, $(A_{550}-A_{690})$sample represents the difference in the absorbance at 550 nm and 690 nm of the sample, and $(A_{550}-A_{690})$control represents the difference in the absorbance at 550 nm and 690 nm for the control.

Figure 3:
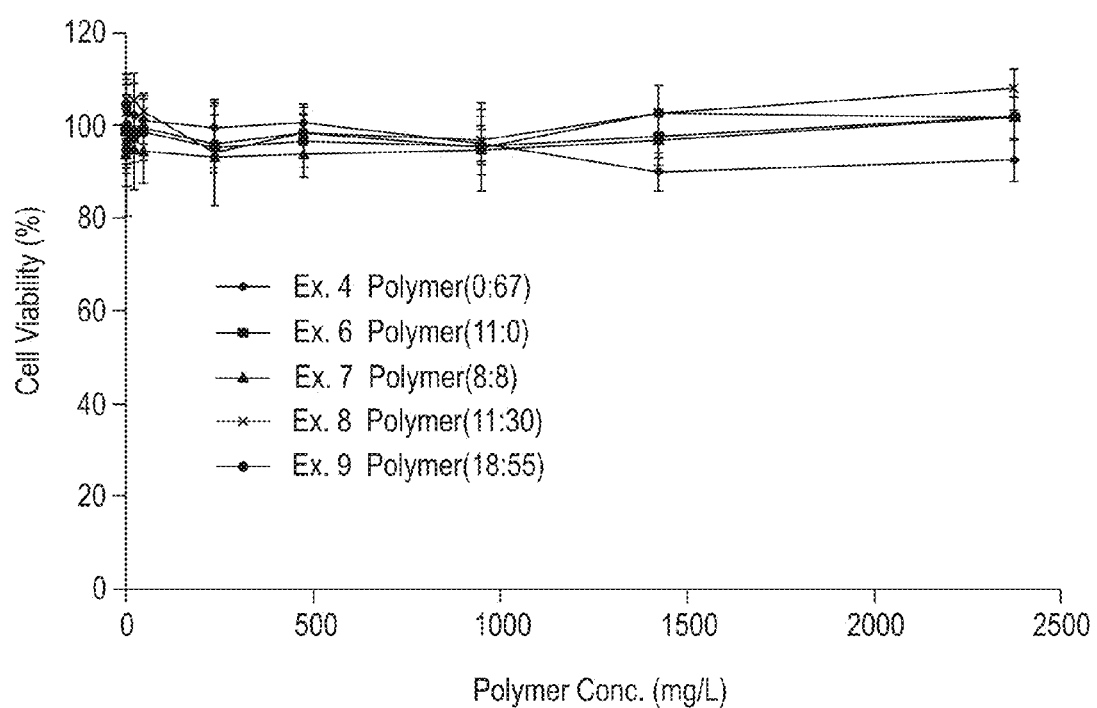
FIG. 3 is a graph showing human liver carcinoma HepG2 cell viability (%) against block copolymer concentration (Examples 4, and 6 to 9). The block copolymers are non-cytotoxic. More than 90% cell viability was observed even at the highest polymer concentration (2377 mg/L).

The data were statistically analyzed for significant differences, based on the Student's t-test at $p<0.05$. FIG. 3 is a graph showing HepG2 cell viability (%) against block copolymer concentration (Examples 4, and 6 to 9) without the drug. Each of the block copolymers was non-cytotoxic. Greater than 90% cell viability was observed even at the highest polymer concentration (2377 mg/L).

Preparation of Drug Loaded Micelles

The following examples demonstrate the following drugs can be physically entrapped by non-covalent interactions in the self-assembled diblock copolymer: Paclitaxel (PTX), Cyclosporin A (CYC, an immunosuppressive agent used after organ transplantation) and Spironolactone (SPL, a drug used to treat hypertension). The drugs can be used singularly or in combination.

General procedure for all three drugs (PTX, CYC and SPL). The dialysis method was used to prepare loaded micelles with the drugs. Polymer (15 mg) and drug (3 mg) were dissolved together in 2 mL DMF in their respective ratios. The mixture was placed in a dialysis membrane bag with molecular weight cut-off (MWCO) of 1000 Da (Spectrum Laboratories, U.S.A.). The dialysis bag was then immersed in 1 L of deionized (DI) water at 4° C. without stirring for 2 days. During the 2-day course, the external dialysis medium was replaced at 3 hours, 6 hours and 24 hours. At the end of the dialysis process, the resulting micelle solution was centrifuged at 4000 rpm for 5 minutes to remove large agglomerates. The dry weight of the agglomerates was about 30 wt % to about 60 wt % of the combined dry weight of the polymer and drug. The loaded micelles were characterized with respect to their size with a Zetasizer with dynamic light scattering capability (scattering angle: 90°) and equipped with a He—Ne laser beam at 658 nm (Malvern Instruments Zetasizer Nano ZS, UK).

PTX loading measurements. To determine the encapsulation efficiency and loading level of PTX, the drug-loaded micelles were first freeze-dried and then re-dissolved in 200 microliters of dichloromethane. 6 mL of cold ether was then added to precipitate the polymer. The mixture was centrifuged at 4000 rpm for 20 minutes and the supernatant was transferred into a fresh tube, and air dried. The deposited drug was dissolved in 4 ml, of mobile phase consisting of water:methanol:acetonitrile in the volume ratio of 35:20:45, and filtered through a 0.22 micrometer filter to remove any large aggregates. PTX loading level as weight percent (wt %) based on the total weight of the dry loaded micelle was analyzed using high performance liquid chromatography (HPLC, Waters 996 PDA detector, U.S.A.) at 228 nm. The drug loading efficiency (i.e., the percentage of the initial amount in milligrams of drug that is successfully encapsulated) was also reported. For example, if the loading efficiency is 40%, then 40% of the initial amount of paclitaxel was incorporated into the loaded micelles obtained after freeze-drying.

CYC loading measurements. To determine the encapsulation efficiency and loading level of CYC, the drug-loaded micelles were first freeze-dried and then re-dissolved in 200 microliters of dichloromethane. 6 mL of cold ether was then added to precipitate the polymer. The mixture was centrifuged at 4000 rpm for 20 minutes and the supernatant was transferred into a fresh tube, and air dried. The deposited drug was dissolved in 4 ml, of mobile phase consisting of water:acetonitrile in the volume ratio of 20:80. CYC loading level as weight percent (wt %) based on the total weight of the drug-loaded micelle was analyzed using high performance liquid chromatography (HPLC, Waters 996 PDA detector, U.S.A.) at 210 nm.

SPL loading measurements. To determine the encapsulation efficiency and loading level of SPL, the drug-loaded micelles were first freeze-dried and then re-dissolved in 200 microliters of dichloromethane. 6 mL of cold ether was then added to precipitate the polymer. The mixture was centrifuged at 4000 rpm for 20 minutes and the supernatant was transferred into a fresh tube, and air dried. The deposited drug was dissolved in 4 ml, of mobile phase consisting of water:acetonitrile in the volume ratio of 50:50. SPL loading level as weight percent (wt %) based on the total weight of the drug-loaded micelle was analyzed using high performance liquid chromatography (HPLC, Waters 996 PDA detector, U.S.A.) at 238 nm.

Examples 11 to 16

Using the above general procedure, drug loaded micelles were prepared using the polymers of Examples 4, and 6 to 10 by dialyzing at 4° C. without stirring. The loaded micelles are designated by the name PTX-Polymer(x:y), CYC-Polymer(x:y) and SPL-Polymer(x:y), where x is the number of repeat units derived from Chol-MTC and y is the number of repeat units derived from TMC.

The effects of block copolymer structure and initial drug loading on the particle size, polydispersity index (PDI), final drug loading level, and loading efficiency of the PTX loaded micelles are shown in Tables 9, 10 and 11, respectively.

TABLE 9

| Example | Loaded Micelle | Initial PTX (mg) | Units of Chol-MTC (x) | Units of TMC (y) | Loaded Micelle Size (nm) | Loaded Micelle PDI | Loading level (wt %) | Loading efficiency (%) |
|---|---|---|---|---|---|---|---|---|
| 11 | PTX-Polymer(0:67) | 3 | 0 | 67 | 142 ± 52 | 0.49 ± 0.17 | 5.0 ± 2.7 | 27.6 ± 7.8 |
| 12 | PTX-Polymer(11:0) | 3 | 11 | 0 | 115 ± 9 | 0.13 ± 0.03 | 3.8 ± 0.3 | 23.3 ± 3.6 |
| 13 | PTX-Polymer(8:8) | 3 | 8 | 8 | 131 ± 9 | 0.45 ± 0.08 | 9.2 ± 0.8 | 38.8 ± 5.0 |
| 14 | PTX-Polymer(11:30) | 3 | 11 | 30 | 36 ± 1 | 0.07 ± 0.01 | 15.0 ± 1.8 | 56.8 ± 0.3 |
| 15 | PTX-Polymer(18:55) | 3 | 18 | 55 | 200 ± 44 | 0.22 ± 0.03 | 8.4 ± 2.4 | 25.5 ± 0.3 |

TABLE 10

| Example | Loaded Micelle | Initial CYC (mg) | Units of Chol-MTC (x) | Units of TMC (y) | Loaded Micelle Size (nm) | Loaded Micelle PDI | Loading level (wt %) | Loading efficiency (%) |
|---|---|---|---|---|---|---|---|---|
| 16 | CYC-Polymer(0:30) | 3 | 0 | 30 | 125 ± 18 | 0.39 ± 0.02 | 7.9 ± 1.6 | 31.9 ± 3.8 |
| 17 | CYC-Polymer(11:0) | 3 | 11 | 0 | 123 ± 0.3 | 0.20 ± 0.01 | 12.7 ± 0.4 | 51.3 ± 4.7 |
| 18 | CYC-Polymer(11:30) | 3 | 11 | 30 | 36 ± 0.2 | 0.04 ± 0.01 | 16.8 ± 2.6 | 60.6 ± 3.7 |

TABLE 11

| Example | Loaded Micelle | Initial CYC (mg) | Units of Chol-MTC (x) | Units of TMC (y) | Loaded Micelle Size (nm) | Loaded Micelle PDI | Loading level (wt %) | Loading efficiency (%) |
|---|---|---|---|---|---|---|---|---|
| 19 | SPL-Polymer(0:30) | 3 | 0 | 30 | 112 ± 24 | 0.43 ± 0.01 | 3.7 ± 0.3 | 11.9 ± 1.6 |

TABLE 11-continued

| Example | Loaded Micelle | Initial CYC (mg) | Units of Chol-MTC (x) | Units of TMC (y) | Loaded Micelle Size (nm) | Loaded Micelle PDI | Loading level (wt %) | Loading efficiency (%) |
|---|---|---|---|---|---|---|---|---|
| 20 | SPL-Polymer(11:0) | 3 | 11 | 0 | 102 ± 2 | 0.16 ± 0.01 | 4.3 ± 0.2 | 14.3 ± 0.9 |
| 21 | SPL-Polymer(11:30) | 3 | 11 | 30 | 37 ± 1 | 0.08 ± 0.02 | 4.9 ± 1.1 | 14.4 ± 6.4 |

Overall, an initial amount of PTX of 3 mg produced loaded micelles having a particle size (i.e., average circular cross-sectional diameter) in a range of 36 nm to 200 nm (Examples 11 to 15, Table 9). The optimization studies of the fabrication conditions for the loaded micelle show that stirring conditions had less influence on the particle size than the temperature at which the loaded micelles were prepared. Hence, the particles were formed solely based on slow diffusion and solvent exchange. Particle sizes less than 200 nm are attractive for drug delivery because the particles are less susceptible to clearance by the reticuloendothelial system (RES), and have a more favorable biodistribution into tumor tissues through the enhanced permeability and retention (EPR) effect. This passive targeting phenomenon is attributed to two factors: the disorganized and leaky tumor vasculature which leads to hyperpermeability to macromolecules, and at the same time, tumor tissues have poor lymphatic drainage, which prevents escape of these macromolecules after entry. In greater detail, tumor vessels are highly disorganized, defective or leaky having gap sizes of 100 nm to 2 micrometers. This allows nanoparticles to escape easily from the blood stream and accumulate within tumors. Furthermore, re-entry back into the bloodstream is prevented by the defective lymphatic drainage in the tumor.

Under the same fabrication conditions, copolymers prepared from a mixture of Chol-MTC and TMC (Examples 13 to 15, Table 9) had significantly higher drug loading capacities compared to the loading capacities of the block copolymer formed with TMC alone (Example 11, PTX-Polymer(0:67)), or the block copolymer prepared with Chol-MTC alone (Example 12, PTX-Polymer(11:0)). The combination of TMC and Chol-MTC in the block copolymer provided increased loading efficiency (%), especially at higher x:y ratios (compare Examples 11 and 12 to Examples 13 and 14, Table 9). Lower PTX loading level (wt %), lower loading efficiency (%), and larger particle size were observed with Example 15 (PTX-Polymer(18:55)), attributed to precipitation of the polymer and/or PTX during the dialysis process.

Figure 4A:
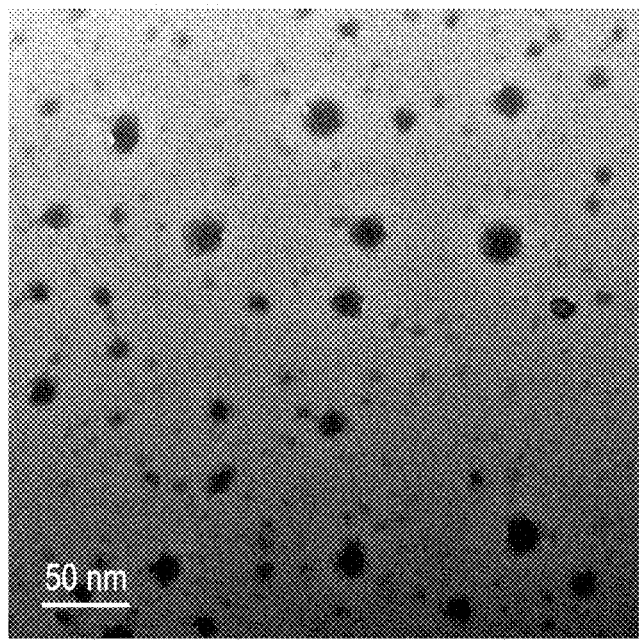
FIGS. 4A to 4E are TEM images of paclitaxel loaded micelles (PTX-loaded micelles) of Examples 11 to 15.
Figure 4B:
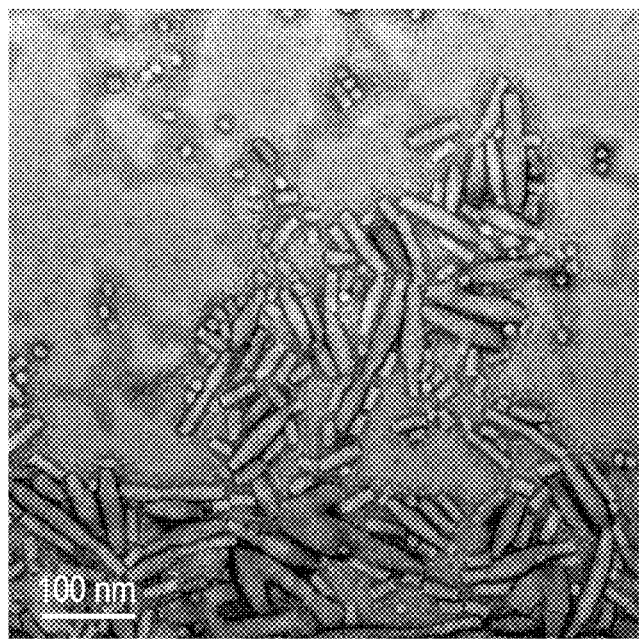
Figure 4C:
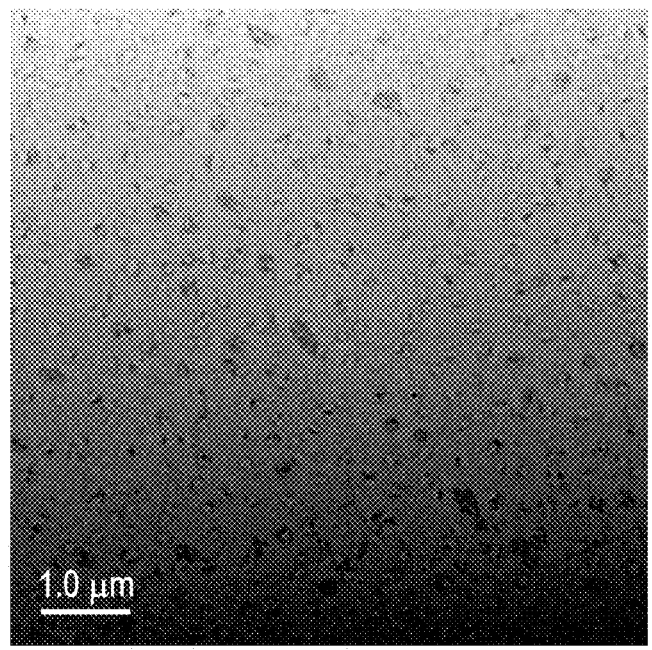
Figure 4D:
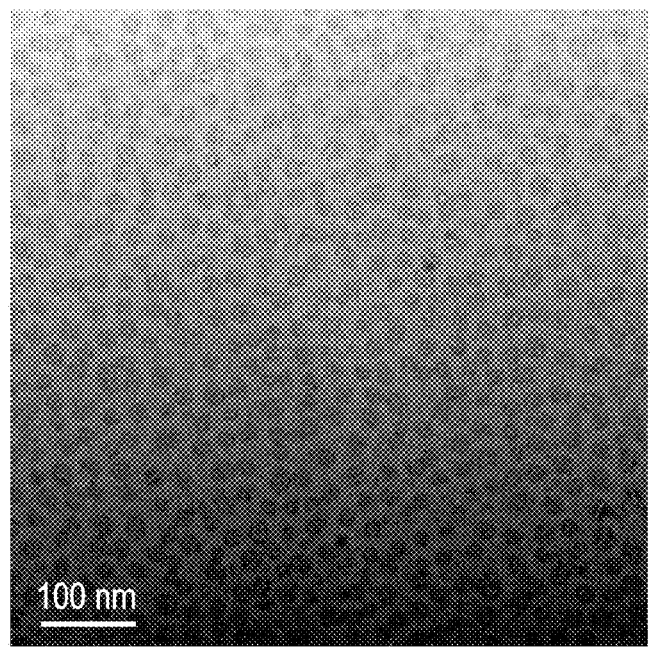
Figure 4E:
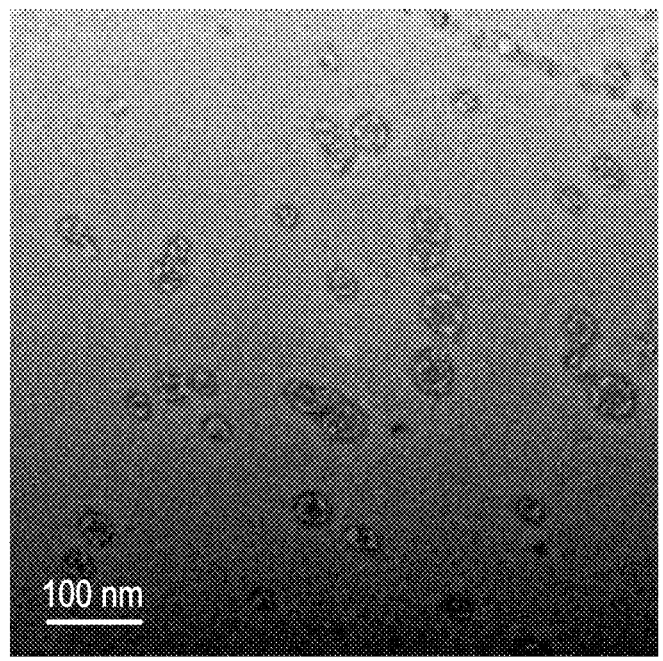

FIGS. 4A to 4E are TEM images of loaded micelles formed by Example 11 (PTX-Polymer(0:67), FIG. 4A), Example 12 (PTX-Polymer(11:0), FIG. 4B), Example 13 (PTX-Polymer(8:8), FIG. 4C), Example 14 (PTX-Polymer(11:30), FIG. 4D), and Example 15 (PTX-Polymer(18:55), FIG. 4E), respectively. When Chol-MTC was used alone in the ring opening polymerization (Example 12, FIG. 4B), the resulting block copolymer self-assembled into cylindrical columns about 20 nanometers wide. The columns comprised a stack of discs, each disc having a height of about 5 nanometers; thus, a stack of 9 discs corresponds to a cylindrical column length of about 45 nanometers. When Chol-MTC was copolymerized with TMC, discrete spherical nanostructures were formed (Examples 13 to 15, FIGS. 4C to 4E, respectively) having an average diameter of about 50 nm to about 100 nm.

In Vitro Release Studies

Release of drugs from the drug-loaded nanoparticles (Examples 11 to 15) was studied using the dialysis method. A dialysis membrane tube with MWCO of 2000 Da (Spectrum Laboratories, U.S.A.) containing 2 ml of the micelles was immersed in 40 ml of the release medium (i.e., PBS at pH 7.4) containing 0.1% (v/v) TWEEN 80 (sold by ICI Americas, Inc.) to maintain a sink condition. This was kept shaking on an orbital shaker at 120 rpm at 37° C. At designated time intervals (1, 7, 24, 31, 48, 55, 120 and 144 hours), the release medium was removed and replaced with fresh medium. The collected medium was analyzed for its drug content. To do this, 10 ml of dichloromethane (DCM) was added and mixed with the release medium through 3 minutes of vigorous mixing. The organic layer was allowed to settle and was carefully extracted into a new vial. DCM was evaporated by air flow. The deposited drug was dissolved in 4 ml of mobile phase consisting of 20 mM ammonium acetate in water:methanol:acetonitrile in the volume ratio of 35:20:45. Drug content was analyzed using high performance liquid chromatography (HPLC, Waters 996 PDA detector, U.S.A.) at 228 nm UV wavelength.

Figure 5A:
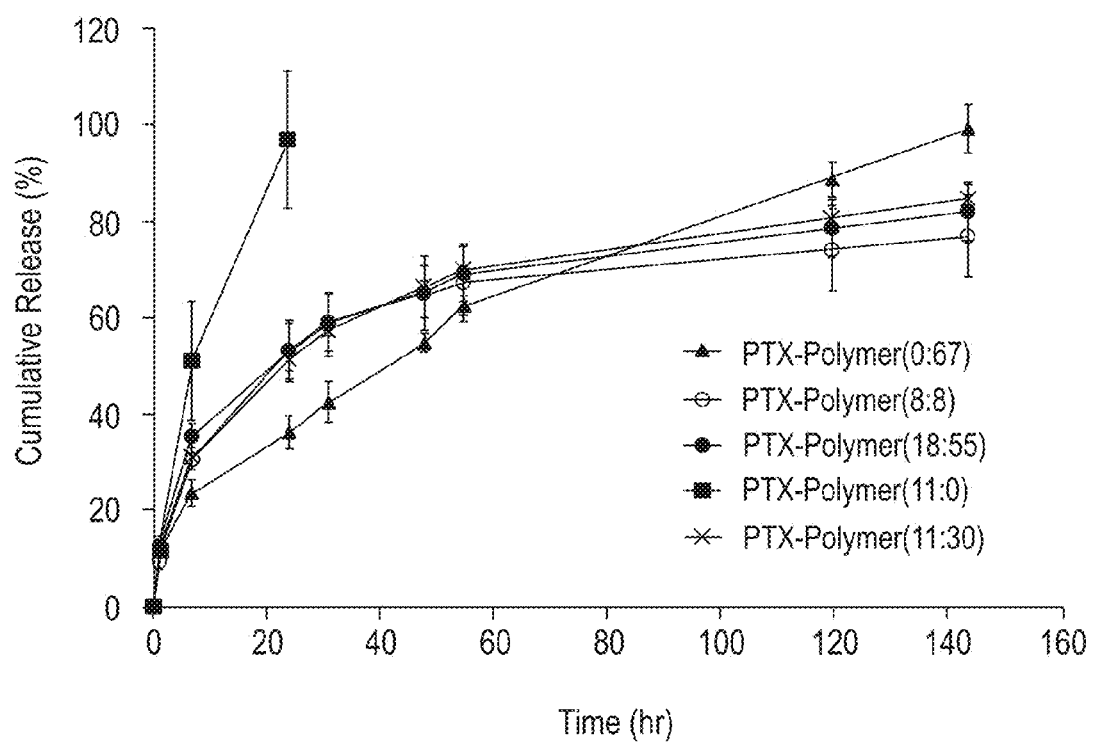
FIG. 5A is a graph showing the cumulative release of PTX from the PTX-loaded micelles (Examples 11 to 15, Table 9) with time. Approximately 100% of the PTX was released within 24 hours from loaded micelles PTX-Polymer(11:0) (Example 12). PTX release was more sustained with the remaining loaded micelles (Example 11, and Examples 13 to 15), displaying 70% to 95% release by 144 hours.
Figure 5B:
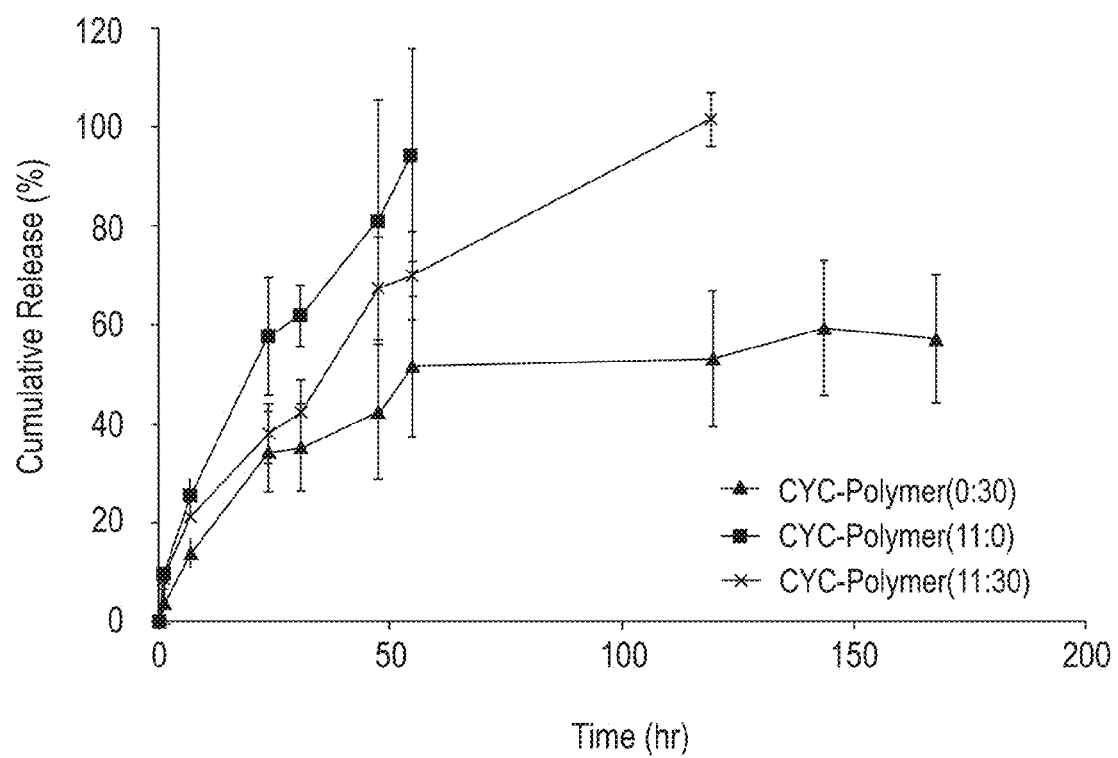
FIG. 5B is a graph showing the cumulative release of the drug cyclosporin A (CYC) from the CYC-loaded micelles (Examples 16 to 18, Table 10) with time. CYC release was sustained from micellar formulation CYC-Polymer(11:30), Example 18, for about 5 days.
Figure 5C:
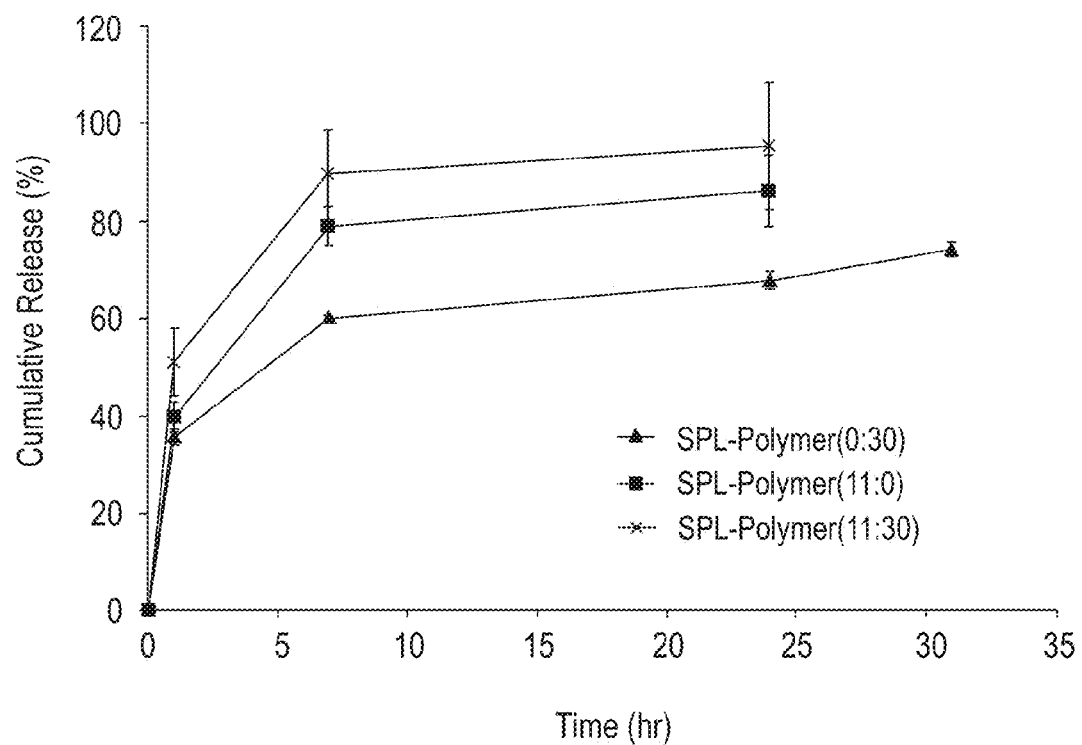
FIG. 5C is a graph showing the cumulative release of the drug spironolactone (SPL) from the SPL-loaded micelles (Examples 19 to 21, Table 11) with time. SPL release from micellar formulation SPL-Polymer(11:30), Example 21, was sustained for about 7 hours.

FIGS. 5A to 5C are graphs showing the cumulative release of PTX, CYC and SPL, respectively, with time. Approximately 100% of the PTX was released from PTX-Polymer (11:0) micelles (Example 12, FIG. 5A) within 24 hours. About 60% of the PTX was released by 48 hours, and was sustained for more than 6 days from the remaining PTX loaded micelles (Examples 11, 13, 14 and 15, FIG. 5A). For CYC, drug release was sustained from the micellar formulation (CYC-Polymer(11:30), Example 18) for about 5 days (FIG. 5B). SPL release from the micellar formulation (SPL-Polymer(11:30), Example 21) was sustained for about 7 hours (FIG. 5C).

Killing Efficiency of Tumor Cells by PTX-Loaded Micelles

Figure 6:
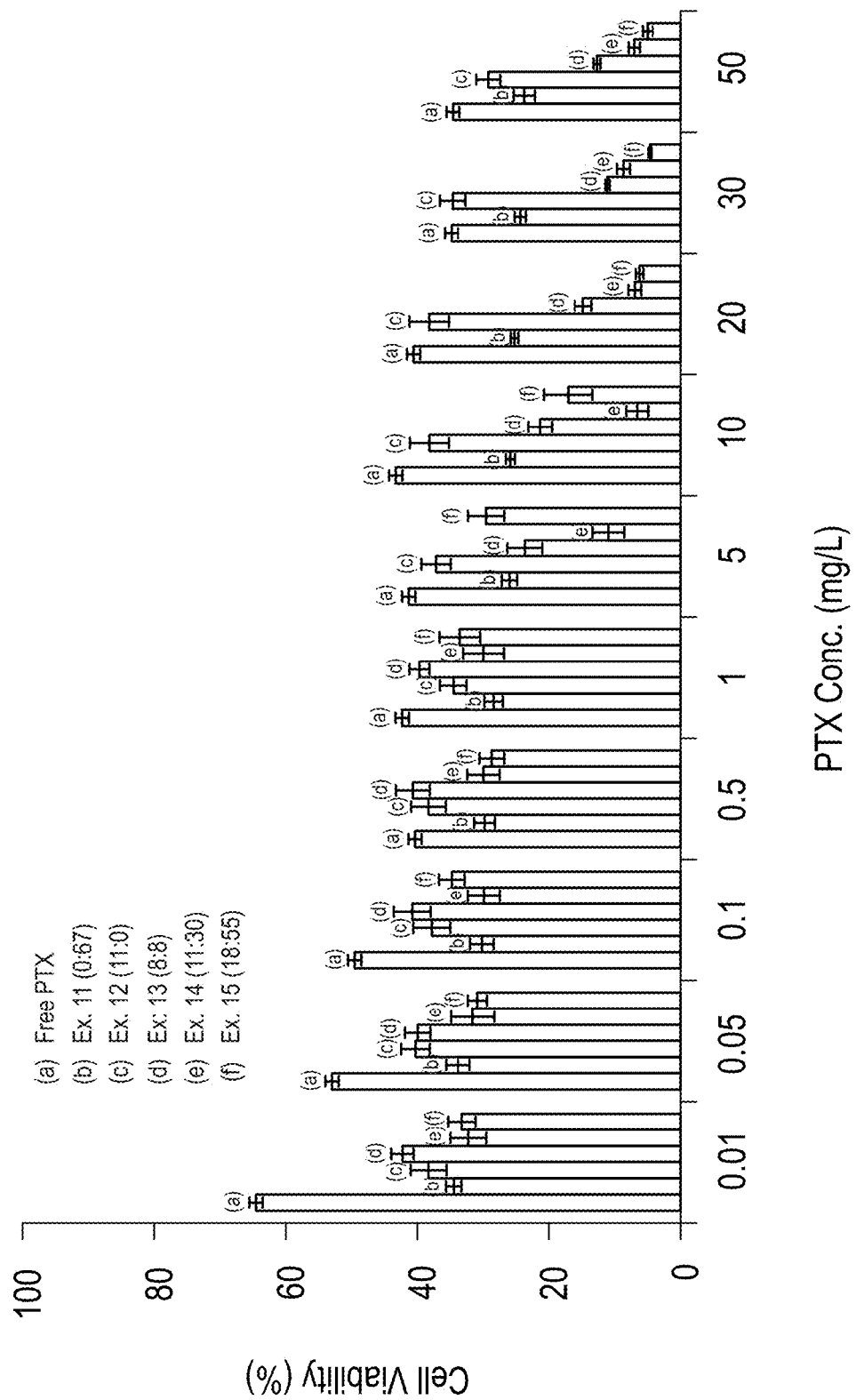
FIG. 6 is a bar chart comparing the viability of HepG2 cells after incubation with PTX-loaded micelles (Examples 11 to 15) and PTX alone for 48 hours at various PTX concentrations. The loaded micelle PTX-Polymer(8:8) (Example 13) killed HepG2 cells more efficiently than the free PTX at most PTX concentrations. A similar trend was observed with loaded micelle PTX-Polymer(11:0) (Example 12) at low PTX concentrations. The killing efficiency of loaded micelles PTX-Polymer(0:67) (Example 11), PTX-Polymer(11:30) (Example 14), and PTX-Polymer(18:55) (Example 15) against HepG2 cells was greater than free PTX at all concentrations tested.

Killing efficiency of HepG2 cells by PTX-loaded micelles (Examples 11 to 15) was studied according to the protocol described above for the block copolymers alone. FIG. 6 is a bar chart comparing viability of HepG2 cells after incubation for 48 hours with PTX loaded micelles (Examples 11 to 15) and free PTX (PTX not bound to a polymer) at various PTX concentrations. The PTX loaded micelles had better killing efficiency than the free PTX alone at all PTX levels. As described above (see also FIG. 3) the polymers alone were not cytotoxic against HepG2 cells. Therefore, the decrease in cell viability after 48 hours incubation with PTX or PTX-loaded micelles can be attributed to PTX released from the micelles. The loaded micelle PTX-Polymer(8:8) (Example 13) killed HepG2 cells more efficiently than the free PTX at most PTX concentrations. A similar trend was observed with loaded micelle PTX-Polymer(11:0) (Example 12) at low PTX concentrations. The killing efficiency of loaded micelles PTX-Polymer(0:67) (Example 11), PTX-Polymer(11:30) (Example 14), and PTX-Polymer(18:55) (Example 15) against HepG2 cells was greater than free PTX at all concentrations tested. These findings show that a PTX-loaded nanoparticulate formulation was more efficient than free PTX in killing HepG2 cells.

The above examples demonstrate that hydrophobic cholesterol-functionalized cyclic carbonate monomers, such as Chol-MTC, allow for efficient incorporation of cholesterol groups into a copolymers via metal-free organocatalytic ring opening polymerization, particularly when copolymerized with a diluent cyclic carbonyl monomer such as TMC. Amphiphilic, biocompatible and/or biodegradable block copolymers can be formed using a mono-endcapped poly (alkylene glycol) initiators for the ring opening polymerization. The cholesterol functionalized block copolymers have low CMCs, and have high loading capacity for extremely hydrophobic and/or rigid drugs. The encapsulation of the drug can be accomplished via self-assembly without sonication or homogenization using the above described dialysis techniques. Consequently, these polymeric materials are promising nanocarriers for delivery of hydrophobic anticancer drugs such as PTX and other drugs with similar ring structures such as CYC and SPL.

ABA Triblock Copolymer Preparation

Several ABA triblock copolymers were prepared by a transition-metal free organocatalytic ring opening polymerization reaction using poly(ethylene glycol) (PEG) as a macro-initiator and cholesteryl functionalized cyclic carbonate monomer (Chol-MTC) according to Scheme 3. Subscripts n' and m of Scheme 3 are listed in Table 12 below.

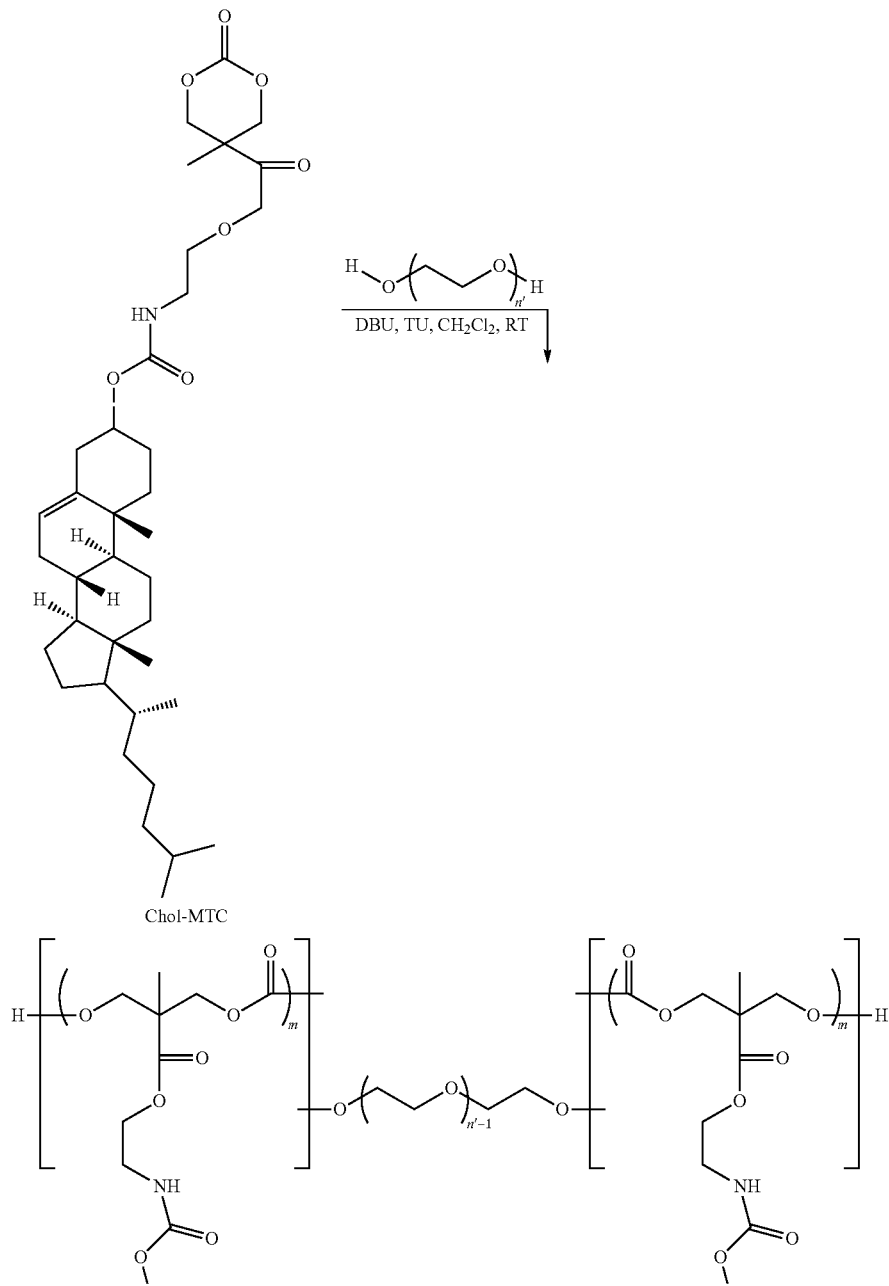

Scheme 3.

-continued

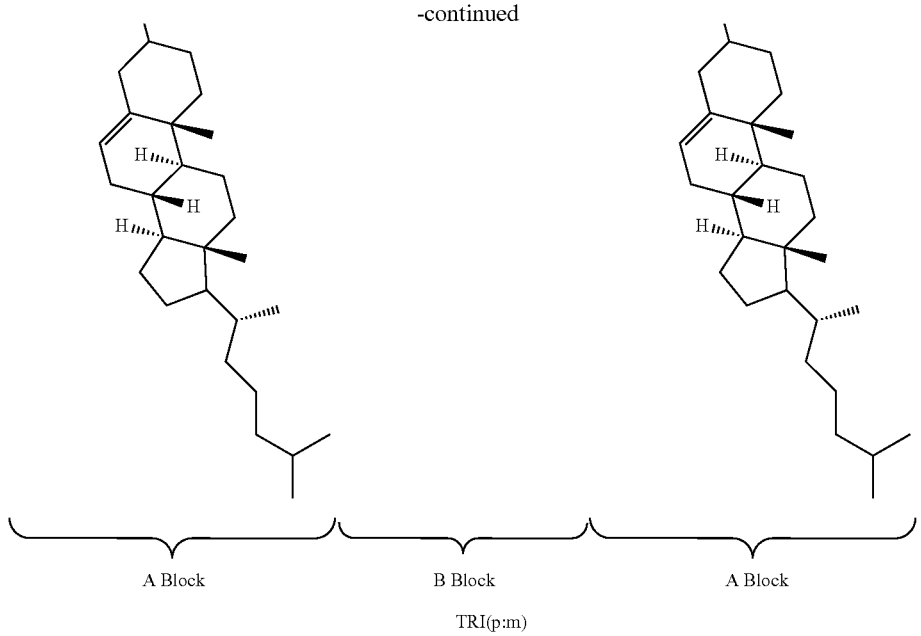

TRI(p:m)

In the notation TRI(p:m) of Scheme 3, p represents the two digits of the PEG name (e.g., p=20 for PEG20) used to form block B, and m represents the average degree of polymerization of the cholesteryl repeat unit of block A.

The following procedure to prepare TRI(20:2.2) (Example 25 below) is representative. In a 7 mL vial containing a magnetic stir bar in the glove box, Chol-MTC (135 mg, 219 micromoles, 8.6 equivalents), PEG20 (20 kDa, 509 mg, 25.6 micromoles, 1.0 equivalent) and TU (8.0 mg, 21.6 micromoles, 0.8 equivalents) were dissolved in dichloromethane (2.0 mL). To this solution, DBU (3.1 microliters, 3.2 mg, 20.8 micromoles, 0.8 equivalents) was added to initiate polymerization. The reaction mixture was allowed to stir at room temperature and aliquots of samples were taken to monitor the monomer conversion and evolution of molecular weight by $^1$H NMR spectroscopy and SEC. After 100 minutes, the reaction was quenched by the addition of about 10 mg of benzoic acid and was precipitated into ice-cold diethyl ether (2×50 mL). The polymer was dried in a tared vial for about 1 to 2 days, until a constant sample mass was obtained as white powder (470 mg, 73%).

Table 12 lists the properties of the ABA triblock copolymers. The weight percent of the PEG chain in the ABA triblock copolymer, $f_{PEG}$, was calculated according to the equation:

$$f_{PEG} = \{Mn^{PEG}/(Mn^{PEG}+[2 \times m \times 616])\} \times 100\%$$

where $Mn^{PEG}$ is the number average molecular weight of the PEG initiator, and m is the average degree of polymerization of the cholesteryl repeat unit of block A.

TABLE 12

| Example | Triblock Name | PEG Name | PEG DP (n')[b] | Chol DP (m)[c] | $f_{PEG}$[d] (%) |
|---|---|---|---|---|---|
| 22 | TRI(10:1.5) | PEG10 | 247 | 1.5 | 84.8 |
| 23 | TRI(10:1.9) | PEG10 | 247 | 1.9 | 81.0 |
| 24 | TRI(20:0.8) | PEG20 | 452 | 0.8 | 95.2 |

TABLE 12-continued

| Example | Triblock Name | PEG Name | PEG DP (n')[b] | Chol DP (m)[c] | $f_{PEG}$[d] (%) |
|---|---|---|---|---|---|
| 25 | TRI(20:2.2) | PEG20 | 452 | 2.2 | 87.9 |
| 26 | TRI(35:2.4) | PEG35 | 795 | 2.4 | 92.2 |

[a]number average molecular weight data from the supplier.
[b]Average degree of polymerization of the ethylene oxide repeat unit of the B block (calculated).
[c]Average degree of polymerization of the cholesteryl repeat unit of block A based on $^1$H NMR spectroscopy.
[d]Weight percent of PEG chain of the ABA triblock copolymer.

Thus, the A blocks of the ABA triblock copolymers in Table 12 had 0.8 to 2.4 repeat units derived from Chol-MTC.

The PEG macroinitiators varied in weight average molecular weight of 10 kDa to 35 kDa. The overall hydrophilicity of the polymers, as measured by the weight percent of PEG, $f_{PEG}$, of the ABA triblock copolymer, was about 85% to about 95%. In some instances, the resultant polymers could be directly solubilized in aqueous solutions, if necessary with mild sonication/vortexing as an aid.

Critical Micelle Concentration (CMC) of ABA Triblock Copolymers

Figure 7:
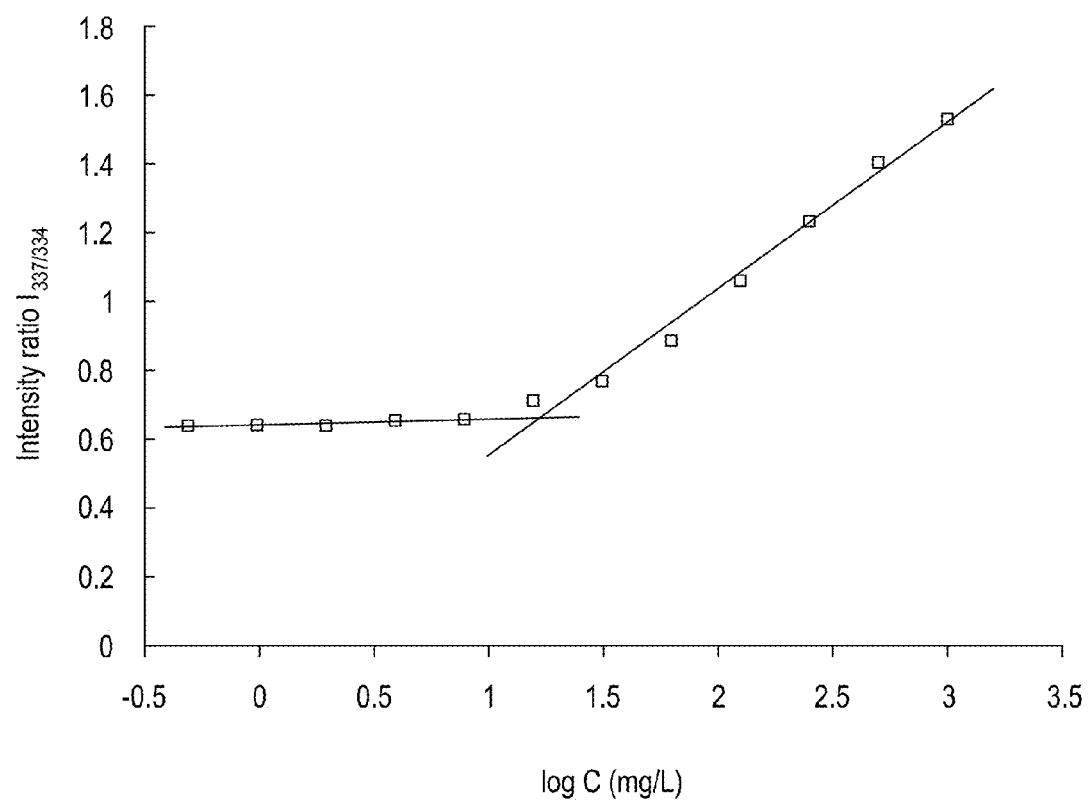
FIG. 7 is a graph of intensity ratio (1337/1334) vs. logarithm of concentration (mg/L) of TRI(35:2.4) in DI water.

In some instances, the ABA triblock copolymers were able to self-assemble to form micelles in aqueous environment. For example, in DI water TRI(35:2.4) has a CMC of 16.6 mg/L (FIG. 7, graph). For comparison, diblock copolymer Polymer(11:30) has a CMC of 1.5 mg/L (FIG. 1. These values indicates the triblock copolymers can have a strong propensity for micelle formation, and that the micellar structure of the polymers can exist even at extensively dilute conditions, and possibly the conditions of body fluids.

Preparation of FITC Loaded Micelles

Example 27

Fluorescein isothiocyanate (FITC) was used as a model for incorporating a biologically active substance in a composite hydrogel. 15 mg of Polymer(11:30) and 3 mg of FITC were dissolved together in 2 mL DMF. The mixture was placed in a dialysis membrane tube with molecular weight cut-off (MWCO) of 1000 Da (Spectrum Laboratories, U.S.A.). The dialysis bag was then immersed in 1 L of de-ionized (DI) water at 4° C. for 2 days. During the 2-day course, the dialysis medium was replaced after 3, 6, and 24 hours. At the end of the dialysis process, the resulting micelle solution was centrifuged at 4000 rpm for 5 minutes to remove large aggregates. The particle size and zeta potential of the micelles was then measured using a Zetasizer with dynamic light scattering capability (scattering angle: 90°) and equipped with a He—Ne laser beam at 658 nm (Malvern Instruments Zetasizer Nano ZS, UK).

FITC Loading Measurements

To determine the encapsulation efficiency of FITC in Polymer(11:30) micelles, the micelle suspension was mixed with DMSO (1:1) and the fluorescence intensity was measured at Ex/Em 485/528 nm using a fluorescence spectrofluorometer (Horiba Scientific, Japan). The encapsulation efficiency was calculated based on the ratio of the amount of FITC successfully encapsulated into the micelles to the amount of FITC initially added during the micelle fabrication process. Table 13 lists the properties of the FITC loaded micelle.

TABLE 13

| Example | Loaded Micelle | Initial FITC (mg) | Units of Cholesteryl MTC (x) | Units of TMC (y) | Loaded Micelle Size (nm) | Loaded Micelle PDI | Loading level (wt %) | Loading efficiency (%) |
|---|---|---|---|---|---|---|---|---|
| 27 | FITC-Polymer(11:30) | 3 | 11 | 30 | 33 ± 0.4 | 0.08 ± 0.01 | 19.5 | 59.2 |

Formation of Composite Hydrogels

Hydrogels at known concentrations (4 wt % to 8 wt %) were prepared by dissolving the ABA triblock copolymers in either deionized water or loaded micelle solution at 25° C. for 4 hours. For polymers having a shorter PEG chain (10 kDa-20 kDa), ultrasonication was necessary to ensure complete dissolution.

For the formation of composite hydrogel containing FITC, 1 ml of the loaded micelle suspension containing 0.36 mg/ml of FITC (Example 27) was used to dissolve solid TRI(35:2.4) (40 mg). The resultant hydrogel was transferred to dialysis membrane tubes with molecular weight cutoff (MWCO) of 1000 Da (Spectrum Laboratories, U.S.A.). The tubes were immersed in 20 ml of the release medium (i.e., PBS pH 7.4) and kept shaking on an orbital shaker at 100 rpm at 37° C. At various time intervals, the release medium was removed and replaced with fresh medium.

Composite hydrogels were also prepared using CYC-loaded micelles prepared with Polymer(11:30) (Example 18). The concentration of the Polymer(11:30) and cyclosporine A in the micelle solution was 0.18% and 0.036% respectively.

Table 14 lists the hydrogels and composite hydrogels formed.

TABLE 14

| Example | Triblock Polymer (A) | Loaded Micelle (B) | Wt % A | Wt % B | Total Solids Conc. (wt %) |
|---|---|---|---|---|---|
| 28 | TRI(20:2.2) | | 100 | 0 | 5 |
| 29 | TRI(20:2.2) | | 100 | 0 | 8 |
| 30 | TRI(35:2.4) | FITC-Polymer (11:30) | 95.9 | 4.1 | 4 |
| 31 | TRI(35:2.4) | | 100 | 0 | 4 |
| 32 | TRI(35:2.4) | CYC-Polymer (11:30) | 95.9 | 4.1 | 4 |

Preparation of Free-FITC Loaded Hydrogel

Example 33

FITC was loaded directly into triblock copolymer TRI(35:2.4) without the diblock copolymer using the following procedure. FITC and TRI(35:2.4) was mixed together in the presence of deionized water to form hydrogel with FITC concentration of 0.36 mg/ml in 4 wt % hydrogel.

Rheological Experiments

The rheological analysis of the hydrogels was performed on an ARES-G2 rheometer (TA Instruments, USA) equipped with a plate-plate geometry of 8 mm diameter. Measurements were taken by equilibrating the gels at 25° C. and 37° C. between the plates at a gap of 1.0 mm. The data were collected under controlled strain of 0.2 or 0.6% and a frequency scan of 1.0 to 100 rad/s. Gelation properties of the polymer suspension was monitored by measuring the shear storage modulus (G'), as well as the loss modulus (G''), at each point. For shear-thinning studies, the viscosity of the hydrogels was monitored as function of shear rate from 0.1 to 10 s$^{-1}$.

Figure 8:
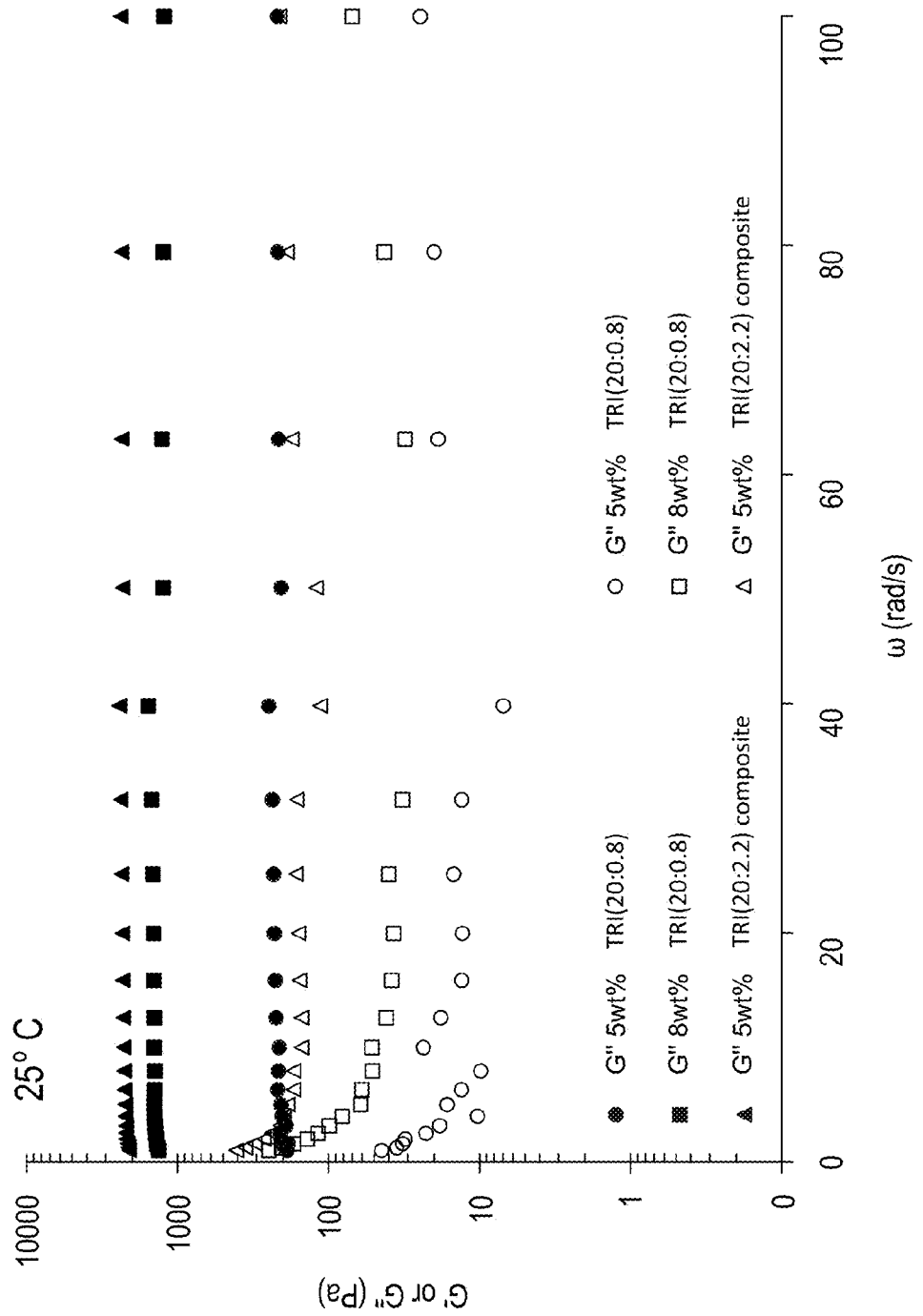
FIG. 8 is a graph of the frequency sweep of storage (G') and loss (G") moduli at 25° C. of triblock copolymer TRI(20:0.8) at 5 wt % and 8 wt % concentration in DI water, and composite hydrogel formed with TRI(20:2.2) at 5 wt % concentration.

The influence of ABA copolymer concentration on storage modulus G' is shown FIG. 8. An 8 wt % mixture of TRI(20:0.8) in deionized (DI) water (Example 29) has a storage modulus G'=2000 Pa, nearly 10-fold higher compared to a 5 wt % mixture of TRI(20:0.8) (G'=200 Pa) (Example 28).

A slight increase in the cholesteryl repeat units from 0.8 to 2.2 drastically changes the solubility of the ABA triblock copolymers. TRI(20:2.2) has no visible solubility in DI water at 5 wt %, even after overnight sonication. However, the insolubility can be reversed by dissolving the ABA triblock copolymer using the CYC loaded micelle suspension (Example 18) in place of DI water.

The 5 wt % composite hydrogel formed with TRI(20:2.2) (Example 30) had a higher storage modulus at 25° C. (G'=2300 Pa) compared to a 5 wt % hydrogel of TRI(20:0.8) (Example 28) alone (G'=400 Pa) (FIG. 8).

Figure 9:
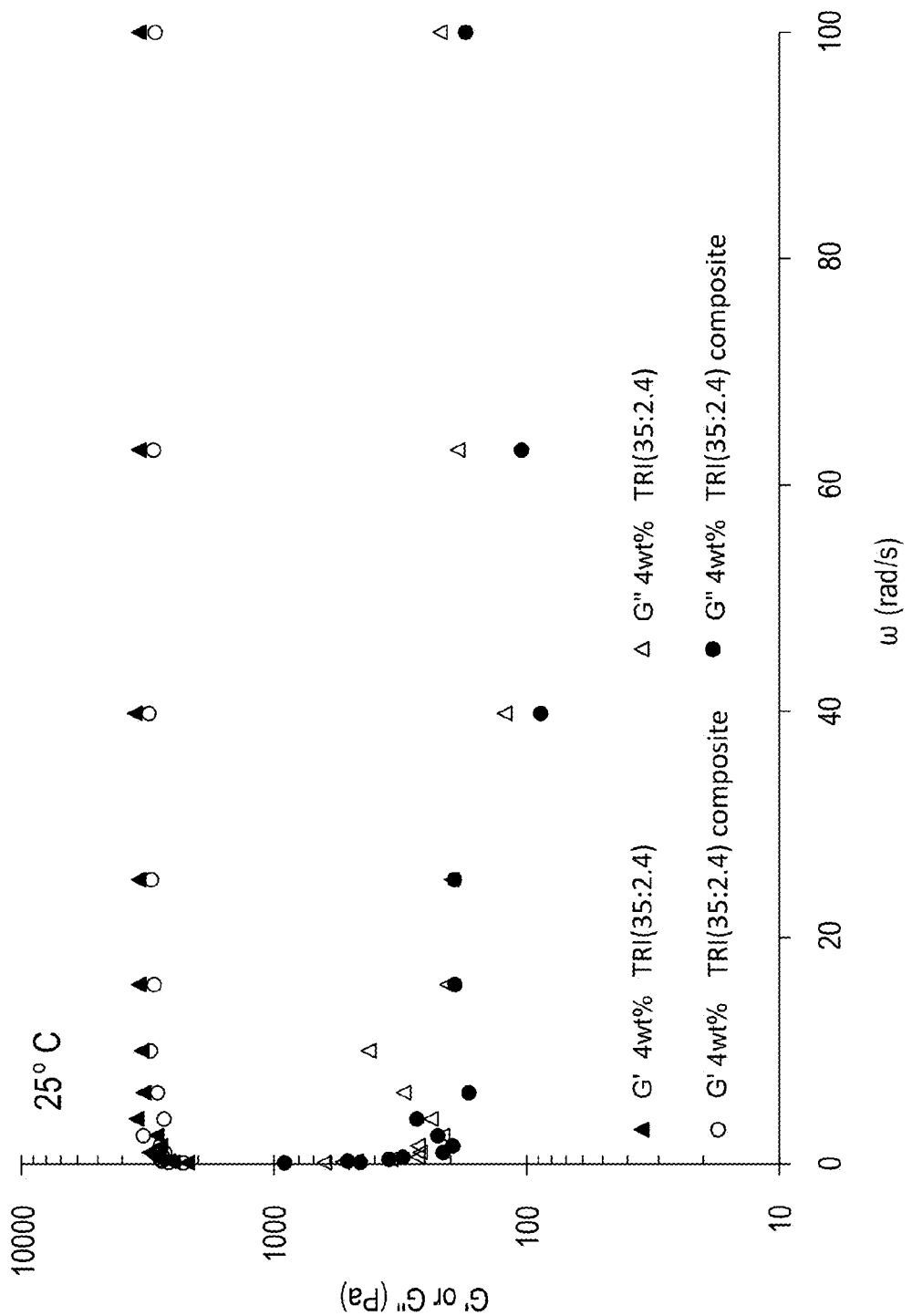
FIG. 9 is a graph of the frequency sweep of storage (G') and loss (G") moduli at 25° C. of triblock copolymer TRI(35:2.4) at 4 wt % concentration in DI water, and composite hydrogel formed with TRI(35:2.4) at 4 wt % concentration

Improvement in solubility of the ABA triblock copolymers was also observed by increasing the PEG block from 20 kDa to 35 kDa. For instance, 4 wt % of TRI(35:2.4) (Example 31) was able to dissolve within 4 hours when left standing at 25° C. without sonication. A 4 wt % solution of TRI(35:2.4) (Example 31) also formed hydrogel having a higher storage modulus at 25° C. (G'=3500 Pa) (FIG. 9) compared to 5 wt % composite hydrogel of TRI(20:2.2) (Example 28) at 25° C. (G'=2300 Pa) (FIG. 8). A 4 wt % composite hydrogel of TRI(35:2.4) (Example 32) had a storage modulus G' of about 3000 Pa at 25° C. (FIG. 9).

Dissolution using deionized water or cyclosporin A-loaded micelle suspension (Example 18) did not have a significant influence on the storage and loss modulus of TRI(35:2.4).

Figure 10:
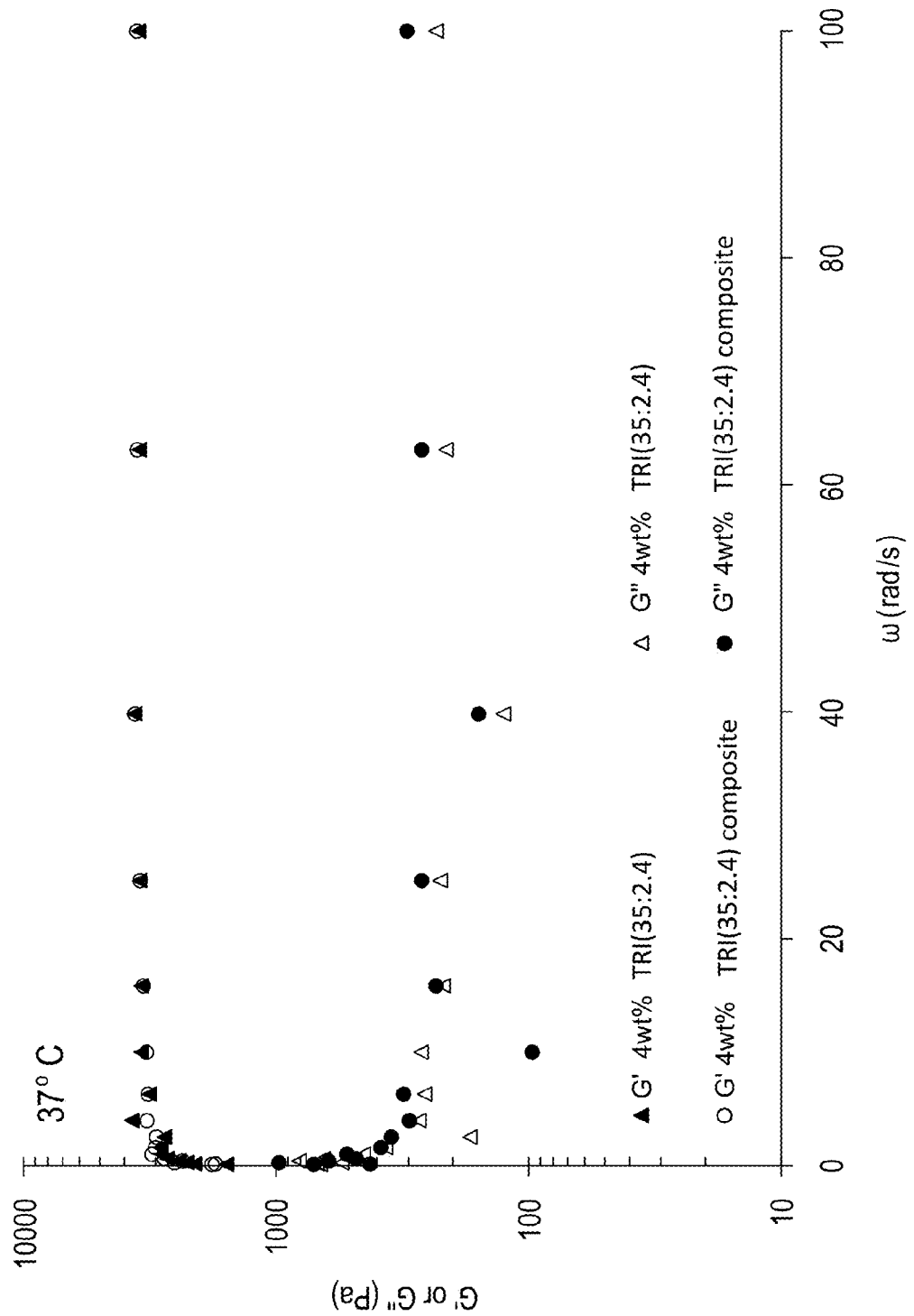
FIG. 10 is a graph of the frequency sweep of storage (G') and loss (G") moduli at 37° C. of triblock copolymer TRI(35:2.4) at 4 wt % concentration in DI water, and composite hydrogel formed with TRI(35:2.4) at 4 wt % concentration.

Effects of temperature were also investigated. There were no changes to the storage modulus (G' 3500 Pa) and loss modulus (G''-150 Pa) of TRI(35:2.4) (Example 31) when temperature was increased from 25° C. (FIG. 9) to 37° C. (FIG. 10).

Figure 11:
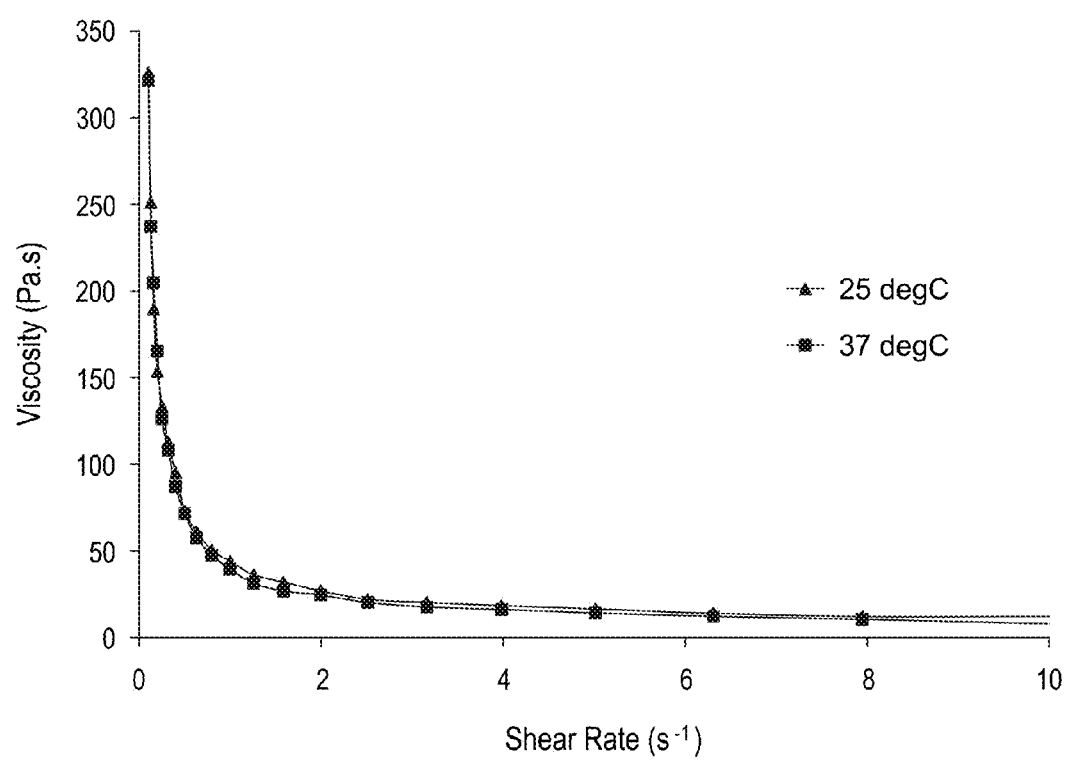
FIG. 11 is a graph of the flow sweep of 4 wt % TRI(35:2.4) at 25° C. and 37° C., demonstrating the shear thinning behavior of the hydrogel.

FIG. 11 shows the reduction in viscosity with increasing shear rate at both 25° C. and 37° C. of a hydrogel formed with 4 wt % TRI(35:2.4) (Example 31). The results indicate the shear-thinning characteristic of the gels, which results from the disruption of physical cross-links between the polymer chains with the application of shear stress.

Scanning Electron Microscope (SEM) Imaging Of Hydrogel

To minimize morphological perturbations, the TRI(35:2.4) hydrogel (Example 31) was cryo-fixed by transferring the sample into a chamber filled with liquid nitrogen. A 2-day freeze-drying process then followed. The morphology of the gel was observed using the scanning electron microscope (SEM) (Jeol JSM-7400F, Japan).

Figure 12:
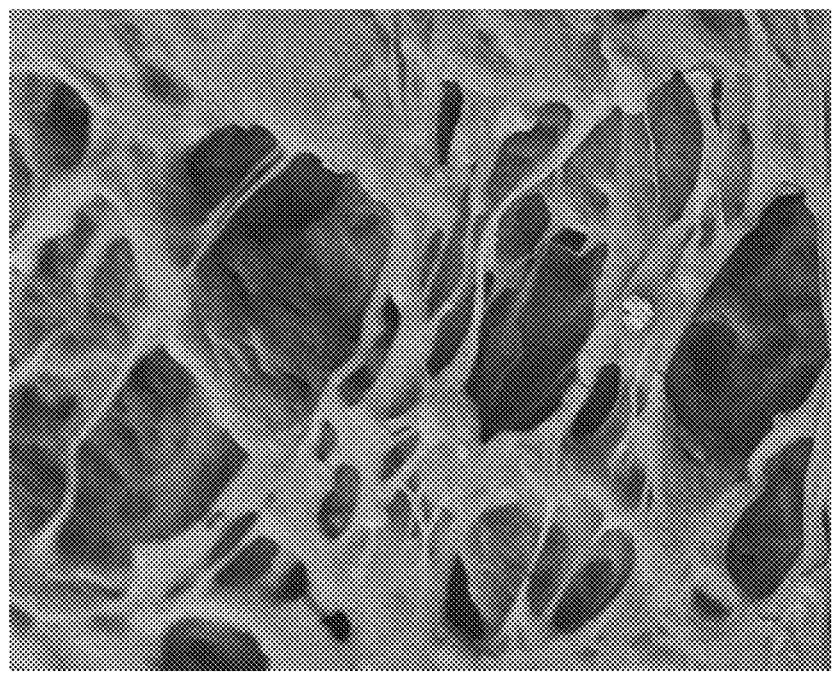
FIG. 12 is an SEM image of cryo-fixed TRI(35:2.4) (4 wt %) hydrogel. The sample was prepared by swelling the polymer with DI water until equilibrium and rapidly transferring into a chamber filled with liquid nitrogen. This was then followed by a 2-day freeze-drying process.
Figure 13:
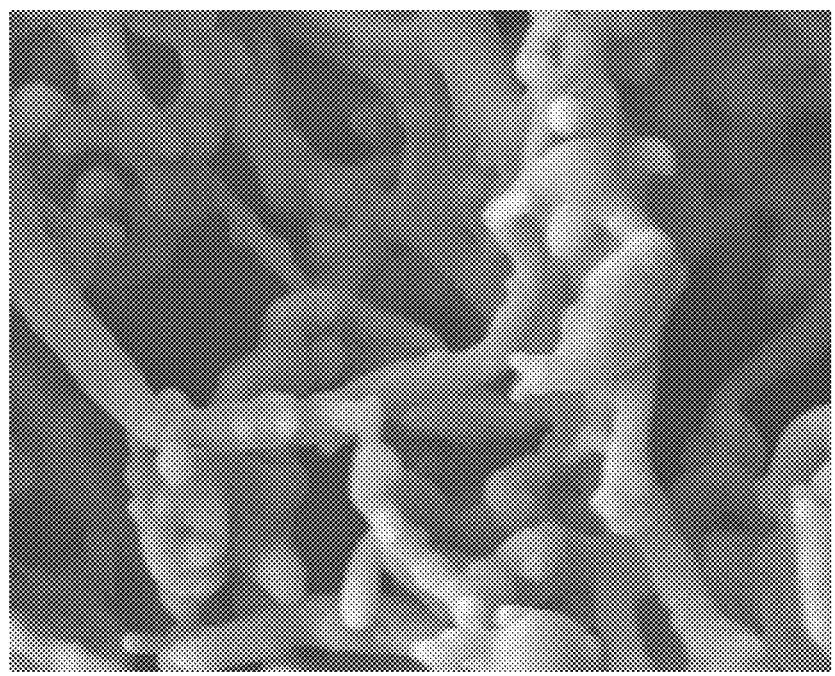
FIG. 13 is an SEM image of cryo-fixed TRI(35:2.4) (4 wt %) hydrogel. The sample was prepared by swelling the Polymer(11:30) micelle suspension not loaded with drug until equilibrium and rapidly transferred into a chamber filled with liquid nitrogen. This was then followed by a 2-day freeze-drying process.

SEM imaging of the TRI(35:2.4) hydrogel (Example 31) formed in DI water (FIG. 12) shows the presence of long flexible fibers, most likely due to the entanglement of the PEG chains. These long flexible fibers vary in diameter (~0.1 to 1 micrometers) with anchors at the interaction sites of cholesteryl units. In contrast, a composite hydrogel of TRI(35:2.4) (Example 32) prepared with CYC loaded Polymer(11:30) (Example 18) has fibers that are shorter and thicker with larger diameters mostly around 2 micrometers (FIG. 13).

In Vitro FITC Release

The release of FITC from the above-described composite hydrogel (Example 30) was studied using the dialysis method. Prior to this, to analyze for the amount of FITC released, the release medium was mixed with DMSO (1:1) and the fluorescence intensity was measured at $E_x/E_m$ 485/528 nm.

Figure 14:
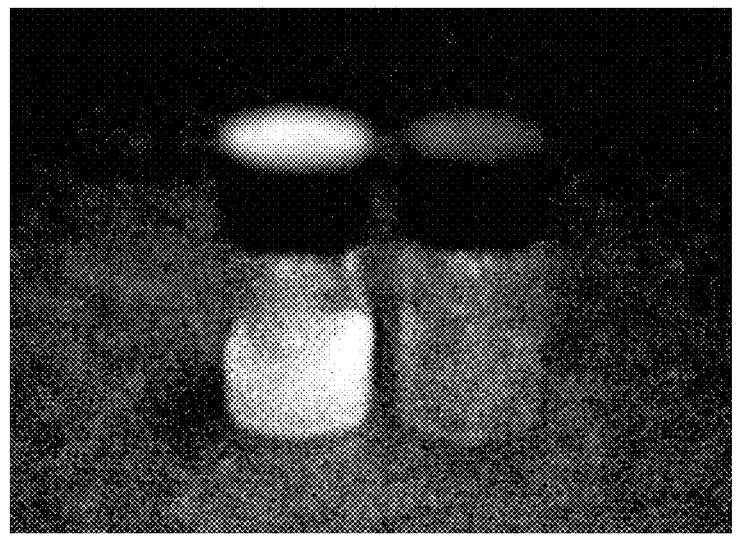
FIG. 14 is a photograph of a composite hydrogel containing fluorescein isothiocyanate (FITC) (left) (Example 30) and free FITC in hydrogel (right) (Example 33). The left side is lighter because of the green fluorescence of FITC. The right side is darker because of the absence of FITC fluorescence. It can be seen that the composite gel containing FITC-loaded micelles (Example 30) was able to fluoresce under UV-illumination at 365 nm, while no fluorescence could be seen from free FITC-containing hydrogel (Example 33). This indicates the difference in solvent microenvironment for FITC which results in changes to its fluorescence characteristics.

From fluorescence measurements, the encapsulation efficiency of FITC in Polymer(11:30) micelles was determined to be 59%. From the photograph of FIG. 14, it can be seen that the composite hydrogel (Example 30) containing the FITC-loaded micelles was able to fluoresce (left vial, lighter shade in FIG. 14) under UV-illumination at 365 nm, while no fluorescence could be seen from a TRI(35:2.4) hydrogel (Example 33) that contained FITC that was not encapsulated in Polymer(11:30) micelles (right vial, darker shade in FIG. 14). This indicates a difference in the solvent microenvironment for FITC, which results in changes to its fluorescence characteristics.

Figure 15:
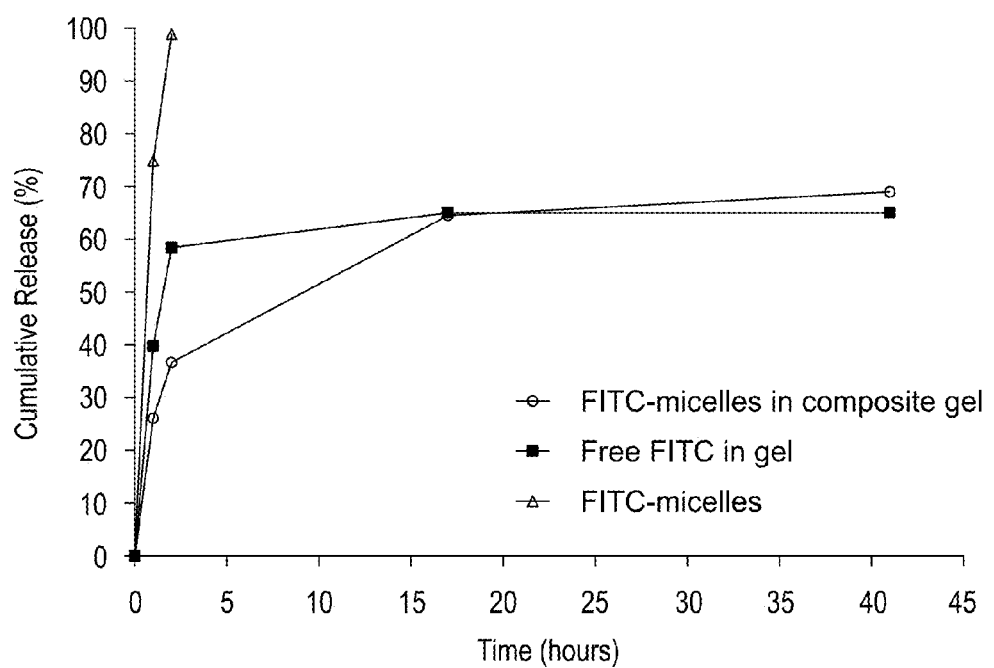
FIG. 15 is a graph showing FITC release as a function of time from various samples: composite hydrogel containing FITC (Example 30), free FITC in hydrogel (Example 33), and FITC-loaded micelles alone (Example 27).

The release of FITC from the composite hydrogel (Example 30) was studied at 37° C. by immersing the gel in phosphate buffered saline (PBS). For comparison, FITC release from FITC loaded micelles (Example 27) and FITC release from the free-FITC loaded TRI(35:2.4) hydrogel (Example 33) were also investigated. From the release profiles (FIG. 15), it can be seen that the composite hydrogel (Example 30) provided greater sustained release of FITC compared to FITC-loaded micelles (Example 27) alone and the free-FITC in TRI(35:2.4) hydrogel (Example 33). About 60% of the drug was released from the composite hydrogel in 17 hours while a similar amount was released from the free-FITC/TRI(35:2.4) hydrogel in 2 hours. Notably, the FITC loaded micelles (Example 27) show an extremely high burst release with 60% of the drug escaping within the first 0.5 hour.

CONCLUSIONS

Cholesteryl-containing biodegradable and biocompatible ABA-type triblock copolymers that form hydrogels at relatively low polymer concentration have been developed. The viscoelastic properties of the hydrogels can be tuned by varying the polymer concentration or composition, thereby providing a storage modulus G' having a value in a range of about 300 Pa to about 3500 Pa. It has been demonstrated that composite hydrogels comprising drug-loaded micelles and a hydrogel forming triblock copolymer can provide sustained release of a hydrophobic drug. These tunable soft-composite gels serve as an attractive candidates for a wide variety of biomedical applications.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A composite hydrogel, comprising:
   an amphiphilic triblock copolymer (ABA), wherein i) the triblock copolymer comprises two independent peripheral hydrophobic A blocks and a hydrophilic central B block, ii) each of the A blocks comprises a steroidal repeat unit (repeat unit 1) comprising both a backbone carbonate and a side chain comprising a steroid functional group, iii) each of the A blocks has a degree of polymerization of about 0.5 to about 4.0, and iv) the B block comprises a first poly(alkylene oxide) backbone; and
   a loaded micelle comprising a biologically active substance and an amphiphilic diblock copolymer (CD), wherein i) the diblock copolymer comprises a hydrophilic C block and a hydrophobic D block, ii) the C block comprises a second poly(alkylene oxide) backbone, and iii) the D block comprises a steroidal repeat unit (repeat unit 2) comprising both a backbone carbonate group and a side chain comprising a steroid functional group;
   wherein the amphiphilic triblock copolymer and the loaded micelle are bound by noncovalent interactions, and the composite hydrogel is capable of controlled release of a biologically active substance.

2. The composite hydrogel of claim 1, wherein at a temperature of 20° C. to 40° C. a 2 wt % to 5 wt % aqueous mixture of the composite hydrogel, based on a total weight of the aqueous mixture, is a gel.

3. The composite hydrogel of claim 1, wherein the triblock copolymer alone is not soluble in water.

4. The composite hydrogel of claim 1, wherein the triblock copolymer alone does not form a hydrogel in water.

5. The composite hydrogel of claim 1, wherein each of the A blocks has a degree of polymerization of about 0.8 to about 2.4.

6. The composite hydrogel of claim 1, wherein each of the A blocks consists essentially of the repeat unit 1.

7. The composite hydrogel of claim 1, wherein the steroid functional group of the repeat unit 1 is a cholesteryl group.

8. The composite hydrogel of claim 1, wherein the steroid functional group of the repeat unit 2 is a cholesteryl group.

9. The composite hydrogel of claim 1, wherein the repeat unit 1 has a structure according to formula (7):

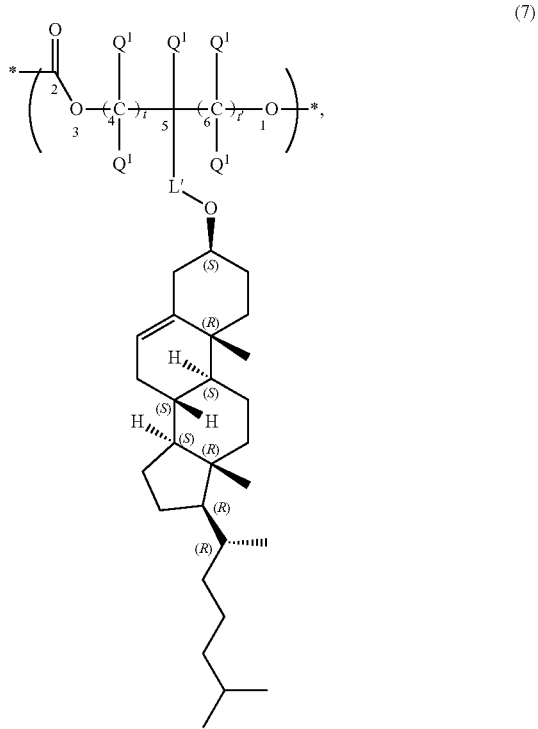

(7)

wherein
- t is an integer having a value of 0 to 6,
- t' is an integer having a value of 0 to 6,
- t' and t cannot both be zero,
- each $Q^1$ is an independent monovalent radical selected from the group consisting of hydrogen, halides, alkyl groups comprising 1 to 30 carbons, and aryl groups comprising 6 to 30 carbon atoms, and
- L' is a divalent linking group comprising one or more carbons.

10. The composite hydrogel of claim 1, wherein the triblock copolymer comprises 5 wt % to 15 wt % of the repeat unit 1 based on a total weight of the triblock copolymer.

11. The composite hydrogel of claim 1, wherein the B block is a divalent poly(ethylene oxide) chain having a number average molecular weight (Mn) of about 10000 to about 35000.

12. The composite hydrogel of claim 1, wherein the C block is a monovalent endcapped poly(ethylene oxide) having a number average molecular weight of about 5000.

13. The composite hydrogel of claim 1, wherein the triblock copolymer has a critical micelle concentration (CMC) in deionized water between 0 mg/L and 20 mg/L.

14. The composite hydrogel of claim 1, wherein the diblock copolymer has a critical micelle concentration (CMC) in deionized water between 0 mg/L and 5 mg/L.

15. The composite hydrogel of claim 1, wherein the biologically active substance is a hydrophobic drug.

16. The composite hydrogel of claim 15, wherein the drug is cyclosporin A (CYC).

17. A method, comprising:

mixing an amphiphilic triblock copolymer (ABA) with a loaded micelle, the loaded micelle comprising i) a biologically active substance and ii) an amphiphilic diblock copolymer (CD), thereby forming a composite hydrogel capable of controlled release of the biologically active substance;

wherein
- the triblock copolymer (ABA) comprises two independent peripheral hydrophobic A blocks and a hydrophilic central B block, wherein i) each of the A blocks comprises a steroidal repeat unit (repeat unit 1) comprising both a backbone carbonate and a side chain comprising a steroid functional group, ii) each of the A blocks has a degree of polymerization of about 0.5 to about 4.0, and iii) the B block comprises a first poly(alkylene oxide) backbone,
- the diblock copolymer (CD) comprises a hydrophilic C block and a hydrophobic D block, wherein i) the C block comprises a second poly(alkylene oxide) backbone, and ii) the D block comprises a steroidal repeat unit (repeat unit 2) comprising both a backbone carbonate and a side chain steroid functional group, and
- the triblock copolymer and the loaded micelle are bound by noncovalent interactions.

18. The method of claim 17, wherein the triblock copolymer and the diblock copolymer are mixed in water.

19. The method of claim 18, wherein the triblock copolymer alone is not soluble in the water until mixed with the loaded micelle.

20. The method of claim 17, wherein the triblock copolymer is formed by an organocatalyzed ring opening polymerization of a cyclic carbonate monomer initiated by poly(alkylene glycol), the cyclic carbonate monomer having the formula (6):

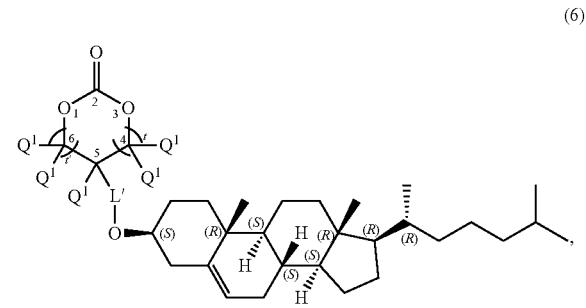

(6)

wherein
- t is an integer having a value of 0 to 6,
- t' is an integer having a value of 0 to 6,
- t' and t cannot both be zero,
- each $Q^1$ is an independent monovalent radical selected from the group consisting of hydrogen, halides, alkyl groups comprising 1 to 30 carbons, and aryl groups comprising 6 to 30 carbon atoms, and
- L' is a divalent linking group comprising one or more carbons.

21. A composite hydrogel for controlled release of a biologically active substance, comprising:

an amphiphilic triblock copolymer (ABA) having the structure:

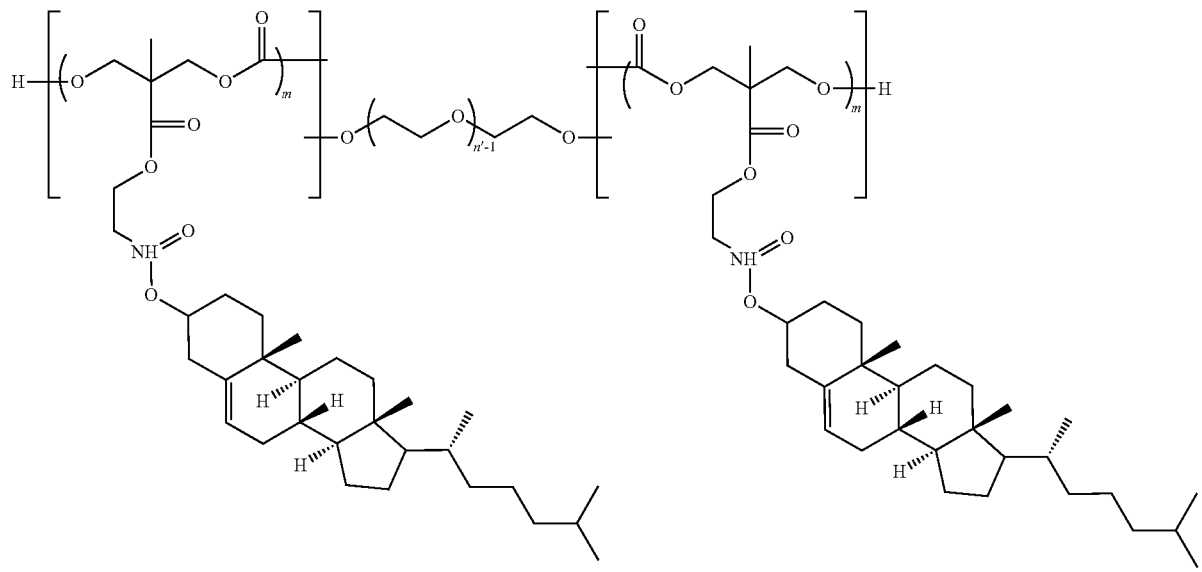

wherein each m is an independent number having a value of about 0.8 to about 2.5, and n' has a value of about 200 to about 800; and a loaded micelle comprising i) the biologically active substance and ii) an amphiphilic diblock copolymer (CD) having the structure:

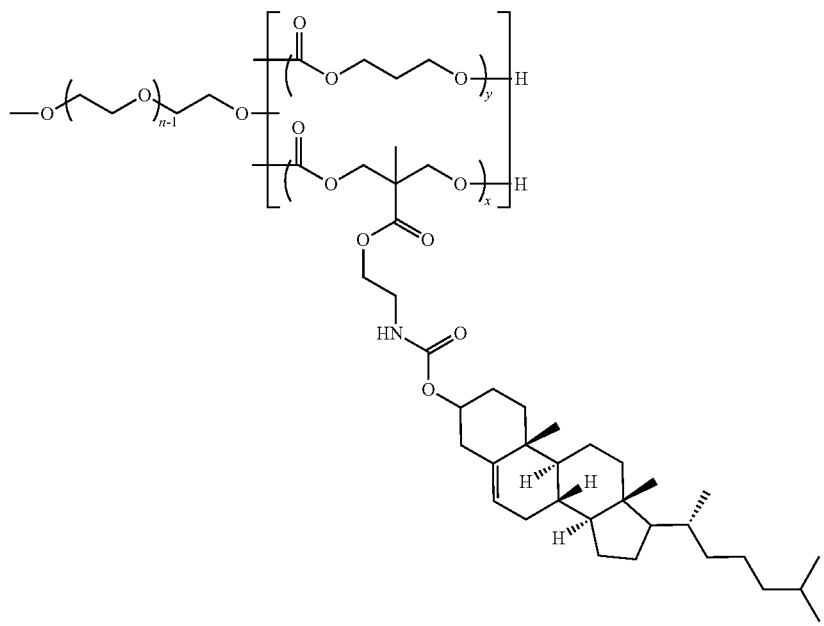

wherein n has a value of about 100 to about 120, x has a value of about 11, and y has a value of about 30, and wherein the amphiphilic triblock copolymer and the loaded micelle are bound by noncovalent interactions.

22. The composite hydrogel of claim 21, wherein the biologically active substance is a drug.

23. The composite hydrogel of claim 22, wherein the drug is selected from the group consisting of cyclosporin A, paclitaxel, spironolactone, and combinations thereof.

24. A triblock copolymer having the formula (19)

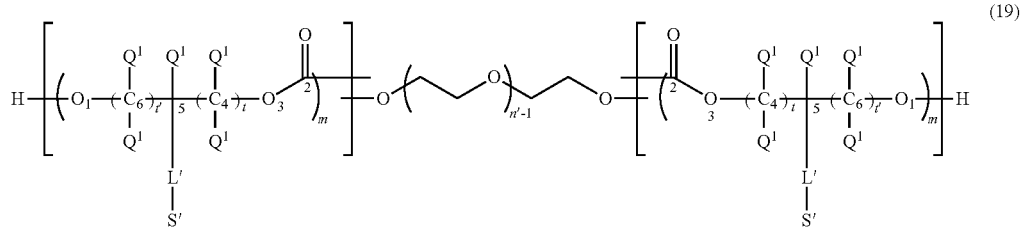

(19)

wherein
each m is an independent number having a value of about 0.8 to about 4,
n' has a value of about 200 to about 800,
each t is an independent integer having a value of 0 to 6,
each t' is an independent integer having a value of 0 to 6,
t' and t cannot both be zero in any repeat unit,
each $Q^1$ is an independent monovalent radical selected from the group consisting of hydrogen, halides, alkyl groups comprising 1 to 30 carbons, and aryl groups comprising 6 to 30 carbon atoms,
each L' is an independent linking group selected from the group consisting of a single bond and divalent radicals comprising 1 to 30 carbons, and
each S' is an independent steroid group.

25. The triblock copolymer of claim 24, wherein S' is cholesteryl.

26. The triblock copolymer of claim 24, wherein the triblock copolymer has the formula (20),

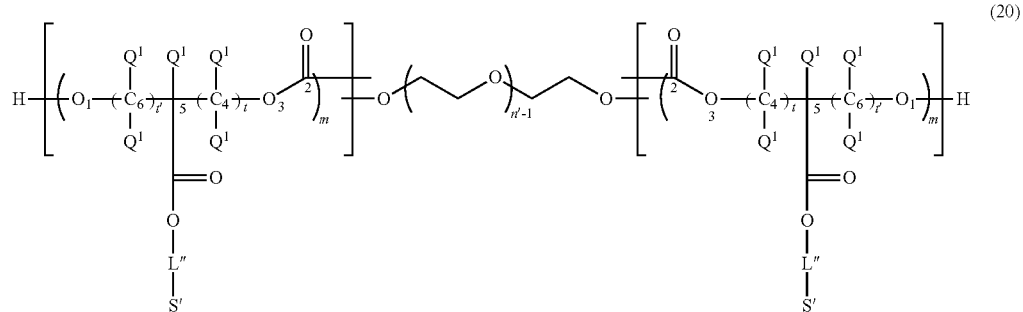

(20)

wherein
each m is an independent number having a value of about 0.8 to about 4,
n' has a value of about 200 to about 800,
each t is an independent integer having a value of 0 to 6,
each t' is an independent integer having a value of 0 to 6,
t' and t cannot both be zero in any repeat unit,
each $Q^1$ is an independent monovalent radical selected from the group consisting of hydrogen, halides, alkyl groups comprising 1 to 30 carbons, and aryl groups comprising 6 to 30 carbon atoms,
each L" is an independent linking group selected from the group consisting of a single bond and divalent radicals comprising 1 to 30 carbons, and
each S' is an independent steroid group.

27. The triblock copolymer of claim 24, wherein the triblock copolymer has the formula (21),
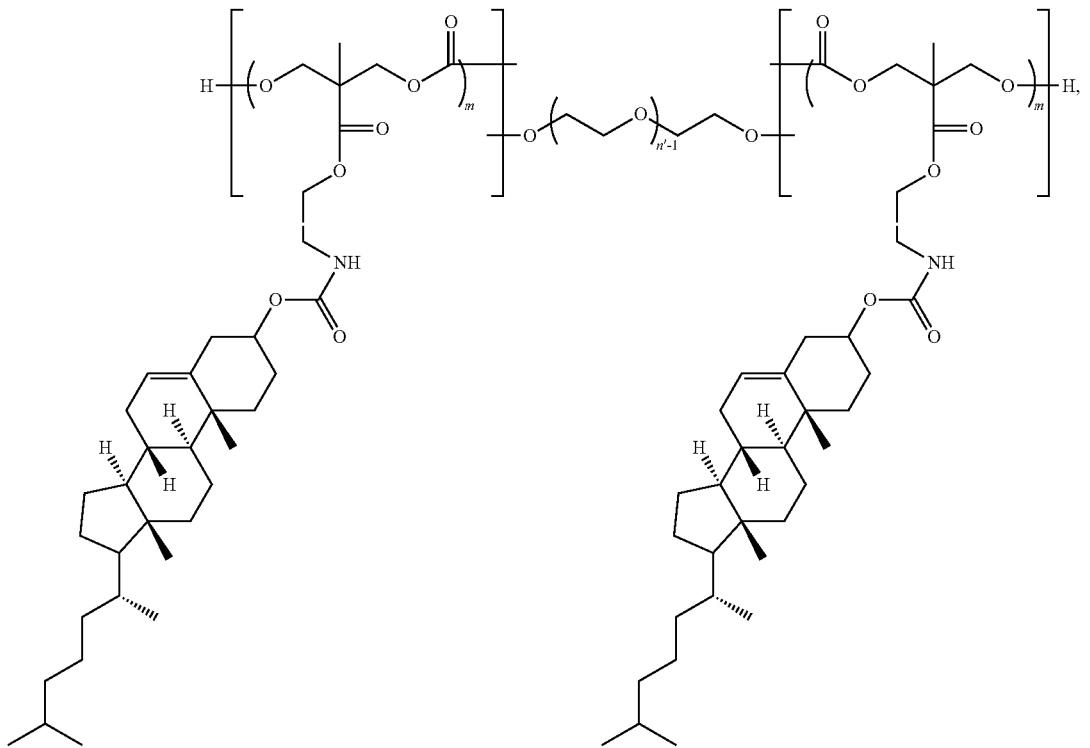
wherein each m is an independent number having a value of about 0.8 to about 4.0, and n' has a value of about 200 to about 800.
* * * * *